United States Patent [19]

Hirayama et al.

[11] Patent Number: 5,869,501
[45] Date of Patent: Feb. 9, 1999

[54] AMIDINONAPHTHYL DERIVATIVE OR SALT THEREOF

[75] Inventors: Fukushi Hirayama; Hiroyuki Koshio; Yuzo Matsumoto; Tomihisa Kawasaki, all of Ibaraki; Seiji Kaku, Shizuoka; Isao Yanagisawa, Tokyo, all of Japan

[73] Assignee: Yamanouchi Pharmaceutical Co. Ltd, Tokyo, Japan

[21] Appl. No.: 849,391

[22] PCT Filed: Dec. 1, 1995

[86] PCT No.: PCT/JP95/02458

§ 371 Date: May 30, 1997

§ 102(e) Date: May 30, 1997

[87] PCT Pub. No.: WO96/16940

PCT Pub. Date: Jun. 6, 1996

[30] Foreign Application Priority Data

| Dec. 2, 1994 | [JP] | Japan | ................................... | 6-299963 |
| Apr. 28, 1995 | [JP] | Japan | ................................... | 7-105205 |
| Aug. 3, 1995 | [JP] | Japan | ................................... | 7-198816 |

[51] Int. Cl.[6] ........................ A61K 31/445; C07D 211/44
[52] U.S. Cl. ......................... 514/319; 514/424; 546/205; 546/221; 548/541; 548/550
[58] Field of Search .................... 546/205, 221; 548/541, 550; 514/319, 424

[56] References Cited

U.S. PATENT DOCUMENTS

| 4,563,527 | 1/1986 | Fujii et al. | ............................... | 546/169 |
| 4,634,783 | 1/1987 | Fujii et al. | ............................... | 549/475 |
| 5,576,343 | 11/1996 | Nagahara | ............................... | 514/422 |

FOREIGN PATENT DOCUMENTS

| 048433 | 3/1982 | European Pat. Off. . |
| 0540051 | 5/1993 | European Pat. Off. . |

OTHER PUBLICATIONS

Delgado JN and Remers WA. Textbook of Organic Medicinal and Pharmaceutical Chemistry. Ninth Edition. pp. 30–31, 1991.

Primary Examiner—Evelyn Huang
Attorney, Agent, or Firm—Burgess, Ryan & Wayne

[57] ABSTRACT

An amidinonaphthyl derivative represented by the following general formula (I) which has coagulation factor X inhibiting action and is useful as an anti-thrombus agent and the like, a salt thereof, an intermediate thereof and a pharmaceutical composition which comprises the amidinonaphthyl derivative. An amidinonaphthyl derivative represented by the following general formula (I) or a pharmaceutically acceptable salt thereof.

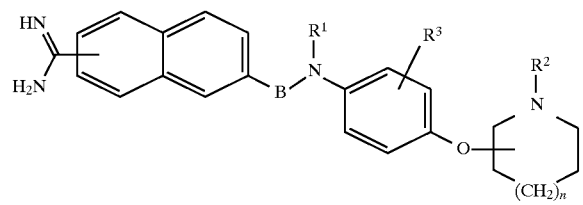

(symbols in the formula have the following meanings;

$R^1$: a hydrogen atom or a group represented by the formula —A—W—$R^4$,

A: a group represented by the formula

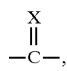

a group represented by the formula

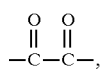

or a group represented by the formula —$SO_2$—, X: an oxygen atom or a sulfur atom, W: a single bond or a group represented by the formula —$NR^5$—, $R^4$: a hydroxyl group, a lower alkoxy group, etc., $R^5$: a hydrogen atom, a carbamoyl group, a lower alkoxycarbonyl group, etc., $R^2$: a lower alkyl group, $R^3$: a hydrogen atom, a halogen atom, a carboxyl group, B: a lower alkylene group or a carbonyl group, and n: 0 or 1).

20 Claims, No Drawings

AMIDINONAPHTHYL DERIVATIVE OR SALT THEREOF

This application is the national phase of PCT/JP95/02458, filed on Dec. 1, 1995, published as WO 96/16940 on Jun. 6, 1996.

1. Technical Field

This invention relates to an amidinonaphthyl derivative or a salt thereof, which is useful as medicine, particularly as an activated blood coagulation factor X inhibitor.

2. Background Art

With the changes in European and American life styles and the increase in aged population in recent years, the number of patients with thromboembolic diseases including myocardial infarction, cerebral thrombosis and peripheral arterial thrombosis have been increasing from year to year, and social importance of their treatment has been increasing more and more. As well as the fibrinolysis therapy and antiplatelet therapy, the anticoagulation therapy takes a part of the medical therapy in treating and preventing thrombosis (*Sogo Rinsyo,* 41: 2141–2145, 1989). In particular, the safety which withstands long-term administration and accurate and proper expression of the anticoagulation activity are essential in the prevention of thrombosis.

Warfarin potassium is frequently used in the world as the sole oral anticoagulant. However, this drug is extremely difficult to use clinically, because it is difficult to control the anticoagulation capacity due to the characteristics based on its action mechanism (*J. Clinical Pharmacology,* 32, 196–209, 1992, and *N. Eng. J. Med.,* 324 (26), 1865–1875, 1991), so that great concern has been directed toward the development of a more useful and easily usable anticoagulant.

Since thrombin controls conversion of fibrinogen into fibrin, which is the final step of coagulation, and is also concerned deeply in the activation and aggregation of platelets (*T-PA and Pro-UK,* edited by O. Matsuo, published by Gakusai Kikaku, pp. 5–40 Blood Coagulation, 1986), its inhibitor has been the center of anticoagulant studies as a target of drug developments. However, thrombin inhibitors which can be administered orally have not been reported until now because of their low bioavailability by oral administration and problems from the safety point of view (*Biomed. Biochim. Acta,* 44, 1201–1210, 1985).

Activated blood coagulation factor X is a key enzyme which is located at the joining point of the extrinsic and intrinsic coagulation cascade reactions and locates upstream to thrombin, so that there is a possibility that inhibition of this factor is more efficient than the thrombin inhibition and such an inhibitor can inhibit the coagulation system in a specific fashion (*THROMBOSIS RESEARCH* (19), 339–349, 1980).

As a patent which discloses a compound having an activated blood coagulation factor X inhibiting action, an unexamined published Japanese patent application (kokai) No. 5-208946 discloses an amidinonaphthylbenzene derivative represented by the following general formula or a salt thereof;

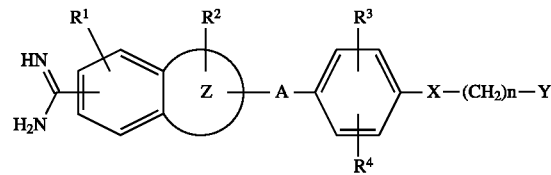

(in the formula, an omission, A: an alkylene group having 1 to 4 carbon atoms which may be substituted with 1 to 2 of hydroxyalkyl, carboxyl, alkoxycarbonyl, carboxylalkyl or alkoxycarbonylalkyl group, Y represents a saturated or unsaturated 5 to 6 membered heterocyclic group or cyclic hydrocarbon group or the like, which may have a substituent group, the rest omitted).

However, the compound of the present invention is a novel compound which is clearly different from the aforementioned compound in the structure since the amidinonaphthylalkyl group or amidinonaphthylcarbonyl group is linked to a substituted phenyl group via a nitrogen atom. In addition, as will be described later, the compound of the present invention is a compound having markedly excellent activated blood coagulation factor X inhibiting action in comparison with the aforementioned compound.

DISCLOSURE OF THE INVENTION

With the aim of providing a compound having excellent activated blood coagulation factor X inhibiting action, the inventors of the present invention carried out extensive studies. As the result, it was found unexpectedly that a compound in which an amidinonaphthylalkyl group or amidinonaphthylcarbonyl group is linked to a substituted phenyl group via a nitrogen atom, particularly a compound in which a group represented by the formula —A—W—R4 is substituted on the nitrogen atom, has a markedly excellent activated blood coagulation factor X inhibiting action, thereby resulting in the accomplishment of the present invention.

Accordingly, the present invention relates to an amidinonaphthyl derivative represented by the following general formula (I) or a pharmaceutically acceptable salt thereof.

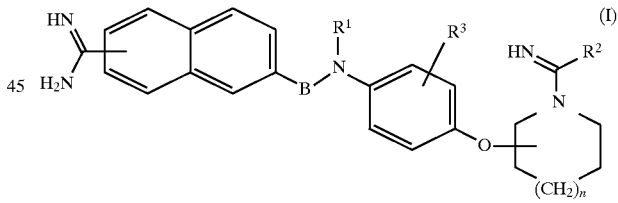

(symbols in the formula have the following meanings;
 $R^1$: a hydrogen atom or a group represented by the formula —A—W—$R^4$,
 A: a group represented by the formula

a group represented by the formula

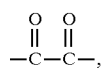

or a group represented by the formula —SO$_2$—,

X: an oxygen atom or a sulfur atom,

W: a single bond or a group represented by the formula —NR$^5$—,

R$^4$: a hydroxyl group, a lower alkoxy group, a lower alkyl group which may be substituted, a cycloalkyl group which may be substituted, an aryl group which may be substituted, or a heteroaryl group which may be substituted, with the proviso that, when W is a group represented by the formula —NR$^5$—, R$^4$ may further be a hydrogen atom but is not a hydroxyl group or a lower alkoxy group, R$^5$: a hydrogen atom, a carbamoyl group, a lower alkoxycarbonyl group, a mono- or di-lower aminocarbonyl group, a lower alkylsulfonyl group, a mono- or di-lower aminothicarbonyl group, a lower alkyl group which may be substituted, or a lower alkanoyl group which may be substituted, R$^2$: a lower alkyl group, R$^3$: a hydrogen atom, a halogen atom, a carboxyl group, an amino group, a cyano group, a nitro group, a hydroxyl group, a lower alkoxy group, a lower alkyl group, or a lower alkoxycarbonyl group, B: a lower alkylene group or a carbonyl group, and n: 0 or 1. The same apply hereinafter.).

The compound (I) of the present invention is preferably an amidinonaphthyl derivative or a pharmaceutically acceptable salt thereof in which the lower alkyl group which may be substituted in the meaning of R$^4$ or R$^5$, the cycloalkyl group which may be substituted in the meaning of R$^4$ or the lower alkanoyl group which may be substituted in the meaning of R$^5$ is a lower alkyl group, a cycloalkyl group or a lower alkanoyl group which may be substituted with a member of the following group C, and the aryl group which may be substituted or the heteroaryl group which may be substituted in the meaning of R$^4$ is an aryl group or a heteroaryl group which may be substituted with a member of the following group D, (group C: a halogen atom, a carboxyl group, a carbamoyl group, an amino group, a cyano group, a nitro group, a lower alkanoyl group, a lower alkoxy group, a lower alkoxycarbonyl group, a mono- or di-lower alkylamino group, an aryl group, an aralkyloxy group, an aryloxy group, a mercapto group, a lower alkylthio group, a lower alkylthiocarbonyl group, a hydroxyl group or a mono- or di-lower alkylaminocarbonyl group.

group D: a halogen atom, a carboxyl group, an amino group, a cyano group, a nitro group, a hydroxyl group, a lower alkoxy group, a lower alkoxycarbonyl group, a mono- or di-lower alkylamino group, a lower alkanoyl group or a lower alkyl group which may be substituted with a member of the group C);

more preferably an amidinonaphthyl derivative or a pharmaceutically acceptable salt thereof in which R$^4$ is a hydroxyl group; a lower alkoxy group; a lower alkyl group which may be substituted with a halogen atom, a carboxyl group, a carbamoyl group, an amino group, a lower alkoxy group, a lower alkoxycarbonyl group, a mono- or di-lower alkylamino group or a phenyl group; a cycloalkyl group which may be substituted with a halogen atom, a carboxyl group, a carbamoyl group, an amino group, a lower alkoxy group, a lower alkoxycarbonyl group, a mono- or di-lower alkylamino group or a phenyl group; an aryl group which may be substituted with a halogen atom, an amino group, a nitro group, a carboxyl group, a lower alkoxycarbonyl group or a lower alkoxy group; or a heteroaryl group which may be substituted with a halogen atom, an amino group, a nitro group, a carboxyl group, a lower alkoxycarbonyl group or a lower alkoxy group (with the proviso that, when W is a group represented by the formula —NR$^5$—, R$^4$ may further be a hydrogen atom but is not a hydroxyl group or a lower alkoxy group), R$^5$ is a hydrogen atom; a carbamoyl group; a carboxyl group; a lower alkoxycarbonyl group; a lower alkanoyl group; a mono- or di-lower alkylaminothiocarbonyl group; or a lower alkyl group which may be substituted with a halogen atom, a carbamoyl group, an amino group, a lower alkoxy group, a lower alkoxycarbonyl group, a mono- or di-lower alkylamino group or a phenyl group, and R$^3$ is a hydrogen atom, a halogen atom, a carboxyl group, a lower alkoxy group, a lower alkyl group, or a lower alkoxycarbonyl group.

Most preferred is an amidinonaphthyl derivative or a pharmaceutically acceptable salt thereof in which the group represented by the formula —A—W—R$^4$ is a group selected from the group consisting of a lower alkanoyl group which may be substituted with a lower alkoxy group, a lower alkoxycarbonyl group or a mono- or di-lower alkylamino group; an aminocarbonyl group which may be substituted with a lower alkoxycarbonyl group; a lower alkylsulfonyl group which may be substituted with a halogen atom, a carboxyl group, a carbamoyl group, a lower alkoxycarbonyl group or a phenyl group; a mono- or di-lower alkylaminocarbonyl group which may be substituted with a carboxyl group or a lower alkoxycarbonyl group; an aminosulfonyl group which may be substituted with a lower alkoxycarbonyl group; a mono- or di-lower alkylaminosulfonyl group which may be substituted with a carbamoyl group, a carboxyl group or a lower alkoxycarbonyl group; an N-lower alkyl-N-lower alkoxycarbonylaminosulfonyl group which may be substituted with a carboxyl group or a lower alkoxycarbonyl group; a benzoyl group which may be substituted with a carboxyl group, a lower alkoxycarbonyl group, a halogen atom or a lower alkoxy group; a benzenesulfonyl group which may be substituted with an amino group, a nitro group, a carboxyl group or a lower alkoxycarbonyl group; a naphthoyl group; a mono-lower alkylaminothiocarbonyl group; a pyridylcarbonyl group; a thienylcarbonyl group; an aminooxalyl group; or a cycloalkylcarbonyl group, and R$^3$ is a hydrogen atom or a lower alkoxycarbonyl group.

Also preferred is an amidinonaphthyl derivative or a pharmaceutically acceptable salt thereof, in which A is a group represented by the formula

or a group represented by the formula —SO$_2$—.

Another object of the present invention is to provide a compound represented by the following general formula (I') or a salt thereof, which is useful as an intermediate for the object compound (I) of the present invention.

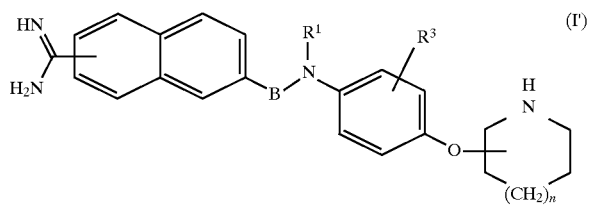

Still another object of the present invention is to provide a medicine, particularly an activated blood coagulation factor X inhibitor, which contains the amidinonaphthylbenzene derivative represented by the general formula (I) or a salt thereof as an active ingredient.

The following describes the present invention further in detail.

In the definition of groups of the general formula in the specification, the term "lower" means a straight or branched carbon chain having 1 to 6 carbon atoms unless otherwise noted.

In consequence, illustrative examples of the "lower alkyl group" include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group and a 1-ethyl-2-methylpropyl group, of which those having 1 to 3 carbon atoms are preferred and a methyl group and an ethyl group are particularly preferred.

Illustrative examples of the "lower alkoxy group" include a methoxy group, an ethoxy group, a propoxy group, an isopropoxy group, a butoxy group, an isobutoxy group, a sec-butoxy group, a tert-butoxy group, a pentyloxy (amyloxy) group, an isopentyloxy group, a tert-pentyloxy group, a neopentyloxy group, a 2-methylbutoxy group, a 1,2-dimethylpropoxy group, a 1-ethylpropoxy group, a hexyloxy group and the like, of which those having 1 to 3 carbon atoms are preferred, and a methoxy group and an ethoxy group are particularly preferred.

As the "cycloalkyl group", cycloalkyl groups having 3 to 8 carbon atoms, such as a cyclopropyl group, a cyclobutyl group, a cyclopentyl group, a cyclopentyl group, a cyclohexyl group, a cycloheptyl group, a cyclooctyl group and the like, of which a cyclopropyl group, a cyclobutyl group, a cyclopentyl group and a cyclohexyl group and the like are preferred.

Illustrative examples of the "aryl group" are hydrocarbon ring aryl groups having 6 to 14 carbon atoms, such as a phenyl group, a naphthyl group, a biphenyl group, an anthryl group and the like, of which a phenyl group and a naphthyl group are preferred.

The "heteroaryl group" is a single ring or condensed ring heteroaryl group having 1 to 3 hetero atoms of an oxygen atom, a sulfur atom, a nitrogen atom, etc., and its illustrative examples include a furyl group, a thienyl group, a pyrrolyl group, an imidazolyl group, a pyrazolyl group, an isothiazolyl group, an isoxazolyl group, a pyridyl group, a pyrimidinyl group, a quinolyl group, an isoquinolyl group, a quinazolinyl group, a quinolizinyl group, a quinoxalinyl group, a cinnolinyl group; a benzimidazolyl group, an imidazopyridyl group, a benzofuranyl group, a naphthyridinyl group, a 1,2-benzoisoxazolyl group, a benzoxazolyl group, a benzothiazolyl group, an oxazolopyridyl group, an isothiazolopyridyl group, a benzothienyl group and the like, of which heteroaryl groups such as a furyl group, a thienyl group, a pyrrolyl group, an imidazolyl group, a pyridyl group and the like are preferred.

The "lower alkoxycarbonyl group" is a group formed from a straight or branched alcohol having 1 to 6 carbon atoms and a carboxyl group by esterification, such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group and the like, of which those having 1 to 3 carbon atoms are preferred, and a methoxycarbonyl group and an ethoxycarbonyl group are particularly preferred.

The "mono- or di-lower alkylaminocarbonyl group" means a group in which one or two hydrogen atoms of an amino group is substituted with the aforementioned "lower alkyl group". Illustrative examples of the mono-lower alkylaminocarbonyl group include a methylaminocarbonyl group, an ethylaminocarbonyl group, a propylaminocarbonyl group, an isopropylaminocarbonyl group, a butylaminocarbonyl group, an isobutylaminocarbonyl group, a pentylaminocarbonyl group, an isopentylaminocarbonyl group, a hexylaminocarbonyl group, an isohexylaminocarbonyl group and the like. Illustrative examples of the dialkylaminocarbonyl group include symmetric dialkylaminocarbonyl groups which are di-substituted with straight or branched alkyl groups having 1 to 6 carbon atoms, such as a dimethylaminocarbonyl group, a diethylaminocarbonyl group, a dipropylaminocarbonyl group, a diisopropylaminocarbonyl group, a dibutylaminocarbonyl group, a dipentylaminocarbonyl group and the like, and asymmetric dialkylaminocarbonyl groups which are di-substituted with different straight or branched alkyl groups having 1 to 6 carbon atoms, such as an ethylmethylaminocarbonyl group, a methylpropylaminocarbonyl group, an ethylpropylaminocarbonyl group, a butylmethylaminocarbonyl group, a butylethylaminocarbonyl group, a butylpropylaminocarbonyl group and the like.

Illustrative examples of the "lower alkylsulfonyl group" include a methylsulfonyl group, an ethylsulfonyl group, a propylsulfonyl group, an isopropylsulfonyl group, a butylsulfonyl group, an isobutylsulfonyl group, a pentylsulfonyl group, an isopentylsulfonyl group, a hexylsulfonyl group, an isohexylsulfonyl group and the like.

The "mono- or di-lower alkylaminothiocarbonyl group" means a group in which one or two hydrogen atoms of an amino group is substituted with-the aforementioned "lower alkyl group". Illustrative examples of the mono-lower alkylaminothiocarbonyl group include a methylaminothiocarbonyl group, an ethylaminothiocarbonyl group, a propylaminothiocarbonyl group, an isopropylaminothiocarbonyl group, a butylaminothiocarbonyl group, an isobutylaminothiocarbonyl group, a pentylaminothiocarbonyl group, an isopentylaminothiocarbonyl group, a hexylaminothiocarbonyl group, an isohexylaminothiocarbonyl group and the like. Illustrative examples of the dialkylaminothiocarbonyl group include symmetric dialkylaminothiocarbonyl groups which are di-substituted with straight or branched alkyl groups having 1 to 6 carbon atoms, such as a dimethylaminothiocarbonyl group, a diethylaminothiocarbonyl group, a dipropylaminothiocarbonyl group, a diisopropylaminothiocarbonyl group, a dibutylaminothiocarbonyl group, a dipentylaminothiocarbonyl group and the like, and asymmetric dialkylaminothiocarbonyl groups which are di-substituted with different straight or branched alkyl groups having 1 to 6 carbon atoms, such as an ethylmethylaminothiocarbonyl group, a methylpropylaminothiocarbonyl group, an ethylpropylaminothiocarbonyl group, a butylmethylaminothiocarbonyl group, a butylethylaminothiocarbonyl group, a butylpropylaminothiocarbonyl group and the like.

Illustrative examples of the "lower alkanoyl group" include a formyl group, an acetyl group, a propionyl group, a butyryl group, an isobutyryl group, a valeryl group, an isovaleryl group, a pivaloyl group, a hexanoyl group and the like, of which an acetyl group, a propionyl group and a butyryl group are preferred, and an acetyl group and a propionyl group are particularly preferred.

The "lower alkylene group" is an alkylene group having 1 to 6 carbon atoms, and its illustrative examples include a methylene group, an ethylene group, a methylmethylene group, a trimethylene group, a dimethylmethylene group, a tetramethylene group, a methyltrimethylene group, an ethylethylene group, a dimethylethylene group, an ethylmethylmethylene group, a pentamethylene group, a methyltetramethylene group, a dimethyltrimethylene group, a trimethylethylene group, a diethylmethylene group, a hexamethylene group, a methylpentamethylene group, a dimethyltetramethylene and the like. Of these groups, alkylene groups of 1 to 3 carbon atoms such as a methylene group, an ethylene group, a methylmethylene group, a trimethylene group and a dimethylmethylene group are preferred; a methylene group and an ethylene group are more preferable; and a methylene group is the most preferable.

With respect to the substituent of the "lower alkyl group which may be substituted", "cycloalkyl group which may be substituted" or "lower alkanoyl group which may be substituted", any group which can be substituted on the lower alkyl group, cycloalkyl group or lower alkanoyl group may be used, but a member of the following group C may be used preferably. Also, with respect to the substituent of the "aryl group which may be substituted" or "heteroaryl group which may be substituted", any group which can be substituted on the "aryl group" or "heteroaryl group" may be used, but a member of the following group D may be used preferably. These "lower alkyl group", "cycloalkyl group", "lower alkanoyl group", "aryl group" or "heteroaryl group" may be substituted with 1 or a plurality of, preferably 1 to 3, of the substituents.

Group C: a halogen atom, a carboxyl group, a carbamoyl group, an amino group, a cyano group, a nitro group, a lower alkanoyl group, a lower alkoxy group, a lower alkoxycarbonyl group, a mono- or di-lower alkylamino group, an aryl group, an aralkyloxy group, an aryloxy group, a mercapto group, a lower alkylthio group, a lower alkylthiocarbonyl group, a hydroxyl group, a carbamoyl group, or a mono- or di-lower alkylaminocarbonyl group.

Group D: a halogen atom, a carboxyl group, an amino group, a cyano group, a nitro group, a hydroxyl group, a lower alkoxy group, a lower alkoxycarbonyl group, a mono- or di-lower alkylamino group; a lower alkanoyl group, or a lower alkyl group which may be substituted with a member of the group C.

Examples of the "halogen atom" include a fluorine atom, a chlorine atom, an-iodine atom, a bromine atom and the like, and examples of the "mono- or di-lower alkylamino group" include mono-lower alkylamino groups such as a methylamino group, an ethylamino group, a propylamino group, an isopropylamino group, a butylamino group, an isobutylamino group, a pentylamino group, an isopentylamino group, a hexylamino group, an isohexylamino group and the like or straight or branched, symmetric or asymmetric di-lower alkylamino groups having 1 to 6 carbon atoms such as a dimethylamino group, a methylethylamino group, a diethylamino group, a dipropylamino group, an ethylpropylamino group, a dibutylamino group, a dipentylamino group and the like. The term "aralkyloxy group" means a group in which an optional hydrogen atom of the "lower alkoxy group" is substituted with the aforementioned "aryl group", and its illustrative examples include a benzyloxy group, a naphthylmethyloxy group, a phenetyloxy group, a phenylpropyloxy group and the like, and the term "aryloxy group" means a group in which the hydrogen atom of a hydroxyl group is substituted with the aforementioned "aryl group", and its illustrative examples include a phenyloxy group, a naphthyloxy group and the like.

The term "lower alkylthio group" means a group in which the hydrogen atom of a mercapto group is substituted with the aforementioned "lower alkyl group", and its illustrative examples include a methylthio group, an ethylthio group, a propylthio group, an isopropylthio group, a butylthio group, an isobutylthio group, a pentylthio group, an isopentylthio group, a hexylthio group and the like, and the term "lower alkylthiocarbonyl group" means a group in which a carbonyl group of the aforementioned "lower alkanoyl group" is substituted by a thiocarbonyl group, and its illustrative examples include a methylthiocarbonyl group, an ethylthiocarbonyl group, a propylthiocarbonyl group, an isopropylthiocarbonyl group, a butylthiocarbonyl group, a pentylthiocarbonyl group, a hexylthiocarbonyl group and the like.

The "mono- or di-lower alkylaminosulfonyl group" means a group in which one or two hydrogen atoms of aminosulfonyl group is substituted with the aforementioned "lower alkyl group". Illustrative examples of the mono-lower alkylaminosulfonyl group include a methylaminosulfonyl group, an ethylaminosulfonyl group, a propylaminosulfonyl group, an isopropylaminosulfonyl group, a butylaminosulfonyl group, an isobutylaminosulfonyl group, a pentylaminosulfonyl group, an isopentylaminosulfonyl group, a hexylaminosulfonyl group, an isohexylaminosulfonyl group and the like. Illustrative examples of the dialkylaminosulfonyl group include symmetric dialkylaminosulfonyl groups which are di-substituted with straight or branched alkyl groups having 1 to 6 carbon atoms, such as a dimethylaminosulfonyl group, a diethylaminosulfonyl group, a dipropylaminosulfonyl group, a diisopropylaminosulfonyl group, a dibutylaminosulfonyl group, a dipentylaminosulfonyl group and the like, and asymmetric dialkylaminosulfonyl groups which are di-substituted with different straight or branched alkyl groups having 1 to 6 carbon atoms, such as an ethylmethylaminosulfonyl group, a methylpropylaminosulfonyl group, an ethylpropylaminosulfonyl group, a butylmethylaminosulfonyl group, a butylethylaminosulfonyl group, a butylpropylaminosulfonyl group and the like. The term "N-lower alkyl-N-lower alkoxycarbonylaminosulfonyl group" means a group in which the hydrogen atom of the aminosulfonyl group is substituted with the aforementioned "lower alkyl group" and "lower alkoxycarbonyl group".

Its illustrative examples include an N-methyl-N-methoxycarbonylaminosulfonyl group, an N-methyl-N-ethoxycarbonylaminosulfonyl group, an N-ethyl-N-methoxycarbonylaminosulfonyl group, an N-ethyl-N-ethoxycarbonylaminosulfonyl group, an N-methyl-N-propoxycarbonylaminosulfonyl group, an N-ethyl-N-propoxycarbonylaminosulfonyl group, an N-propyl-N- propoxycarbonylaminosulfonyl group, an N-butyl-N-methoxycarbonylaminosulfonyl group, an N-butyl-N-ethoxycarbonylaminosulfonyl group and the like, of which a group substituted with an alkyl group of 1 to 3 carbon atoms and an alkoxycarbonyl group of 1 to 3 carbon atoms is preferred.

Illustrative example of the particularly preferred compound among the object compounds to be included in the present invention is an amidinonaphthyl derivative, or a pharmaceutically acceptable salt thereof, which is selected from the group consisting of N-[4-[(1-acetoimidoyl-4-piperidyl)oxy]phenyl]-N-[(7-amidino-2-naphthyl)methyl-N'-methylsulfamide, methyl N-[N-4-[(1-acetoimidoyl-4-piperidyl)oxy]phenyl]-N-[(7-amidino-2-naphthyl)methyl]sufamoyl]carbamate, 4-[N-4-[(1-acetoimidoyl- 4-piperidyl)oxy]phenyl]-N-[(7-amidino-2-naphthyl)methyl]sulfamoyl]benzoic acid, [N-[4-[(1-acetoimidoyl-4-piperidyl)oxy]phenyl]-N-[(7-amidino-2-naphthyl)methyl]sulfamoyl]acetic acid, ethyl N-[N-[4-[(1-acetoimidoyl-4-piperidyl)oxy]phenyl]-N-[(7-amidino-2-naphthyl)methyl]sulfamoyl]glycinate, N-[N-4-[(1-acetoimidoyl-4-piperidyl)oxy]phenyl]-N-[(7-amidino-2-naphthyl)methyl]sulfamoyl]-N-ethoxycarbonylglycine and N-[N-4-[(1-acetoimidoyl-4-piperidyl)oxy]phenyl]-N-[(7-amidino-2-naphthyl)methyl]sulfamoyl]glycine.

Since the compounds of the present invention contain asymmetric carbon atoms in some cases, various isomers such as geometrical isomers, tautomers, optical isomers and the like, either as mixtures or in isolated forms, are included in the compounds of the present invention.

The compound (I) of the present invention forms an acid addition salt in some cases. Also, it may form a salt with a base depending on the type of the substituent. Illustrative examples of such salts include acid addition salts with inorganic acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like, and salts with inorganic bases such as sodium, potassium, magnesium, calcium, aluminum and the like or with organic bases such as methylamine, ethylamine, ethanolamine, lysine, ornithine and the like, as well as ammonium salt and the like.

In addition, hydrates, pharmaceutically acceptable various solvates and polymorphism of the compound (I) are also included in the present invention. As a matter of course, the present invention is not limited to the compounds described in the following Examples, but includes all of the amidinonaphthyl derivatives represented by the general formula (I) and pharmaceutically acceptable salts thereof.

(Production method)

The following describes typical production method of the invention compound (I). Also, since the intermediate compound represented by the general formula (I') as another object compound of the present invention is a novel compound, its production method is described in the first production step.

First step

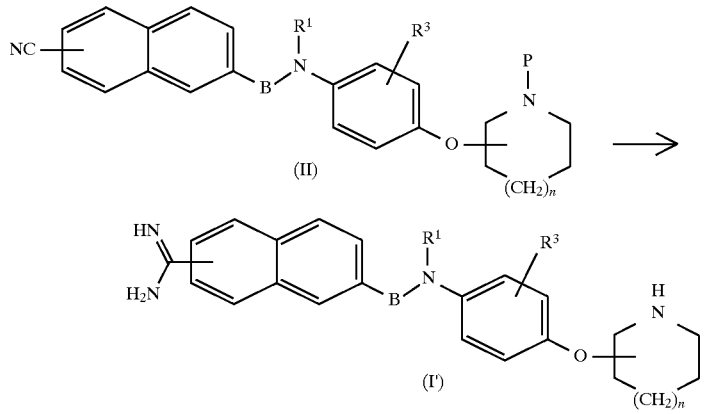

(In the formula, P means an amino-protecting group.)

As the amino-protecting group P, the groups commonly used for the protection of an amino group can be used with no particular limitation, such as a lower alkyloxycarbonyl group, an aralkyloxycarbonyl group, an acyl group, a lower alkyl group, an aralkyl group, a sulfonyl group and the like.

The compound (I') of the present invention can be synthesized by the following method (i), (ii) or (iii).

(i) A method in which a nitrile is converted into an imidate and then condensed with an amine:

The nitrile (II) is allowed to react with an alcohol such as methanol, ethanol or the like at −40° C. to 0° C. in the presence of hydrochloric acid gas, and then the thus formed imidate is allowed to react with ammonia, ammonium carbonate, ammonium chloride, ammonium acetate, or the other amine or amine salt. As the solvent, methanol, ethanol, acetone, tetrahydrofuran and the like can be used.

(ii) A method in which a nitrile is converted into a thioamide and then into a thioimidate which is subsequently condensed with an amine:

The nitrile (II) is allowed to react with hydrogen sulfide in the presence of an organic base such as methylamine, triethylamine, pyridine, picoline or the like to give a thioamide. The thioamide can also be obtained by allowing the nitrile (II) to react with o,o-diethyl dithiophosphate in the presence of hydrogen chloride.

The resulting thioamide is allowed to react with a lower alkyl halide such as methyl iodide, ethyl iodide or the like to convert it into a thioimidate which is then allowed to react with ammonia, ammonium carbonate, ammonium chloride, ammonium acetate, or other amine or amine salt. As the solvent, methanol, ethanol, acetone, tetrahydrofuran, ethyl acetate and the like can be used.

(iii) A method in which an amine, an amine salt, a metallic amide or a Grignard's reagent is directly added to a nitrile:

The synthesis can be carried out by adding a reagent such as ammonia, ammonium chloride and ammonia, ammonium thiocyanate, alkylammonium thiocyanate, MeAl(Cl)NH$_2$, NaNH$_2$, (CH$_3$)$_2$NMgBr or the like to the nitrile (II) in an appropriate solvent or without solvent. As the solvent, chloroform, methanol, ethanol, acetone, tetrahydrofuran, toluene, dimethylformamide and the like can be used. In some cases, the reaction is considerably accelerated when a base (e.g., sodium hydride), aluminum chloride, or an acid (e.g., p-toluenesulfonic acid) is used as a catalyst. The reaction can be carried out at cooling temperature to room temperature or with heating.

During the reaction to change a nitrile to an amidino group, the protecting group P of the nitrile (II) may be eliminated or not eliminated. When the protecting group P is not eliminated, the compound (I') of the present invention can be obtained by eliminating the protecting group P by a method suitable for its elimination, for example under an acidic condition with hydrochloric acid, acetic acid, trifluoroacetic acid or the like.

In addition, when an alkoxycarbonyl group is linked to the compound (II), it is possible to convert the alkoxycarbonyl group into a carbamoyl group simultaneously with the amidino formation reaction.

Second step

When an alkoxycarbonyl group is linked to the compound (I''), the hydrolysis can be carried out in the usual way under a basic, acidic or neutral condition, if necessary.

Examples of the base to be used under a basic condition include sodium hydroxide, potassium hydroxide, lithium hydroxide, barium hydroxide and the like, examples of the acid to be used under an acidic condition include Lewis acids such as hydrochloric acid, sulfuric acid, boron trichloride or the like, trifluoroacetic acid, p-toluenesulfonic acid and the like, and examples of the reagent to be used under a neutral condition include halogen ions such as of lithium iodide, lithium bromide and the like, alkali metal salts of thiol and cenolal, iodotrimethylsilane and an enzyme such as esterase. Examples of the solvent to be used in the reaction include water, alcohol (e.g., methanol and ethanol), acetone, dioxane, acetonitrile, tetrahydrofuran, N,N-dimethylformamide, dimethyl sulfoxide, formic acid, pyridine acetate, lutidine, collidine and the like. These solvents may be used as mixtures with water.

Though the reaction generally progresses at room temperature, it may be necessary to carry out the reaction in an ice bath or with heating in some cases, so that the reaction temperature should be optionally selected in the conventional way.

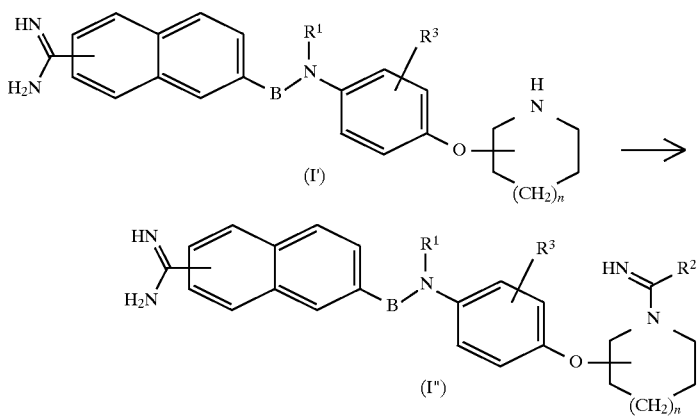

The compound (I'') of the present invention can be obtained by allowing the compound (I') which has a secondary amino group and which is produced in the aforementioned first step to react with an imidate compound in an appropriate solvent in the presence of a base at a cooling to heating temperature.

Examples of the solvent to be used include water, alcohols having 1 to 4 carbon atoms such as ethanol, propanol and the like, aliphatic ethers such as diethyl ether and the like, halogenated hydrocarbons such as chloroform and the like, N,N-dimethylformamide, dimethyl sulfoxide and the like and mixed solvents thereof.

Examples of the base include N-methylmorpholine, triethylamine, trimethylamine, sodium hydroxide, potassium hydroxide and the like.

In addition, the compound represented by the general formula (I) can be produced by optionally combining known steps which can be generally employed by those skilled in the art, such as alkylation, acylation, oxidation, reduction, hydrolysis and the like.

(Production method of starting compound)

Starting compounds (the following compounds (IVa), (IVb), (IVc), (IVd), (IVe) and (VII)) for the compound (I) of the present invention in which R$^1$ is a group represented by —A—W—R$^4$ can be produced by the following methods (a) to (f).

(a) Production method for an amide compound (IVa)

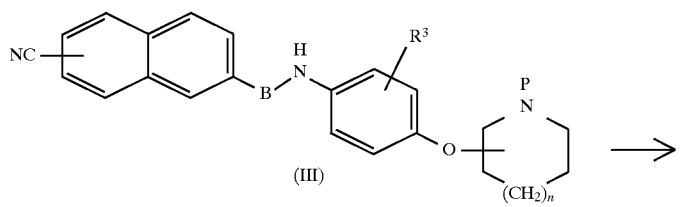

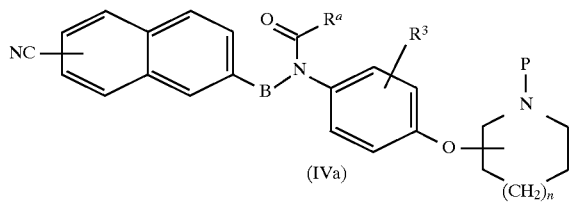

(IVa)

[In the formulae, $R^a$ is a group represented by $R_a^1$ or the formula

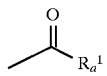

($R_a^1$ is a lower alkyl group which may have a substituent or an aryl group which may have a substituent, or a cycloalkyl group which may have a substituent or a lower alkoxy group).] The compound (IVa) which is an amide can be obtained by acylation of the amine (III) and an active derivative of a carboxylic acid in an appropriate solvent.

Examples of the active derivative of a carboxylic acid to be used include an active ester obtained by the reaction with a phenolic compound (e.g., p-nitrophenol) or N-hydroxyamine compound (e.g., 1-hydroxysuccinimide and 1-hydroxybenzotriazole); a monoalkyl carbonate, or an acid anhydride mixture obtained by reaction with an organic acid or a phosphoric acid anhydride mixture obtained by reaction of diphenylphosphoryl chloride with N-methylmorpholine; an acid azide obtained by allowing an ester with hydrazine or an alkyl nitrite; an acid halide (e.g., acid chloride and acid bromide); a symmetric acid anhydride and the like.

Alternatively, the amide compound (IVa) can also be obtained by acylation of the amine with a carboxylic acid in an appropriate solvent in the presence of a condensing agent. As the condensing agent of this case, N,N-dicyclohexylcarbodiimide (DCC), 1-ethyl-3-(3-(N,N-dimethylamino)propyl)carbodiimide, carbonyldiimidazole, diphenylphosphoryl azide (DPPA), diethylphosphoryl cyanide and the like are desirable.

The reaction is carried out generally in a solvent at cooling to room temperature. Examples of the solvent to be used are organic solvents which do not participate in the reaction, such as dimethylformamide, dimethylamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide and the like and mixed solvents thereof, and these organic solvents are optionally selected depending on the method to be employed. Depending on the type of acylation, it may be necessary to carry out the reaction under anhydrous condition.

Also, depending on the method to be employed, it may sometimes be desirable for a smooth reaction to carry out the reaction in the presence of a base such as N-methylmorpholine, triethylamine, trimethylamine, pyridine, sodium hydride, potassium t-butoxide, butyl lithium, sodium amide or using these bases as the solvent.

(b) Production method for an urea compound (IVb)

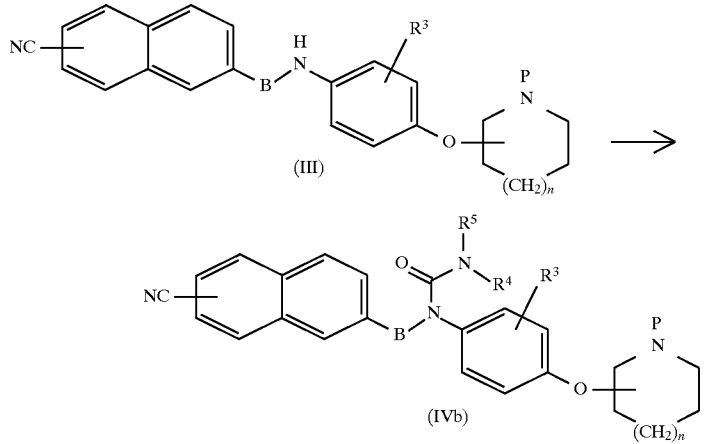

The urea compound (IVb) can be obtained by allowing the amine (III) to react with an isocyanate derivative in an appropriate solvent under cooling to reflux condition.

Alternatively, the urea compound (IVb) can also be obtained by allowing the amine (III) to react with phosgene, diphosgene or triphosgene in an appropriate solvent under cooling to reflux condition, and subsequently allowing the thus formed carbamoyl chloride to react with an amine derivative.

The solvent to be used is an organic solvent which does not participate in the reaction, and its illustrative examples include dimethylformamide, dimethylamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide and the like and mixed solvents thereof, and these organic solvents are optionally selected depending on the method to be employed.

Depending on the method to be employed, it may sometimes be desirable for a smooth reaction to carry out the reaction in the presence of a base such as triethylamine, trimethylamine, sodium hydride, potassium t-butoxide, butyl lithium, sodium amide or the like.

(c) Production method for a thiourea compound (IVc)

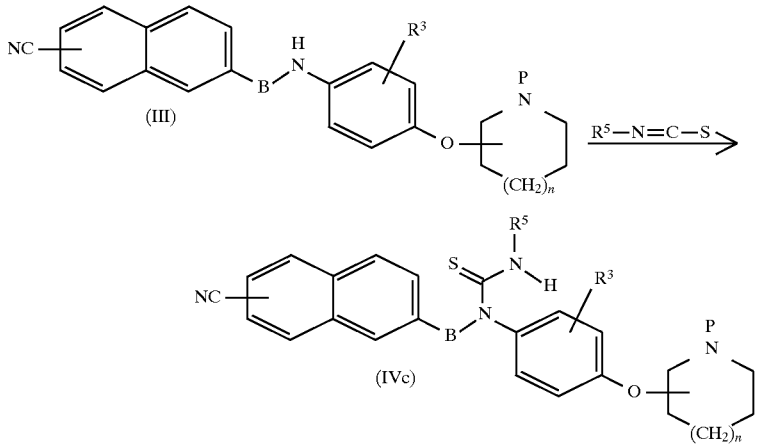

The thiourea compound (IVc) can be obtained by allowing the amine (III) to react with an isothiocyanate derivative in an appropriate solvent under cooling to reflux condition. The solvent to be used is an organic solvent which does not participate in the reaction, and its illustrative examples include dimethylformamide, dimethylamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide and the like and mixed solvents thereof, and these organic solvents are optionally selected depending on the method to be employed.

Depending on the method to be employed, it may sometimes be desirable for a smooth reaction to carry out the reaction in the presence of a base such as triethylamine, trimethylamine, sodium hydride, potassium t-butoxide, butyl lithium, sodium amide or the like.

(d) Production method for an urethane compound (IVd)

[In the formulae, $R^d$ is a lower alkyl group which may have a substituent.]

The urethane compound (IVd) can be obtained by allowing the amine (III) to react with an alkyl chloroformate which may have a substituent, an alkyl azidoformate which may have a substituent or an alkyl carbonate which may have a substituent, in an appropriate solvent under cooling to reflux condition.

The solvent to be used is an organic solvent which is does not participate in the reaction, and its illustrative examples include dimethylformamide, dimethylamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide and the like, and these organic solvents are optionally selected depending on the method to be employed.

Depending on the method to be employed, it may sometimes be desirable for a smooth reaction to carry out the reaction in the presence of a base such as triethylamine, trimethylamine, sodium hydride, potassium t-butoxide, butyl lithium, sodium amide or the like.

An oxalate compound can also be produced under the same reaction conditions except that a halogenoglyoxylic acid derivative is used as the-starting compound.

(e) Production method for a sulfonamide compound (IVe)

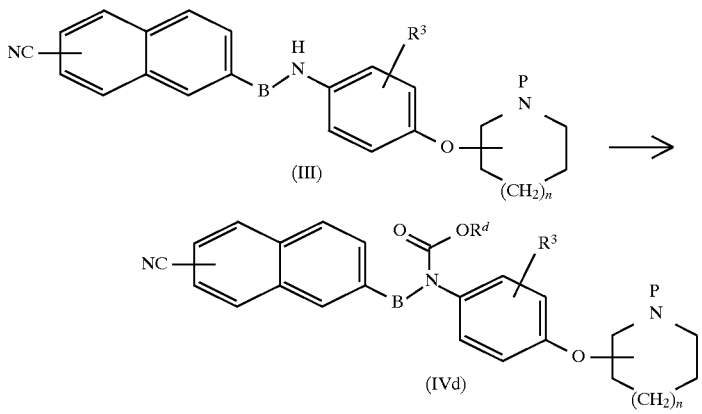

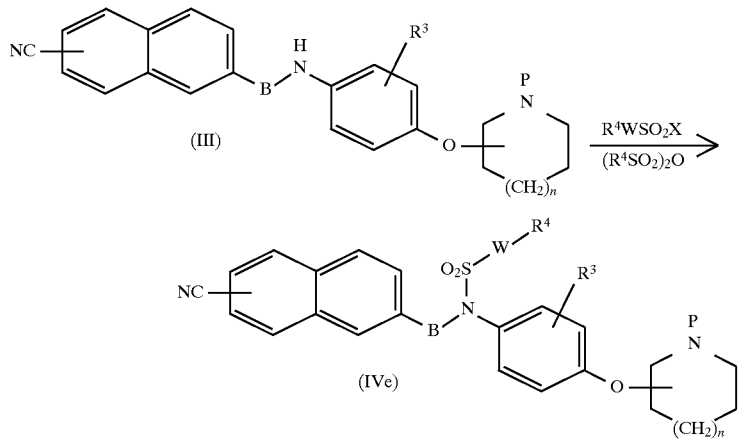

The sulfonamide compound (IVe) can be obtained by allowing the amine (III) to react with a sulfonyl halide derivative and a sulfonic anhydride generally in the presence of a base, in an appropriate solvent under cooling to reflux condition.

The solvent to be used is an organic solvent which does not participate in the reaction, and its illustrative examples include dimethylformamide, dimethylamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide and the like and mixed solvents thereof, and these organic solvents are optionally selected depending on the method to be employed. Illustrative examples of the base to be used include N-methylmorpholine, triethylamine, trimethylamine, pyridine, sodium hydride, potassium t-butoxide, butyl lithium, sodium amide and the like, and it is possible in some cases to use these bases as the solvent.

(f) Alkylation

This alkylation reaction is a well known reaction. Though this reaction is explained in the following with reference to an illustrative example, alkylation reactions other than the case of the illustrative example are also carried out under similar conditions.

[In the formulae, Y is an alkyl activating group such as a halogen atom, a methylsulfonyloxy group, a trifluoromethylsulfonyloxy group, a para-toluenesulfonyloxy group or the like.]

An alkylamine derivative represented by the general formula (VII) can be obtained by allowing an amine derivative represented by the general formula (V) to undergo alkylation by an alkylation agent represented by the general formula (VI). The alkylation reaction is carried out using the compound (V) and a reaction equivalent or excess amount of the alkylating agent (VI), in an appropriate solvent at cooling temperature to heating temperature, preferably from room temperature to heating (reflux) temperature. In this case, it is advantageous in some cases to add a reaction equivalent or excess amount of a base for a smooth reaction.

Solvents which do not participate in this reaction, alcohols (e.g., methanol and ethanol), hydrocarbons (e.g., benzene and toluene), or tetrahydrofuran, dioxane, acetonitrile, dimethylformamide, dimethyl sulfoxide and the like may be used optionally, though the reaction may be carried out without solvent in some cases.

Examples of the base to be used in this reaction include organic bases such as triethylamine, pyridine and the like, inorganic salts composed of strong bases, such as sodium

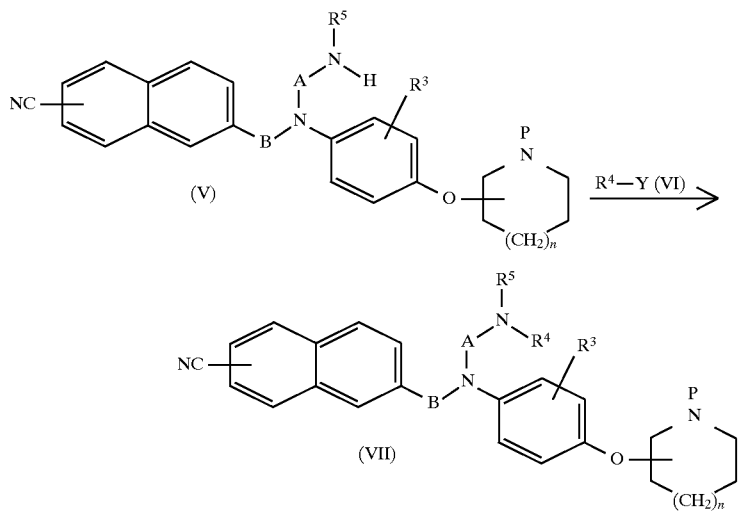

carbonate, potassium carbonate, sodium hydroxide and the like, and sodium hydride and the like. When a base is liquid, it may also be used as the solvent.

In addition, the starting compound of the present invention can be produced by optionally combining alkylation, oxidation, reduction, hydrolysis and the like other known steps which can be employed by those skilled in the art.

For example, in the case of the alkylation method, an alkyl-substituted sulfonamide compound can be obtained by carrying out reaction of a sulfonamide compound in the presence of its reaction equivalent amount or excess amount of an alcohol (e.g., methanol and ethanol), triphenylphosphine or diethyl azodicarboxylate in a solvent which does not participate in the reaction (e.g., tetrahydrofuran, benzene, dichloromethane or the like), while stirring at room temperature or with heating.

The reduction method is employed when an amine compound is obtained from a nitro compound. Its illustrative examples include a method in which a metal (e.g., zinc and tin) is used, a method in which a metal hydride (e.g., $LiAlH_4$) is used and a catalytic reduction method in which palladium-carbon or the like is used, and each of these methods is carried out in a solvent which does not participate in the reaction at room temperature or with heating.

The compound of the present invention produced in this way can be isolated and purified by known techniques such as extraction, precipitation, separation chromatography, fractionating crystallization, recrystallization and the like. Also, the compound of the present invention can be made into desired salts by subjecting it to usual salt forming reaction.

In addition, the compound of the present invention may exist in the form of optical isomers when it has asymmetric carbon atoms. These optical isomers can be separated in the usual way by a fractionating crystallization in which an isomer is recrystallized together with an appropriate salt or by a column chromatography.

INDUSTRIAL APPLICABILITY

The compound of the present invention shows potent anticoagulation action by inhibiting activated blood coagulation factor X in a specific fashion. In consequence, it is useful as a blood coagulation inhibitor or a drug for use in the prevention and treatment of diseases which are induced by thrombus or embolus. Examples of such diseases include cerebrovascular disorders such as cerebral infarction, cerebral thrombosis, cerebral embolism, transient cerebral ischemic attack (TIA), subarachnoid hemorrhage (vascular twitching) and the like, ischemic heart diseases such as acute or chronic myocardial infarction, unstable angina, coronary artery thrombolysis and the like, pulmonary vascular disorders such as pulmonary thrombosis, pulmonary embolism and the like, and various vascular disorders such as peripheral arterial obstruction, deep venous thrombosis, disseminated intravascular coagulation syndrome, thrombus formation after artificial blood vessel operation or after artificial valve replacement, re-occlusion and re-stricture after coronary artery by-pass operation, re-occlusion and re-stricture after PTCA or PTCR operation and thrombus formation at the time of extracorporeal circulation. In addition to the above, a possibility has been suggested on the use of the compound of the present invention as a drug for use in the prevention and treatment of influenza virus infection based on the activity to inhibit growth of influenza virus, effected by the activated blood coagulation factor X inhibiting action of the compound (an unexamined published Japanese patent application (kokai) No. 6-227971).

The excellent activity of the compound of the present invention to inhibit activated blood coagulation factor X has been confirmed by the following tests.

1) Test on the measurement of blood coagulation time by human activated blood coagulation factor X.

Human activated blood coagulation factor X (manufactured by Cosmo Bio) is dissolved in 0.05M Tris-HCl buffer (pH=7.40) to prepare a 0.05 unit/ml solution. A blood sample collected using $\frac{1}{10}$ volume of 3.8% sodium citrate was centrifuged at 3,000 rpm for 10 minutes. Then, 90 $\mu$l portion of the thus separated human plasma was mixed with 10 $\mu$l of each drug which has been diluted by dissolving in physiological saline and 50 $\mu$l of the aforementioned activated blood coagulation factor X solution, and the mixture was incubated at 37° C. for 3 minutes. Then, 100 $\mu$l of 20 mM $CaCl_2$ solution was added to measure the blood coagulation time. KC4A manufactured by Amelung was used for the measurement of blood coagulation time. A dose which extends the blood coagulation time twice (to be referred to as CT2 hereinafter) was calculated based on the blood coagulation time when 10 $\mu$l of physiological saline was added instead of the drug. The results are shown in Table 1.

2) Test on the measurement of coagulation time by bovine thrombin.

Human fibrinogen (freeze-dried preparation, manufactured by Sigma) is dissolved in 0.05M Tris-HCl buffer (pH=7.40) to prepare a 6 mg/ml solution. Bovine thrombin (500 IU/vial, manufactured by Mochida Pharmaceutical) is dissolved in physiological saline to prepare thrombin solutions of various concentrations. A 100 $\mu$l portion of the aforementioned fibrinogen solution was mixed with 100 $\mu$l of physiological saline, the mixture was incubated at 37° C. for 3 minutes. Then, 100 $\mu$l of the aforementioned thrombin solution was added to measure the coagulation time and to determine concentration of thrombin which causes coagulation after about 20 seconds. Next, 100 $\mu$l of each drug which has been diluted with physiological saline was added to 100 $\mu$l of the aforementioned fibrinogen solution to measure the coagulation time. KC4A manufactured by Amelung was used for the measurement of the coagulation time. A dose which extends the blood coagulation time twice (to be referred to as CT2 hereinafter) was calculated based on the blood coagulation time when 100 $\mu$l of physiological saline was added. The results are shown in Table 1.

3) Test on the measurement of enzyme inhibition by a synthetic substrate method.

Human activated blood coagulation factor X (manufactured by Cosmo Bio) was dissolved in 0.02M Tris-HCl buffer (pH=7.40) containing 0.15M sodium chloride to prepare a 6 units/ml solution. A synthetic substrate S-2222 (manufactured by Daiichi Kagaku Yakuhin) was dissolved in purified water to prepare a 0.75 mg/ml solution. A 25 $\mu$l portion of each drug which has been prepared by dissolving the drug in physiological saline was mixed with 170 $\mu$l of 0.05M Tris-HCl buffer (pH=8.40) and 50 $\mu$l of the S-2222 solution. Then, 10 $\mu$l of the human activated blood coagulation factor X solution was added and the mixture was incubated at 37° C. for 15 minutes. The reaction was stopped by adding 50 $\mu$l of 60% acetic acid and then the absorbance at 405 nm was measured to calculate $IC_{50}$ value. Model 3550 manufactured by Bio-Rad was used for the measurement. A reaction mixture prepared by adding physiological saline instead of the drug and adding 60% acetic acid prior to the addition of the human activated blood coagulation factor X solution was used as a control. Concentration of the drug when 50% of the reaction was inhibited (to be referred to as $IC_{50}$ hereinafter) was calculated based on the control. As the results, the compound of Example 79 for example showed a value of 0.091 $\mu$M ($IC_{50}$), and the compound of Example 88 showed a value of 0.047 $\mu$M ($IC_{50}$).

On the basis of the results of the aforementioned tests 1), 2) and 3), it was confirmed that the compound of the present invention inhibits human activated blood coagulation factor X in a specific fashion and shows excellent anticoagulation action by extending the coagulation time with a lower concentration than a reference compound described in the following.

TABLE 1

| Compounds tested | 1) Test on the measurement of blood coagulation time by human activated blood coagulation factor X | Test on the measurement of coagulation time by bovine thrombin |
|---|---|---|
| Example No. | CT2 ($\mu$M) | CT2 ($\mu$M) |
| 23 | 0.11 | >100 |
| 28 | 0.05 | >100 |
| 31 | 0.09 | >100 |
| 33 | 0.14 | >100 |
| 47 | 0.13 | >100 |
| 63 | 0.04 | >100 |
| 74 | 0.09 | >100 |
| 79 | 0.05 | >100 |
| 86 | 0.04 | >100 |
| 88 | 0.04 | >100 |
| Reference compound | 0.59 | >100 |

Reference compound: compound of Example 52 in an unexamined published Japanese patent application (kokai) No. 5-208946

4) Test on the ex vivo measurement of coagulation time in mice (intravenous administration).

Each drug dissolved in physiological saline was administered by single injection into caudal vein of each of male ICR mice (20–30 g, purchased from SLC) which have been abstained from food for 12 hours or more and, 1 minute thereafter and under diethyl ether anesthesia, 0.6 ml of blood was collected from the aorta with $\frac{1}{10}$ volume of 3.8% sodium citrate and centrifuged at 3,000 rpm for 10 minutes to separate blood plasma. Using the resulting blood plasma, extrinsic blood coagulation time (PT) and intrinsic blood coagulation time (APTT) were measured in accordance with the following methods a) and b).

a) Extrinsic blood coagulation time (PT)

Tissue thromboplastin (54 mg/vial, freeze-dried preparation, manufactured by Ortho) was dissolved in 2.5 ml of distilled water and pre-incubated at 3.7° C. A 50 $\mu$l portion of the aforementioned blood plasma was incubated at 37° C. for 1 minute and then mixed with 50 $\mu$l of the just described thromboplastin solution to measure blood coagulation time. KC4A manufactured by Amelung was used for the measurement of blood coagulation time. Blood coagulation time when physiological saline was administered instead of the drug was used as a control, and the drug activity was shown as a relative value to the control which was defined as 1.

b) Intrinsic blood coagulation time (APTT)

Blood coagulation time was measured by incubating 50 $\mu$l of activated thrombofacs (manufactured by Ortho) and 50 $\mu$l of the aforementioned blood plasma at 37° C. and then adding 50 $\mu$l of 20 mM $CaCl_2$ solution which has been pre-incubated at 37° C. KC4A manufactured by Amelung was used for the measurement of blood coagulation time. Blood coagulation time when physiological saline was administered instead of the drug was used as a control, and the drug activity was shown as a relative value to the control which was defined as 1. In this case, dose dependency of and periodical changes in the anticoagulation action were also examined by changing the administration dose or the blood collection time.

As the results of this test, excellent blood coagulation time extending action was observed by intravenous administration of the compound of the present invention.

5) Test on the ex vivo measurement of coagulation time in mice (oral administration).

The procedure of the above test 4) was repeated except that forced oral administration was carried out using an oral sound, instead of the single injection into caudal vein carried out in the test 4), and blood was collected 30 minutes thereafter.

As the results of this test, the blood coagulation time extending action was observed also by the oral administration of the compound of the present invention.

The pharmaceutical composition which contains one or two or more of the compounds of the present invention represented by the general formula (I) or pharmaceutically acceptable salts thereof as the active ingredient is prepared into tablets, powders, fine granules, granules, capsules, pills, solutions, injections, suppositories, ointments, adhesive preparations and the like using commonly used pharmaceutical carriers, fillers and other additives and administered orally or parenterally.

Clinical dose of the compound of the present invention in human is optionally decided by taking into consideration symptoms, body weight, age, sex and the like of each patient to be treated, but is usually 0.1 to 500 mg by oral administration, or 0.01 to 100 mg by parenteral administration, per day per adult, and the daily dose is divided into 1 to several doses per day. Since the dose varies under various conditions, a smaller dose than the above range may be sufficient in some cases.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, metasilicic acid or magnesium aluminate. In the usual way, the composition may contain additives other than the inert diluent, such as a lubricant (e.g., magnesium stearate), a disintegrating agent (e.g., calcium cellulose glycolate), a stabilizing agent (e.g., lactose) and a solubilizing or solubilization-assisting agent (e.g., glutamic acid and aspartic acid). If necessary, tablets or pills may be coated with a film of a gastric or enteric substance such as sucrose, gelatin, hydroxypropylcellulose, hydroxypropylmethylcellulose phthalate or the like. The liquid composition for oral administration includes pharmaceutically acceptable emulsions, solutions, suspensions, syrups, elixirs and the like and contains a commonly used inert diluent such as purified water or ethyl alcohol. In addition to the inert diluent, this composition may also contain auxiliary agents such as a solubilizing or solubilization assisting agent, a moistening agent, a suspending agent and the like, as well as sweeteners, flavors, aromas and antiseptics. The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, a plant oil (e.g., olive oil), an alcohol (e.g., ethyl alcohol), polysorbate 80 (trade name) and the like. Such a composition may further contain additive agents such as an isotonic agent, an antiseptic, a moistening agent, an emulsifying agent, a dispersing agent, a stabilizing agent (e.g., lactose) and a solubilizing or solubilization assisting agent. These compositions are sterilized by filtration through a bacteria retaining filter, blending of a germicide or irradiation. Alternatively, they may be used by firstly making into sterile solid compositions and dissolving them in sterile water or a sterile solvent for injection prior to their use. When the compound of the present invention has low solubility, it may be subjected to a solubilization treatment. The solubilization treatment may be carried out by known methods which can be applied to pharmaceutical preparations, such as a method in which surface active agents (polyoxyethylene hardened castor oils, polyoxyethylene sorbitan higher fatty acid esters, polyoxyethylene polyoxypropylene glycols, sucrose fatty acid esters and the like) are added, and a method in which a drug is formed into solid dispersion together with a solubilizing agent such as a polymer (e.g., a water soluble high polymer such as hydroxypropylmethylcellulose (HPMC), polyvinyl pyrrolidone (PVP), and polyethylene glycol (PEG), or an enteric polymer such as carboxymethylethylcellulose (CMEC), hydroxypropylmethylcellulose phthalate (HPMCP), and methyl methacrylate-methacrylic acid copolymer (Eudragit L, S, trade name, manufactured by Rohm & Haas)). In addition, as occasion demands, a method in which a drug is made into a soluble salt or a method in which an inclusion compound is formed using cyclodextrin or the like may also be employed. The solubilization means can be optionally changed depending on each drug of interest [*Saikin no seizaigijyutu to sono oyo* (Recent Pharmaceutical Technology and Application), I. Utsumi et al., *Iyaku Journal,* 157–159 (1983) and *Yakugaku Monograph* No. 1, Bioavailability", K. Nagai et al., published by Soft Science, 78–82 (1988)]. Of the above techniques, a method in which solubility of a drug is improved by forming its solid dispersion with a solubilizing agent (an unexamined published Japanese patent application (kokai) No. 56-49314, FR 2460667) may be employed preferably.

BEST MODE OF CARRYING OUT THE INVENTION

The following illustratively describes production method of the compounds of the present invention with reference to production examples of the compounds of the present invention. In this connection, since novel compounds are included in the starting compounds for the compounds of the present invention, production methods of these compounds are also described as reference examples.

REFERENCE EXAMPLE 1

Silver tetrafluoroborate (1,168 mg) was suspended in 6 ml of dimethyl sulfoxide, 1,230 mg of 7-Bromomethyl-2-naphthalenecarbonitrile was added to the suspension, and the mixture was stirred at room temperature for 14 hours. The reaction solution was filtered, water was added to the mother liquid, and the mixture was extracted with ethyl acetate. The extract was washed with brine, dried over anhydrous sodium sulfate, and then evaporated. The resulting residue was purified by silica gel column chromatography using a mixture of hexane and ethyl acetate as the eluent to give 543 mg of 7-formyl-2-naphthalenecarbonitrile in the form of white solid.

Nuclear magnetic resonance spectrum (CDCl$_3$, TMS internal standard) δ: 7.78 (1H, dd, J=1.2, 8.5 Hz), 8.01 (1H, d, J=8.5 Hz), 8.02 (1H, d, J=8.5 Hz), 8.13 (1H, dd, J=1.2, 8.5 Hz), 8.40 (2H, s), 10.21 (1H, s).

REFERENCE EXAMPLE 2

7-Formyl-2-naphthalenecarbonitrile obtained in Reference Example 1 (849 mg) and 1,370 mg of 4-[(1-t-butoxycarbonyl-4-piperidyl)oxy]aniline were dissolved in 10 ml of dichloromethane and 2.7 ml of acetic acid, 1,290 mg of sodium triacetoxyborohydride was added to the solution, and the mixture was stirred at room temperature for 45 minutes. The reaction solution was washed with 2M potassium carbonate, water and 10% citric acid aqueous solution in that order, dried over sodium sulfate, and then evaporated. By recrystallizing the resulting residue from methanol, 1,698 mg of 7-[[4-[(1-t-butoxycarbonyl-4-piperidyl)oxy]anilino]methyl]-2-naphthalenecarbonitrile was obtained.

Mass spectrometry data (m/z): 457 (M)$^+$

Nuclear magnetic resonance spectrum (CDCl$_3$, TMS internal standard) δ: 1.46 (9H, s), 1.63–1.74 (2H, m), 1.80–1.92 (2H, m), 3.21–3.30 (2H, m), 3.65–3.77 (2H, m), 4.00 (1H, bs), 4.21–4.28 (1H, m), 4.49 (1H, s), 6.59 (2H, d, J=8.8 Hz), 6.79 (2H, d, J=8.8 Hz), 7.59 (1H, d, J=8.3 Hz), 7.66 (1H, d, J=8.8 Hz), 7.84–7.92 (3H, m), 8.19 (1H, s).

REFERENCE EXAMPLE 3

7-[[4-[(1-t-Butoxycarbonyl-4-piperidyl)oxy]anilino]methyl]-2-naphthalenecarbonitrile obtained in Reference Example 2 (150 mg) was dissolved in 1 ml of pyridine, 268 mg of acetic anhydride and 10 mg of 4-dimethylaminopyridine were added to the solution, and the mixture was stirred at room temperature for 15 hours. Ethyl acetate was added to the reaction solution. The mixture was washed with 10% citric acid aqueous solution and saturated sodium bicarbonate aqueous solution in that order, dried over anhydrous sodium sulfate, and then evaporated. By recrystallizing the resulting residue from ethanol, 139 mg of N-[4-[(1-t-butoxycarbonyl-4-piperidyl)oxy]phenyl]-N-[(7-cyano-2-naphthyl)methyl]acetamide was obtained.

Mass spectrometry data (m/z): 500 (M+1)$^+$

Nuclear magnetic resonance spectrum (CDCl$_3$, TMS internal standard) δ: 1.46 (9H, s), 1.67–1.77 (2H, m), 1.85–1.97 (5H, m), 3.27–3.36 (2H, m), 3.63–3.76 (2H, m), 4.37–4.45 (1H, m), 5.02 (2H, s), 6.81 (2H, d, J=8.8 Hz), 6.88 (2H, d, J=8.8 Hz), 7.56–7.65 (3H, m), 7.83 (1H, d, J=8.3 Hz), 7.89 (1H, d, J=8.3 Hz), 8.13 (1H, s).

REFERENCE EXAMPLE 4

7-[[4-[(1-t-Butoxycarbonyl-4-piperidyl)oxy]anilino]methyl]-2-naphthalenecarbonitrile obtained in Reference Example 2 (200 mg) was dissolved in 2 ml of dichloromethane, 299 mg of ethyl chloroglyoxylate and 266 mg of triethylamine were added to the solution, and the mixture was stirred at room temperature for 15 hours. Ethyl acetate was added to the reaction solution. The mixture was washed with 10% citric acid aqueous solution and saturated sodium bicarbonate aqueous solution in that order, dried over anhydrous sodium sulfate, and then evaporated. The resulting residue was purified by silica gel column chromatography using hexane:ethyl acetate (8:2) as the eluent to give 241 mg of ethyl N-[4-[(1-t-butoxycarbonyl-4-piperidyl)oxy]phenyl]-N-[(7-cyano-2-naphthyl)methyl]oxamate.

Mass spectrometry data (m/z): 557 (M)$^+$.

Nuclear magnetic resonance spectrum (CDCl$_3$, TMS internal standard) δ: 1.01 (3H, t, J=7.1 Hz), 1.46 (9H, s), 1.63–1.75 (2H, m), 1.82–1.94 (2H, m), 3.25–3.36 (2H, m), 4.04 (2H, q, J=7.1 Hz), 4.35–4.45 (1H, m), 5.07 (2H, s), 6.78 (2H, d, J=8.8 Hz), 6.97 (2H, d, J=8.8 Hz), 7.58–7.63 (2H, m), 7.68 (1H, s), 7.86 (1H, d, J=8.3 Hz), 7.90 (1H, d, J=8.8 Hz), 8.15 (1H, s).

The following compounds of Reference Examples 5 to 13 were obtained in the same manner as described in Reference Example 4.

REFERENCE EXAMPLE 5

N-[4-[(1-t-Butoxycarbonyl-4-piperidyl)oxy]phenyl]-N-[(7-cyano-2-naphthyl)methyl]cyclopropanecarboxamide Starting compound: 7-[[4-[(1-t-butoxycarbonyl-4-piperidyl)oxy]anilino]methyl]-2-naphthalenecarbonitrile, cyclopropanecarbonyl chloride.

Mass spectrometry data (m/z): 526 (M+1)$^+$.

Nuclear magnetic resonance spectrum (CDCl$_3$, TMS internal standard) δ: 0.59–0.78 (2H, m), 0.94–1.13 (2H, m), 1.24–1.31 (1H, m), 1.46 (9H, s), 1.52–1.62 (2H, m), 1.65–1.92 (2H, m), 3.12–3.47 (2H, m), 3.54–3.74 (2H, m), 4.31–4.56 (1H, m), 5.04 (2H, s), 6.90–7.05 (4H, m), 7.51–7.98 (5H, m), 8.14 (1H, s).

REFERENCE EXAMPLE 6

N-[4-[(1-t-Butoxycarbonyl-4-piperidyl)oxy]phenyl]-N-[(7-cyano-2-naphthyl)methyl]benzamide Starting compound: 7-[[4-[(1-t-butoxycarbonyl-4-piperidyl)oxy]anilino]methyl]-2-naphthalenecarbonitrile, benzoyl chloride.

Mass spectrometry data (m/z): 562 (M+1)$^+$.

Nuclear magnetic resonance spectrum (CDCl$_3$, TMS internal standard) δ: 1.45 (9H, s), 1.54–1.84 (4H, m), 3.21–3.82 (4H, m), 4.22–4.41 (1H, m), 5.27 (2H, s), 6.53–6.94 (4H, m), 7.12–8.00 (10H, m), 8.18 (1H, s).

REFERENCE EXAMPLE 7

N-[4-[(1-t-Butoxycarbonyl-4-piperidyl)oxy]phenyl]-N-[(7-cyano-2-naphthyl)methyl]ethanecarboxamide Starting compound: 7-[[4-[(1-t-butoxycarbonyl-4-piperidyl)oxy]anilino]methyl]-2-naphthalenecarbonitrile, propanoyl chloride.

Mass spectrometry data (m/z): 514 (M+1)$^+$.

Nuclear magnetic resonance spectrum (CDCl$_3$, TMS internal standard) δ: 1.05 (3H, t, J=7.0 Hz), 1.46 (9H, s), 1.54–2.02 (6H, m), 3.01–3:38 (2H, m), 3.50–3.74 (2H, m), 4.34–4.51 (1H, m), 5.01 (2H, s), 6.91–7.12 (4H, m), 7.45–7.88 (5H, m), 8.14 (1H, s).

REFERENCE EXAMPLE 8

N-[4-[(1-t-Butoxycarbonyl-4-piperidyl)oxy]phenyl]-N-[(7-cyano-2-naphthyl)methyl]cyclohexanecarboxamide Starting compound: 7-[[4-[(1-t-butoxycarbonyl-4-piperidyl)oxy]anilino]methyl]-2-naphthalenecarbonitrile, cyclohexanecarbonyl chloride.

Mass spectrometry data (m/z): 568 (M+1)$^+$.

Nuclear magnetic resonance spectrum (CDCl$_3$, TMS internal standard) δ: 0.89–1.31 (5H, m), 1.46 (9H, s), 1.54–1.98 (10H, m), 3.17–3.48 (2H, m), 3.54–3.82 (2H, m), 4.34–4.51 (1H, m), 4.99 (2H, s), 6.82–7.07 (4H, m), 7.68–7.91 (5H, m), 8.12 (1H, s).

REFERENCE EXAMPLE 9

N-[4-[(1-t-Butoxycarbonyl-4-piperidyl)oxy]phenyl]-N-[(7-cyano-2-naphthyl)methyl]-1-naphthalenecarboxamide Starting compound: 7-[[4-[(1-t-butoxycarbonyl-4-piperidyl)oxy]anilino]methyl]-2-naphthalenecarbonitrile, 1-naphthalenecarbonyl chloride.

Mass spectrometry data (m/z): 612 (M+1)$^+$.

Nuclear magnetic resonance spectrum (CDCl$_3$, TMS internal standard) δ: 1.43 (9H, s), 1.54–1.79 (4H, m), 3.04–3.39 (2H, m), 3.42–3.70 (2H, m), 4.04–4.31 (1H, m), 5.34 (2H, s), 6.35–6.82 (4H, m), 7.15–8.13 (12H, m), 8.18 (1H, s).

REFERENCE EXAMPLE 10

N-[4-[(1-t-Butoxycarbonyl-4-piperidyl)oxy]phenyl]-N-[(7-cyano-2-naphthyl)methyl]-2-fluorobenzamide Starting compound: 7-[[4-[(1-t-butoxycarbonyl-4-piperidyl)oxy]anilino]methyl]-2-naphthalenecarbonitrile, 2-fluorobenzoyl chloride.

Mass spectrometry data (m/z): 580 (M+1)$^+$.

Nuclear magnetic resonance spectrum (CDCl$_3$, TMS internal standard) δ: 1.44 (9H, s), 1.57–1.94 (4H, m), 3.08–3.40 (2H, m), 3.49–3.80 (2H, m), 4.18–4.40 (1H, m), 5.28 (2H, s), 6.55–6.74 (2H, m), 6.80–7.48 (7H, m), 7.68–7.98 (4H, m), 8.14 (1H, s).

REFERENCE EXAMPLE 11

N-[4-[(1-t-Butoxycarbonyl-4-piperidyl)oxy]phenyl]-N-[(7-cyano-2-naphthyl)methyl]-3-methoxybenzamide Starting compound: 7-[[4-[(1-t-butoxycarbonyl-4-piperidyl)oxy]anilino]methyl]-2-naphthalenecarbonitrile, 3-methoxybenzoyl chloride.

Mass spectrometry data (m/z): 592 (M+1)$^+$.

Nuclear magnetic resonance spectrum (CDCl$_3$, TMS internal standard) δ: 1.45 (9H, s), 1.59–1.90 (4H, m), 3.07–3.45 (4H, m), 3.65 (3H, s), 4.21–4.48 (1H, m), 5.25 (2H, s), 6.58–7.10 (8H, m), 7.54–7.67 (1H, m), 7.69–7.95 (4H, m), 8.14 (1H, s).

REFERENCE EXAMPLE 12

N-[4-[(1-t-Butoxycarbonyl-4-piperidyl)oxy]phenyl]-N-[(7-cyano-2-naphthyl)methyl]-2-thiophenamide Starting compound: 7-[[4-[(1-t-butoxycarbonyl-4-piperidyl)oxy]anilino]methyl]-2-naphthalenecarbonitrile, thienoyl chloride.

Mass spectrometry data (m/z): 567 (M)$^+$.

Nuclear magnetic resonance spectrum (CDCl$_3$, TMS internal standard) δ: 1.45 (9H, s), 1.64–1.97 (4H, m), 3.14–3.48 (2H, m), 3.52–3.77=(2H, m), 4.35–4.60 (1H, m), 5.22 (2H, s), 6.74–7.18 (5H, m), 7.28–7.38 (1H, m), 7.52–7.69 (2H, m), 7.70–7.95 (4H, m), 8.12 (1H, s).

REFERENCE EXAMPLE 13

N-[4-[(1-t-Butoxycarbonyl-4-piperidyl)oxy]phenyl]-N-[(7-cyano-2-naphthyl)methyl]-3-pyridinecarboxamide Starting compound: 7-[[4-[(1-t-butoxycarbonyl-4-piperidyl)oxy]anilino]methyl]-2-naphthalenecarbonitrile, nicotinoyl chloride hydrochloride.

Mass spectrometry data (m/z): 563 (M+1)$^+$.

Nuclear magnetic resonance spectrum (CDCl$_3$, TMS internal standard) δ: 1.47 (9H, s), 1.65–1.94 (4H, m), 3.10–3.42 (2H, m), 3.51–3.87 (2H, m), 4.21–4.42 (1H, m), 5.32 (2H, s), 6.72–6.98 (2H, m), 7.62–7.79 (9H, m), 8.17 (1H, s), 8.41–8.67 (2H, m).

REFERENCE EXAMPLE 14

7-[[4-[(1-t-Butoxycarbonyl-4-piperidyl)oxy]anilino] methyl]-2-naphthalenecarbonitrile obtained in Reference Example 2 (150 mg) was dissolved in 2 ml of dichloromethane, 35 mg of ethyl isocyanate was added, and the mixture was stirred at room temperature for 15 hours. Then, 117 mg of ethyl isocyanate was added, the mixture was stirred at room temperature for 6 hours, and then the reaction solution was evaporated. The resulting residue was purified by silica gel column chromatography using hexane:ethyl acetate (65:35) as the eluent to give 154 mg of 1-[4-[(1-t-butoxycarbonyl-4-piperidyl)oxy]phenyl]-1-[(7-cyano-2-naphthyl)methyl]-3-ethylurea.

Mass spectrometry data (m/z): 528 (M)$^+$.

Nuclear magnetic resonance spectrum (CDCl$_3$, TMS internal standard) δ: 1.06 (3H, t, J=7.3 Hz), 1.46 (9H, s), 1.65–1.78 (2H, m), 1.82–1.95 (2H, m), 3.20–3.37 (4H, m), 3.62–3.75 (2H, m), 4.24 (1H, t, J=5.5 Hz), 4.36–4.44 (1H, m), 4.99 (2H, s), 6.83 (2H, d, J=7.0 Hz), 6.96 (2H, d, J=7.3 Hz), 7.57 (1H, d, J=8.5 Hz), 7.62–7.68 (2H, m), 7.83 (1H, d, J=8.5 Hz), 7.87 (1H, d, J=8.5 Hz), 8.13 (1H, s).

The following compound of Reference Example 15 was obtained in the same manner as described in Reference Example 14.

REFERENCE EXAMPLE 15

Ethyl 3-[4-[(1-t-butoxycarbonyl-4-piperidyl)oxy] phenyl]-3-[(7-cyano-2-naphthyl)methyl]ureido-1-acetate Starting compound: 7-[[4-[(1-t-butoxycarbonyl-4-piperidyl)oxy]anilino]methyl-2-naphthalenecarbonitrile, ethyl isocyanatoacetate.

Mass spectrometry data (m/z): 586 (M)$^+$.

Nuclear magnetic resonance spectrum (CDCl$_3$, TMS internal standard) δ: 1.27 (3H, t, J=7.3 Hz), 1.46 (9H, s), 1.65–1.80 (2H, m), 1.80–1.96 (2H, m), 3.25–3.38 (2H, m), 3.60–3.75 (2H, m), 4.00 (2H, d, J=5.9 Hz), 4.19 (2H, q, J=7.3 Hz), 4.35–4.45 (1H, m), 4.80 (1H, t, J=5.6 Hz), 5.01 (2H, s), 6.84 (2H, d, J=9.2 Hz), 7.05 (2H, d, J=8.8 Hz), 7.57 (1H, d, J=8.3 Hz), 7.64 (1H, d, J=8.3 Hz), 7.68 (1H, s), 7.83 (1H, d, J=8.3 Hz), 7.88 (1H, d, J=8.3 Hz), 8.15 (1H, s).

REFERENCE EXAMPLE 16

7-[[4-[(1-t-Butoxycarbonyl-4-piperidyl)oxy]anilino] methyl]-2-naphthalenecarbonitrile obtained in Reference Example 2 (150 mg) was dissolved in 2 ml of dimethylformamide, 178 mg of ethyl chloroformate and 271 mg of potassium carbonate were added to the solution, and the mixture was stirred at room temperature for 3.5 hours. The reaction solution was evaporated, and the resulting residue was purified by silica gel column chromatography using ethyl acetate:hexane (2:8) as the eluent to give 169 mg of ethyl N-[4-[(1-t-butoxycarbonyl-4-piperidyl)oxy]phenyl] -N-[(7-cyano-2-naphthyl)methyl]carbamate.

Mass spectrometry data (m/z): 529 (M)$^+$.

Nuclear magnetic resonance spectrum (CDCl$_3$, TMS internal standard) δ: 1.15–1.3 (3H, br), 1.46 (9H, s), 1.65–1.80 (2H, m), 1.80–1.95 (2H, m), 3.25–3.37 (2H, m), 3.60–3.75 (2H, m), 4.20 (2H, q, J=6.8 Hz), 4.35–4.45 (1H, m), 4.98 (2H, s), 6.79 (2H, d, J=8.8 Hz), 6.90–7.10 (2H, br), 7.58 (2H, d, J=9.5 Hz), 7.68 (1H, s), 7.84 (1H, d, J=8.3 Hz), 7.89 (1H, d, J=8.8 Hz), 8.15 (1H, s).

REFERENCE EXAMPLE 17

7-[[4-[(1-t-Butoxycarbonyl-4-piperidyl)oxy]anilino] methyl]-2-naphthalenecarbonitrile obtained in Reference Example 2 (150 mg) was dissolved in 4 ml of acetonitrile, 710 mg of ethyl thioisocyanate was added to the solution, and the mixture was heated under reflux for 4 days. The reaction solution was evaporated, and the resulting residue was purified by silica gel column chromatography using hexane:ethyl acetate (7:3) as the eluent to give 171 mg of 1-[4-[(1-t-butoxycarbonyl-4-piperidyl)oxy]phenyl]-1-[(7-cyano-2-naphthyl)methyl]-3-ethylthiourea.

Mass spectrometry data (m/z): 545 (M+1)$^+$.

Nuclear magnetic resonance spectrum (CDCl$_3$, TMS internal standard) δ: 1.11 (3H, t, J=7.1 Hz), 1.46 (9H, s), 1.66–1.76 (2H, m), 1.83–1.94 (2H, m), 3.25–3.35 (2H, m), 3.60–3.75 (4H, m), 4.36–4.44 (1H, m), 5.39 (1H, t, J=5.1 Hz), 5.65 (2H, s), 6.84 (2H, d, J=8.3 Hz), 6.90 (2H, d, J=8.3 Hz), 7.57 (2H, d, J=8.3 Hz), 7.69 (1H, s), 7.77–7.84 (2H, m), 7.88 (1H, d, J=8.3 Hz), 8.14 (1H, s).

REFERENCE EXAMPLE 18

7-[[4-[(1-t-Butoxycarbonyl-4-piperidyl)oxy]anilino] methyl]-2-naphthalenecarbonitrile obtained in Reference Example 2 (150 mg) was dissolved in 1 ml of pyridine, 211 mg of ethanesulfonyl chloride was added to the solution, and the mixture was stirred at 0° C. for 20 minutes and then at room temperature for 3 hours. Ethyl acetate was added to the reaction solution. The mixture was washed with 10% citric acid aqueous solution and brine in that order, dried over anhydrous sodium sulfate, and then evaporated. The resulting residue was purified by silica gel column chromatography using hexane:ethyl acetate (75:25) as the eluent to give 176 mg of N-[4-[(1-t-butoxycarbonyl-4-piperidyl)oxy] phenyl]-N-[(7-cyano-2-naphthyl)methyl] ethanesulfonamide.

Mass spectrometry data (m/z): 550 (M+1)$^+$.

Nuclear magnetic resonance spectrum (CDCl$_3$, TMS internal standard) δ: 1.43–1.50 (12H, m), 1.63–1.73 (2H, m), 1.80–1.91 (2H, m), 3.12 (2H, q, J=7.3 Hz), 3.25–3.36 (2H, m), 3.60–3.70 (2H, m), 4.33–4.41 (1H, m), 5.00 (2H, s), 6.78 (2H, d, J=6.8 Hz), 7.15 (2H, d, J=6.8 Hz), 7.58 (1H, d, J=8.5 Hz), 7.64 (1H, s), 7.69 (1H, d, J=8.5 Hz), 7.84 (1H, d, J=8.3 Hz), 7.88 (1H, d, J=8.3 Hz), 8.13 (1H, s).

The following compounds of Reference Examples 19 to 27 were obtained in the same manner as described in Reference Example 4.

REFERENCE EXAMPLE 19

N-[4-[(1-t-Butoxycarbonyl-4-piperidyl)oxy]phenyl]-N-[(7-cyano-2-naphthyl)methyl]-2-methoxybenzamide Starting compound: 7-[[4-[(1-t-butoxycarbonyl-4-piperidyl)oxy]anilino]methyl-2-naphthalenecarbonitrile, 2-methoxybenzoyl chloride.

Mass spectrometry data (m/z): 592 (M+1)$^+$.

Nuclear magnetic resonance spectrum (CDCl$_3$, TMS internal standard) δ: 1.44 (9H, s), 1.54–1.93 (4H, m), 3.02–3.58 (4H, m), 3.69 (3H, s), 4.14–4.39 (1H, m), 5.25

(2H, s), 6.44–7.36 (8H, m), 7.46–7.73 (1H, m), 7.75–8.00 (4H, m), 8.13 (1H, s).

REFERENCE EXAMPLE 20

N-[4-[(1-t-Butoxycarbonyl-4-piperidyl)oxy]phenyl]-N-[(7-cyano-2-naphthyl)methyl]-4-methoxybenzamide Starting compound: 7-[[4-[(1-t-butoxycarbonyl-4-piperidyl)oxy]anilino]methyl]-2-naphthalenecarbonitrile, 4-methoxybenzoyl chloride.

Mass spectrometry data (m/z): 592 (M+1)$^+$.

Nuclear magnetic resonance spectrum (CDCl$_3$, TMS internal standard) δ: 1.50 (9H, s), 1.67–1.95 (4H, m), 3.11–3.67 (4H, m), 3.76 (3H, s), 4.28–4.50 (1H, m), 5.32 (2H, s), 6.60–7.01 (8H, m), 7.77–7.90 (5H, m), 8.14 (1H, s).

REFERENCE EXAMPLE 21

N-[4-[(1-t-Butoxycarbonyl-4-piperidyl)oxy]phenyl]-N-[(7-cyano-2-naphthyl)methyl]-4-pyridinecarboxamide Starting compound: 7-[[4-[(1-t-butoxycarbonyl-4-piperidyl)oxy]anilino]methyl]-2-naphthalenecarbonitrile, nicotinoyl chloride hydrochloride.

Mass spectrometry data (m/z): 563 (M+1)$^+$.

Nuclear magnetic resonance spectrum (CDCl$_3$, TMS internal standard) δ: 1.48 (9H, s), 1.58–2.02 (4H, m), 3.07–3.82 (4H, m), 4.17–4.51 (1H, m), 5.29 (2H, s), 6.62–7.05 (4H, m), 7.12–7.41 (2H, m), 7.49–8.08 (6H, m), 8.17 (1H, s), 8.42–8.61 (2H, m).

REFERENCE EXAMPLE 22

N-[4-[(1-t-Butoxycarbonyl-4-piperidyl)oxy]phenyl]-N-[(7-cyano-2-naphthyl)methyl]-2-pyridinecarboxamide Starting compound: 7-[[4-[(1-t-butoxycarbonyl-4-piperidyl)oxy]anilino]methyl]-2-naphthalenecarbonitrile, picolinoyl chloride hydrochloride.

Mass spectrometry data (m/z): 563 (M+1)$^+$.

Nuclear magnetic resonance spectrum (CDCl$_3$, TMS internal standard) δ: 1.45 (9H, s), 1.61–1.94 (4H, m), 3.08–3.82 (4H, m), 4.21–4.47 (1H, m), 5.30 (2H, s), 6.54–7.03 (4H, m), 7.05–7.31 (2H, m), 7.43–7.72 (2H, m), 7.76–8.03 (4H, m), 8.15 (1H, s), 8.32–8.49 (2H, m).

REFERENCE EXAMPLE 23

N-[4-[(1-t-Butoxycarbonyl-4-piperidyl)oxy]phenyl]-N-[(7-cyano-2-naphthyl)methyl]-2-methoxyacetamide Starting compound: 7-[[4-[(1-t-butoxycarbonyl-4-piperidyl)oxy]anilino]methyl]-2-naphthalenecarbonitrile, methoxyacetyl chloride.

Mass spectrometry data (m/z): 530 (M+1)$^+$.

Nuclear magnetic resonance spectrum (CDCl$_3$, TMS internal standard) δ: 1.47 (9H, s), 1.64–2.07 (4H, m), 3.38 (3H, s), 3.45–3.77 (4H, m), 3.82 (2H, s), 4.31–4.58 (1H, m), 5.03 (2H, s), 6.79–6.98 (4H, m), 7.49–7.61 (1H, m), 7.77–8.00 (4H, m), 8.12 (1H, s).

REFERENCE EXAMPLE 24

Ethyl N-[4-[(1-t-butoxycarbonyl-4-piperidyl)oxy]phenyl]-N-[(7-cyano-2-naphthyl)methyl]malonamate Starting compound: 7-[(4-[(1-t-butoxycarbonyl-4-piperidyl)oxy]anilino]methyl]-2-naphthalenecarbonitrile, ethylmaloyl chloride.

Mass spectrometry data (m/z): 572 (M+1)$^+$.

Nuclear magnetic resonance spectrum (CDCl$_3$, TMS internal standard) δ: 1.28 (3H, t, J=8.1 Hz), 1.46 (9H, s), 1.62–1.97 (4H, m), 3.28 (2H, s), 3.36–3.84 (4H, m), 4.14 (2H, q, J=9.0 Hz), 4.32–4.56 (1H, s), 5.06 (2H, s), 6.67–7.06 (4H, m), 7.52–8.03 (5H, m), 8.15 (1H, s).

REFERENCE EXAMPLE 25

Ethyl N-[4-[(1-t-butoxycarbonyl-4-piperidyl)oxy]phenyl]-N-[(7-cyano-2-naphthyl)methyl]succinamate Starting compound: 7-[[4-[(1-t-butoxycarbonyl-4-piperidyl)oxy]anilino]methyl]-2-naphthalenecarbonitrile, ethylsuccinyl chloride.

Mass spectrometry data (m/z): 586 (M+1)$^+$.

Nuclear magnetic resonance spectrum (CDCl$_3$, TMS internal standard) δ: 1.26 (3H, t, J=8.7 Hz), 1.46 (9H, s), 1.64–1.97 (4H, m), 2.27–2.73 (4H, m), 3.15–3.88 (4H, m), 4.13 (2H, q, J=9.0 Hz), 4.32–4.54 (1H, m), 5.04 (2H, s), 6.72–7.07 (4H, m), 7.47–8.03 (5H, m), 8.17 (1H, s).

REFERENCE EXAMPLE 26

N-[4-[(1-t-Butoxycarbonyl-4-piperidyl)oxy]phenyl]-N-[(7-cyano-2-naphthyl)methyl]-2,6-difluorobenzamide Starting compound: 7-[[4-[(1-t-butoxycarbonyl-4-piperidyl)oxy]anilino]methyl]-2-naphthalenecarbonitrile, 2,6-difluorobenzoyl chloride.

Mass spectrometry data (m/z): 598 (M+1)$^+$.

Nuclear magnetic resonance spectrum (CDCl$_3$, TMS internal standard) δ: 1.44 (9H, s), 1.54–1.83 (4H, m), 3.05–3.80 (4H, m), 4.16–4.43 (1H, m), 5.23 (2H, s), 6.48–7.22 (7H, m), 7.46–8.01 (5H, m), 8.13 (1H, s).

REFERENCE EXAMPLE 27

N-[4-[(1-t-Butoxycarbonyl-4-piperidyl)oxy]phenyl]-N-[(7-cyano-2-naphthyl)methyl]-2-bromoacetamide Starting compound: 7-[[4-[(1-t-butoxycarbonyl-4-piperidyl)oxy]anilino]methyl]-2-naphthalenecarbonitrile, bromoacetyl bromide.

Mass spectrometry data (m/z): 578 (M)$^+$.

Nuclear magnetic resonance spectrum (CDCl$_3$, TMS internal standard) δ: 1.46 (9H, s), 1.64–2.00 (4H, m), 3.14–3.66 (4H, m), 3.73 (2H, s), 4.30–4.56 (1H, m), 5.04 (2H, s), 6.75–7.12 (4H, m), 7.46–7.79 (5H, m), 8.12 (1H, s).

REFERENCE EXAMPLE 28

N-[4-[(1-t-Butoxycarbonyl-4-piperidyl)oxy]phenyl]-N-[(7-cyano-2-naphthyl)methyl]-2-bromoacetamide obtained in Reference Example 27 (237 mg) was dissolved in 1 ml of methanol, 10 ml of 40% dimethylamine aqueous solution was added to the solution, and the mixture was stirred at 60° C. for 12 hours. The reaction solution was evaporated and chloroform was added to the resulting residue. The mixture was washed with water and brine in that order, dried over anhydrous sodium sulfate and then evaporated to give 247 mg of N-[4-[(1-t-butoxycarbonyl-4-piperidyl)oxy]phenyl]-N-[(7-cyano-2-naphthyl)methyl]-2-dimethylaminoacetamide.

Mass spectrometry data (m/z): 543 (M+1)$^+$.

Nuclear magnetic resonance spectrum (CDCl$_3$, TMS internal standard) δ: 1.46 (9H, s), 1.62–2.10 (4H, m), 2.28

(6H, s), 3.07–3.89 (4H, m), 4.30–4.55 (1H, m), 5.02 (2H, s), 6.75–6.98 (4H, m), 7.39–7.97 (5H, m), 8.27 (1H, s).

REFERENCE EXAMPLE 29

The compound of reference Example 29 was obtained in the same manner as described in Reference Example 14.

Ethyl N-[N-[4-[(1-t-butoxycarbonyl-4-piperidyl)oxy]phenyl]-N-[(7-cyano-2-naphthyl)methyl]carbamoyl]carbonate Starting compound: 7-[[4-[(1-t-butoxycarbonyl-4-piperidyl)oxy]anilino]methyl]-2-naphthalenecarbonitrile, ethoxycarbonyl isocyanate.

Mass spectrometry data (m/z): 573 (M+1)$^+$.

Nuclear magnetic resonance spectrum (CDCl$_3$, TMS internal standard) δ: 1.26 (3H, t, J=7.1 Hz), 1.47 (9H, s), 1.53–1.97 (4H, m), 3.17–3.88 (4H, m), 4.18 (2H, q, J=7.1 Hz), 4.33–4.56 (1H, m), 4.99 (2H, s), 6.81–7.08 (4H, m), 7.46–8.06 (5H, m), 8.13 (1H, s).

The following compounds of Reference Examples 30 to 44 were obtained in the same manner as described in Reference Example 18.

REFERENCE EXAMPLE 30

N-[4-[(1-t-Butoxycarbonyl-4-piperidyl)oxy]phenyl]-N-[(7-cyano-2-naphthyl)methyl]benzenesulfonamide Starting compound: 7-[[4-[(1-t-butoxycarbonyl-4-piperidyl)oxy]anilino]methyl]-2-naphthalenecarbonitrile, benzenesulfonyl chloride.

Mass spectrometry data (m/z): 597 (M)$^+$.

Nuclear magnetic resonance spectrum (CDCl$_3$, TMS internal standard) δ: 1.45 (9H, s), 1.60–1.70 (2H, m), 1.80–1.90 (2H, m), 3.23–3.33 (2H, m), 3.60–3.70 (2H, m), 4.30–4.38 (1H, m), 4.86 (2H, s), 6.69 (2H, d, J=8.8 Hz), 6.86 (2H, d, J=8.8 Hz), 7.48–7.73 (8H, m), 7.82 (1H, d, J=7.8 Hz), 7.86 (1H, d, J=8.3 Hz), 8.09 (1H, s).

REFERENCE EXAMPLE 31

N-[4-[(1-t-Butoxycarbonyl-4-piperidyl)oxy]phenyl]-N-[(7-cyano-2-naphthyl)methyl]methanesulfonamide Starting compound: 7-[[4-[(1-t-butoxycarbonyl-4-piperidyl)oxy]anilino]methyl]-2-naphthalenecarbonitrile, methanesulfonyl chloride.

Mass spectrometry data (m/z): 536 (M+1)$^+$.

Nuclear magnetic resonance spectrum (CDCl$_3$, TMS internal standard) δ: 1.45 (9H, s), 1.63–1.73 (2H, m), 1.80–1.90 (2H, m), 2.99 (3H, s), 3.25–3.35 (2H, m), 3.60–3.70 (2H, m), 4.34–4.40 (1H, m), 4.97 (2H, s), 6.80 (2H, d, J=8.8 Hz), 7.17 (2H, d, J=8.8 Hz), 7.59 (1H, dd, J=8.8, 1.5 Hz), 7.63–7.72 (2H, m), 7.85 (1H, d, J=8.3 Hz), 7.88 (1H, d, J=8.8 Hz), 8.13 (1H, s).

REFERENCE EXAMPLE 32

N-[4-[(1-t-Butoxycarbonyl-4-piperidyl)oxy]phenyl]-N-[(7-cyano-2-naphthyl)methyl]benzylsulfonamide Starting compound: 7-[[4-[(1-t-butoxycarbonyl-4-piperidyl)oxy]anilino]methyl]-2-naphthalenecarbonitrile, benzylsulfonyl chloride.

Mass spectrometry data (m/z): 611 (M)$^+$.

Nuclear magnetic resonance spectrum (CDCl$_3$, TMS internal standard) δ: 1.46 (9H, s), 1.63–1.74 (2H, m), 1.81–1.93 (2H, m), 3.25–3.36 (2H, m), 3.61–3.72 (2H, m), 4.33–4.41 (3H, m), 4.64 (2H, s), 6.77 (2H, d, J=8.8 Hz), 7.08 (2H, d, J=8.8 Hz), 7.41–7.59 (8H, m), 7.77 (1H, d, J=8.8 Hz), 7.84 (1H, d, J=8.2 Hz), 8.06 (1H, s).

REFERENCE EXAMPLE 33

N-[4-[(1-t-Butoxycarbonyl-4-piperidyl)oxy]phenyl]-N-[(7-cyano-2-naphthyl)methyl]propanesulfonamide Starting compound: 7-[[4-[(1-t-butoxycarbonyl-4-piperidyl)oxy]anilino]methyl]-2-naphthalenecarbonitrile, propanesulfonyl chloride.

Mass spectrometry data (m/z): 563 (M)$^+$.

Nuclear magnetic resonance spectrum (CDCl$_3$, TMS internal standard) δ: 1.08 (3H, t, J=7.3 Hz), 1.45 (9H, s), 1.63–1.73 (2H, m), 1.80–2.00 (4H, m), 3.02–3.09 (2H, m), 3.24–3.34 (2H, m), 3.59–3.69 (2H, m), 4.33–4.41 (1H, m), 4.98 (2H, s), 6.79 (2H, d, J=9.3 Hz), 7.15 (2H, d, J=9.3 Hz), 7.58 (1H, dd, J=8.3, 1.5 Hz), 7.64 (1H, s), 7.69 (1H, dd, J=8.8, 1.5 Hz), 7.84 (1H, d, J=8.3 Hz), 7.87 (1H, d, J=8.3 Hz), 8.12 (1H, s).

REFERENCE EXAMPLE 34

N-[4-[(1-t-Butoxycarbonyl-4-piperidyl)oxy]phenyl]-N-[(7-cyano-2-naphthyl)methyl]butanesulfonamide Starting compound: 7-[[4-[(1-t-butoxycarbonyl-4-piperidyl)oxy]anilino]methyl]-2-naphthalenecarbonitrile, 1-butanesulfonyl chloride.

Mass spectrometry data (m/z): 517 (M)$^+$.

Nuclear magnetic resonance spectrum (CDCl$_3$, TMS internal standard) δ: 0.95 (3H, t, J=7.1 Hz), 1.24–1.36 (2H, m), 1.45 (9H, s), 1.63–1.94 (6H, m), 2.94–3.85 (6H, m), 4.27–4.53 (1H, m), 5.02 (2H, s), 6.71–7.37 (4H, m), 7.42–7.96 (5H, m), 8.07 (1H, s).

REFERENCE EXAMPLE 35

N-[4-[(1-t-Butoxycarbonyl-4-piperidyl)oxy]phenyl]-N-[(7-cyano-2-naphthyl)methyl]trifluoromethanesulfonamide Starting compound: 7-[[4-[(1-t-butoxycarbonyl-4-piperazyl)oxy]anilino]methyl]-2-naphthalenecarbonitrile, trifluoromethanesulfonic anhydride.

Mass spectrometry data (m/z): 590 (M+1)$^+$.

Nuclear magnetic resonance spectrum (CDCl$_3$, TMS internal standard) δ: 1.45 (9H, s), 1.56–1.92 (4H, m), 3.11–3.82 (4H, m), 4.22–4.51 (1H, m), 5.02 (2H, s), 6.65–7.18 (4H, m), 7.46–7.97 (5H, m), 8.11 (1H, s).

REFERENCE EXAMPLE 36

N-[4-[(1-t-Butoxycarbonyl-4-piperidyl)oxy]phenyl]-N-[(7-cyano-2-naphthyl)methyl]isopropanesulfonamide Starting compound: 7-[[4-[(1-t-butoxycarbonyl-4-piperidyl)oxy]anilino]methyl]-2-naphthalenecarbonitrile, isopropylsulfonyl chloride.

Mass spectrometry data (m/z): 563 (M)$^+$.

Nuclear magnetic resonance spectrum (CDCl$_3$, TMS internal standard) δ: 1.45 (9H, s), 1.46 (6H, d, J=6.8 Hz), 1.59–1.93 (4H, m), 2.97–3.84 (5H, m), 4.20–4.52 (1H, m), 5.03 (2H, s), 6.64–7.26 (4H, m), 7.44–7.96 (5H, m), 8.08 (1H, s).

REFERENCE EXAMPLE 37

Ethyl N-[N-[4-[(1-t-butoxycarbonyl-4-piperidyl)oxy]phenyl]-N-[(7-cyano-2-naphthyl)methyl]sulfamoyl]carbamate Starting compound: 7-[[4-[(1-t-butoxycarbonyl-4-piperidyl)oxy]anilino]methyl-2-naphthalenecarbonitrile, ethyl(chlorosulfonyl)carbamate In this case, ethyl (chlorosulfonyl)carbamate was synthesized in the same manner as the case of t-butyl(chlorosulfonyl)carbamate described in Tetrahedron, 49(1), 65 (1993).

Mass spectrometry data (m/z): 608 (M)+.

Nuclear magnetic resonance spectrum (CDCl$_3$, TMS internal standard) δ: 1.37 (3H, t, J=7.1 Hz), 1.45 (9H, s), 1.62–1.74 (2H, m), 1.80–1.92 (2H, m), 3.25–3.34 (2H, m), 3.60–3.71 (2H, m), 4.29–4.42 (3H, m), 5.21 (2H, s), 6.80 (2H, d, J=8.8 Hz), 7.08–7.20 (3H, m), 7.58 (1H, dd, J=8.3, 1.5 Hz), 7.62–7.69 (2H, m), 7.84 (1H, d, J=8.8 Hz), 7.88 (1H, d, J=8.3 Hz), 8.13 (1H, s).

REFERENCE EXAMPLE 38

N-[4-[(1-Butoxycarbonyl-4-piperidyl)oxy]phenyl]-N-[(7-cyano-2-naphthyl)methyl]-4-nitrobenzenesulfonamide Starting compound: 7-[[4-[(1-t-butoxycarbonyl-4-piperadyl)oxy]anilino]methyl]-2-naphthalenecarbonitrile, 4-nitrobenzenesulfonyl chloride.

Mass spectrometry data (m/z): 642 (M)+.

Nuclear magnetic resonance spectrum (CDCl$_3$, TMS internal standard) δ: 1.45 (9H, s), 1.62–1.94 (4H, m), 3.07–3.83 (4H, m), 4.21–4.48 (1H, m), 4.90 (2H, s), 6.61–6.92 (4H, m), 7.50–8.04 (7H, m), 8.10 (1H, s), 8.31 (1H, s), 8.41 (1H, s).

REFERENCE EXAMPLE 39

4-[N-[4-[(1-t-Butoxycarbonyl-4-piperidyl)oxy]phenyl]-N-[(7-cyano-2-naphthyl)methyl]sulfamoyl]benzoic acid Starting compound: 7-[[4-[(1-t-butoxycarbonyl-4-piperidyl)oxy]anilino]methyl-2-naphthalenecarbonitrile, 4-(chlorosulfonyl)benzoic acid.

Mass spectrometry data (m/z): 641 (M)+.

Nuclear magnetic resonance spectrum (DMSO-d$_6$, TMS internal standard) δ: 1.32–1.47 (11H, m), 7.5–8.6 (2H, m), 3.0–3.15 (2H, m), 3.55–3.66 (2H, m), 4.37–4.47 (1H, m), 4.97 (2H, s), 6.80 (2H, d, J=8.8 Hz), 6.96 (2H, d, J=9.3 Hz), 7.67 (1H, d, J=8.8 Hz), 7.74 (1H, dd, J=1.5, 8.3 Hz), 7.81 (2H, d, J=8.3 Hz), 7.89 (1H, s), 8.00 (1H, d, J=8.3 Hz), 8.07 (1H, d, J=8.8 Hz), 8.15 (2H, d, J=8.3 Hz), 8.52 (1H, s), 13.52 (1H, bs).

REFERENCE EXAMPLE 40

3-[N-[4-[(1-t-Butoxycarbonyl-4-piperidyl)oxy]phenyl]-N-[(7-cyano-2-naphthyl)methyl]sulfamoyl]benzoic acid Starting compound: 7-[[4-[(1-t-butoxycarbonyl-4-piperidyl)oxy]anilino]methyl-2-naphthalenecarbonitrile, 3-(chlorosulfonyl)benzoic acid.

Mass spectrometry data (m/z): 640 (M−1)+.

Nuclear magnetic resonance spectrum (DMSO-d$_6$, TMS internal standard) δ: 1.32–1.46 (11H, m), 1.72–1.85 (2H, m), 3.02–3.15 (2H, m), 3.52–3.66 (2H, m), 4.37–4.47 (1H, m), 4.96 (2H, s), 6.81 (2H, d, J=8.8 Hz), 6.97 (2H, d, J=8.8 Hz), 7.66 (1H, d, J=8.3 Hz), 7.70–7.83 (2H, m), 7.90 (1H, s), 7.92–8.09 (4H, m), 8.27 (1H, d, J=7.8 Hz), 8.51 (1H, s), 13.51 (1H, s).

REFERENCE EXAMPLE 41

Methyl 2-[N-[4-[(1-t-butoxycarbonyl-4-piperidyl)oxy]phenyl]-N-[(7-cyano-2-naphthyl)methyl]sulfamoyl]benzoate Starting compound: 7-[[4-[(1-t-butoxycarbonyl-4-piperidyl)oxy]anilino]methyl-2-naphthalenecarbonitrile, methyl-2-(chlorosulfonyl)benzoate.

Mass spectrometry data (m/z): 655 (M)+.

Nuclear magnetic resonance spectrum (CDCl$_3$, TMS internal standard) δ: 1.55 (9H, s), 1.59–1.70 (2H, m), 1.80–1.89 (2H, m), 3.21–3.31 (2H, m), 3.30–3.40 (2H, m), 3.96 (3H, s), 4.30–4.38 (1H, m), 5.02 (2H, s), 6.68 (2H, d, J=9.2 Hz), 6.95 (2H, d, J=9.2 Hz), 7.40–7.50 (2H, m), 7.52–7.62 (3H, m), 7.65 (1H, s), 7.70 (1H, d, J=8.5 Hz), 7.83 (1H, d, J=8.6 Hz), 7.87 (1H, d, J=8.6 Hz), 8.11 (1H, s).

REFERENCE EXAMPLE 42 t-Butyl N-[N-[4-[(1-t-butoxycarbonyl-4-piperidyl)oxy]phenyl]-N-[(7-cyano-2-naphthyl)methyl]sulfamoyl]carbamate Starting compound: 7-[[4-[(1-t-butoxycarbonyl-4-piperidyl)oxy]anilino]methyl]-2-naphthalenecarbonitrile, t-butyl(chlorosulfonyl)carbamate In this connection, the method for the synthesis of t-butyl(chlorosulfonyl)carbamate is described in Tetrahedron, 49(1), 65 (1993).

Mass spectrometry data (m/z): 636 (M)+.

Nuclear magnetic resonance spectrum (CDCl$_3$, TMS internal standard) δ: 1.45 (9H, s), 1.57 (9H, s), 1.63–1.73 (2H, m), 1.80–1.91 (2H, m), 3.25–3.35 (2H, m), 3.60–3.70 (2H, m), 4.33–4.43 (1H, m), 5.21 (2H, s), 6.80 (2H, d, J=9.3 Hz), 7.00 (1H, bs), 7.18 (2H, d, J=8.8 Hz), 7.58 (1H, dd, J=1.7, 8.5 Hz), 7.62–7.70 (2H, m), 7.84 (1H, d, J=6.6 Hz), 7.87 (1H, d, J=8.3 Hz), 8.13 (1H, s).

REFERENCE EXAMPLE 43

Ethyl N-[4-[(1-t-butoxycarbonyl-4-piperidyl)oxy]phenyl]-N-[(7-cyano-2-naphthyl)methyl]sulfamoyl]acetate Starting compound: 7-[[4-[(1-t-butoxycarbonyl-4-piperadyl)oxy]anilino]methyl]-2-naphthalenecarbonitrile, ethyl(chlorosulfonyl)acetate. In this connection, method for the synthesis of ethyl(chlorosulfonyl)acetate is described in Synthetic Letters, 321, 1975.

Mass spectrometry data (m/z): 608 (M+1)+.

Nuclear magnetic resonance spectrum (CDCl$_3$, TMS internal standard) δ: 1.34–1.55 (12H, m), 1.57–1.95 (4H, m), 3.12–3.74 (4H, m), 4.03 (2H, s), 4.17–4.52 (5H, m), 5.03 (2H, s), 6.66–6.91 (4H, m), 7.27–7.96 (5H, m), 8.11 (1H, s).

REFERENCE EXAMPLE 44

Ethyl 3-[N-[4-[(1-t-butoxycarbonyl-4-piperidyl)oxy]phenyl]-N-[(7-cyano-2-naphthyl)methyl]sulfamoyl]propionate Starting compound: 7-[[4-[(1-t-butoxycarbonyl-4-piperadyl)oxy]anilino]methyl]-2-naphthalenecarbonitrile, ethyl 3-(chlorosulfonyl)propionate (Synthesized by a method similar to the case of ethyl(chlorosulfonyl)acetate.).

Mass spectrometry data (m/z): 622 (M+1)+.

Nuclear magnetic resonance spectrum (CDCl$_3$, TMS internal standard) δ: 1.28 (3H, t, J=7.3 Hz), 1.45 (9H, s), 1.56–1.94 (4H, m), 2.71–3.08 (2H, m), 3.00–3.82 (6H, m), 4.19 (2H, q, J=7.1 Hz), 4.35–4.53 (1H, m), 4.96 (2H, s), 6.71–7.24 (4H, m), 7.48–7.94 (5H, m), 8.12 (1H, s).

REFERENCE EXAMPLE 45 t-Butyl N-[N-[4-[(1-t-butoxycarbonyl-4-piperidyl)oxy]phenyl]-N-[(7-cyano-2-naphthyl)methyl]sulfamoyl]carbamate obtained in Reference Example 42 (172 mg) was dissolved in 0.7 ml of tetrahydrofuran, 139 mg of triphenylphosphine, 32 μl of methanol and 83 μl of diethyl azodicarboxylate was added to the solution at 0° C., and then the mixture was stirred at room temperature for 40 minutes. The reaction solution was evaporated, and the resulting residue was purified by silica gel column chromatography using hexane:ethyl acetate (85:15) as the eluent to give 153 mg of t-butyl N-[N-[4-[(1-t-butoxycarbonyl-4-piperidyl)oxy]phenyl]-N-[(7-cyano-2-naphthyl)methyl]sulfamoyl]-N-methylcarbamate.

Mass spectrometry data (m/z): 650 (M)+.

Nuclear magnetic resonance spectrum (CDCl$_3$, TMS internal standard) δ: 1.45 (9H, s), 1.57–1.73 (11H, m), 1.80–1.92 (2H, m), 2.93 (3H, s), 3.24–3.35 (2H, m), 3.60–3.72 (2H, m), 4.33–4.42 (1H, m), 5.19 (2H, s), 6.79 (2H, d, J=9.3 Hz), 7.15 (2H, d, J=8.8 Hz), 7.57 (1H, dd, J=1.5, 8.3 Hz), 7.64–7.70 (2H, m), 7.84 (1H, d, J=8.3 Hz), 7.87 (1H, d, J=8.3 Hz), 8.13 (1H, s).

REFERENCE EXAMPLE 46

7-Formyl-2-naphthalenecarbonitrile obtained in Reference Example 1 (3.0 g) was dissolved in 50 ml of acetone. The solution was cooled to 0° C. with stirring, and a solution prepared by dissolving 10 g of chromium oxide (IV) in 11 ml of concentrated sulfuric acid and 50 ml of water was added until the mixture becomes orange yellow. The reaction solution was stirred at 0° C. for 90 minutes and then at room temperature for 45 minutes, followed by the addition of 2 ml of isopropyl alcohol. The reaction solution was evaporated, water was added to the resulting residue, and the mixture was extracted with ethyl acetate. The ethyl acetate layer was extracted with saturated sodium bicarbonate aqueous solution, the saturated sodium bicarbonate layer was adjusted to pH 1 by adding concentrated sulfuric acid, and the thus precipitated solid matter was collected by filtration to give 1.94 g of 7-cyano-2-naphthalenecarboxylic acid.

Mass spectrometry data (m/z): 197 (M)+.

Nuclear magnetic resonance spectrum (DMSO, TMS internal standard) δ: 7.93 (1H, dd, J=1.2, 8.5 Hz), 8.13–8.23 (3H, m), 8.75 (1H, s), 8.80 (1H, s), 13.33 (1H, s).

REFERENCE EXAMPLE 47

7-Cyano-2-naphthalenecarboxylic acid obtained in Reference Example 46 (1.5 g) and 2.2 g of 4-[(1-t-butoxycarbonyl- 4-]piperidyl)oxy]aniline were dissolved in 30 ml of dimethylformamide, 1.75 g of 1-ethyl-3-(3-dimethylaminopropyl)carbodiimide hydrochloride, 1.03 g of 1-hydroxybenzotriazole and 1.26 ml of triethylamine were added to the solution, and the mixture was stirred at room temperature for 1 day. The reaction solution was filtered and the filtrate was evaporated. The resulting residue was recrystallized from ethanol to give 2.7 g of N-[4-[(1-t-butoxycarbonyl-4-piperidyl)oxy]phenyl]-7-cyano-2-naphthalenecarboxamide.

Mass spectrometry data (m/z): 471 (M)+.

Nuclear magnetic resonance spectrum (CDCl, TMS internal standard) δ: 1.48 (9H, s), 1.70–1.80 (2H, m), 1.85–1.98 (2H, m), 3.28–3.40 (2H, m), 3.65–3.7 (2H, m), 4.41–4.50 (1H, m), 6.94 (2H, d, J=8.8 Hz), 7.59 (2H, d, J=8.8 Hz), 7.71 (1H, d, J=9.0 Hz), 7.94–8.03 (2H, m), 8.06–8.15 (2H, m), 8.29 (1H, s), 8.41 (1H, s).

REFERENCE EXAMPLE 48

N-[4-[(1-t-Butoxycarbonyl-4-piperidyl)oxy]phenyl]-7-cyano-2-naphthalenecarboxamide obtained in Reference Example 47 (200 mg) was dissolved in 4 ml of DMF, 52 mg of sodium hydride (content 60%) was added to the solution, and the mixture was stirred at room temperature for 20 minutes. While stirring at 0° C., 1 ml dimethylformamide solution of 100 ml methanesulfonyl chloride was added dropwise to the reaction solution, followed by 1 day of stirring at room temperature. The reaction solution was evaporated and ethyl acetate was added to the resulting residue. The mixture was washed with saturated sodium bicarbonate aqueous solution and 10% citric acid aqueous solution in that order, dried over anhydrous sodium sulfate, and then evaporated. The resulting residue was purified by silica gel column chromatography using hexane:ethyl acetate (8:2–7:3) as the eluent to give 143 mg of N-[4-[(1-t-butoxycarbonyl-4-piperidyl)oxy]phenyl]-7-cyano-N-methylsulfonyl-2-naphthalenecarboxamide.

Mass spectrometry data (m/z): 550 (M+1)+.

Nuclear magnetic resonance spectrum (CDCl$_3$, TMS internal standard) δ: 1.45 (9H, s), 1.59–1.71 (2H, m), 1.79–1.89 (2H, m), 3.23–3.33 (2H, m), 3.48 (3H, s), 3.58–3.69 (2H, m), 4.33–4.41 (1H, m), 6.80 (2H, d, J=8.8 Hz), 7.21 (2H, d, J=8.8 Hz), 7.63–7.77 (3H, m), 7.86 (1H, d, J=8.3 Hz), 8.12 (2H, s).

The following compound of Reference Example 49 was obtained in the same manner as described in Reference Example 45.

REFERENCE EXAMPLE 49

Ethyl N-[N-[4-[(1-t-butoxycarbonyl-4-piperidyl)oxy]phenyl]-N-[(7-cyano-2-naphthyl)methyl]sulfamoyl]-N-methylcarbamate Starting compound: Ethyl N-[N-[[4-[(1-t-butoxycarbonyl-4-piperidyl)oxy]phenyl]-N-[(7-cyano-2-naphthyl)methyl]sulfamoyl]carbamate, methanol.

Mass spectrometry data (m/z): 622 (M)+.

Nuclear magnetic resonance spectrum (DMSO-d$_6$, TMS internal standard) δ: 1.39–1.50 (12H, m), 1.61–1.74 (2H, m), 1.80–1.91 (2H, m), 3.01 (3H, s), 3.23–3.33 (2H, m), 3.61–3.71 (2H, m), 4.33–4.45 (3H, m), 5.18 (2H, s), 6.79 (2H, d, J=9.3 Hz), 7.11 (2H, d, J=8.8 Hz), 7.58 (1H, dd, J=1.5, 8.8 Hz), 7.62–7.70 (2H, m), 7.85 (1H, d, J=8.3 Hz), 7.88 (1H, d, J=8.3 Hz), 8.13 (1H, s).

REFERENCE EXAMPLE 50

Ethyl N-[N-[4-[(1-t-butoxycarbonyl-4-piperidyl)oxy]phenyl]-N-[(7-cyano-2-naphthyl)methyl]sulfamoyl]carbamate (1 g) was dissolved in 10 ml of dimethylformamide, 376 mg of methyl bromoacetate and 339 mg of potassium carbonate were added to the solution, and the mixture was stirred at room temperature for 15 hours. The reaction solution was evaporated, water was added, and the mixture was extracted with chloroform. The extract was dried over anhydrous sodium sulfate and then evaporated. The resulting residue was purified by silica gel column chromatography using hexane:ethyl acetate (8:2) as the eluent to give 1.097 g of methyl N-[N-[4-[(1-t-butoxycarbonyl-4-piperidyl)oxy]phenyl]-N-[(7-cyano-2-naphthyl)methyl]sulfamoyl]-N-ethoxycarbonylglycinate.

Mass spectrometry data (m/z): 680 (M)$^+$.

Nuclear magnetic resonance spectrum (CDCl$_3$, TMS internal standard) δ: 1.38 (3H, t, J=7.1 Hz), 1.45 (9H, s), 1.62–1.74 (2H, m), 1.80–1.91 (2H, m), 3.24–3.35 (2H, m), 3.60–3.71 (5H, m), 4.21 (2H, s), 4.34–4.44 (3H, m), 5.19 (2H, m), 6.78 (2H, d, J=8.8 Hz), 7.13 (2H, d, J=8.8 Hz), 7.58 (1H, d, J=8.5 Hz), 7.62–7.69 (2H, m), 7.84 (1H, d, J=8.8 Hz), 7.88 (1H, d, J=8.8 Hz), 8.12 (1H, s).

The following compound of Reference Example 51 was obtained in the same manner as described in Reference Example 50.

REFERENCE EXAMPLE 51

Ethyl N-[N-[4-[(1-t-butoxycarbonyl-4-piperidyl)oxy]phenyl]-N-[(7-cyano-2-naphthyl)methyl]sulfamoyl]-N-t-butoxycarbonylglycinate Starting compound: t-butyl N-[N-[4-[(1-t-butoxycarbonyl-4-piperidyl)oxy]phenyl]-N-[(7-cyano-2-naphthyl)methyl]sulfamoyl]carbamate, ethyl bromoacetate.

Mass spectrometry data (m/z): 722 (M)$^+$.

Nuclear magnetic resonance spectrum (CDCl$_3$, TMS internal standard) δ: 1.24 (3H, t, J=7.1 Hz), 1.45 (9H, s), 1.58 (9H, s), 1.60–1.76 (2H, m), 1.80–1.92 (2H, m), 3.24–3.35 (2H, m), 3.60–3.71 (2H, m), 4.08–4.20 (4H, m), 4.32–4.42 (1H, m), 5.19 (2H, s), 6.77 (2H, d, J=8.8 Hz), 7.15 (2H, d, J=8.8 Hz), 7.57 (1H, d, J=8.3 Hz), 7.62–7.70 (2H, m), 7.83 (1H, d, J=8.3 Hz), 7.87 (1H, d, J=8.3 Hz), 8.12 (1H, s).

REFERENCE EXAMPLE 52

Methyl 5-hydroxyanthranylate (835 mg) was dissolved in 10 ml of tetrahydrofuran, 863 mg of 1-t-butoxycarbonyl-4-hydroxypiperidine, 1,572 mg of triphenylphosphine and 1,044 mg of diethyl azodicarboxylate were added to the solution, and the mixture was stirred at room temperature for 4 days. The reaction solution was evaporated and ethyl acetate was added. The mixture was washed with saturated sodium bicarbonate aqueous solution and 10% citric acid aqueous solution, dried over anhydrous sodium sulfate, and then evaporated. The resulting residue was purified by silica gel column chromatography using hexane:ethyl acetate (85:15) as the eluent to give 716 mg of methyl 5-[(1-t-butoxycarbonyl-4-piperidyl)oxy]anthranylate.

Mass spectrometry data (m/z): 350 (M)$^+$.

Nuclear magnetic resonance spectrum (CDCl$_3$, TMS internal standard) δ: 1.47 (9H, s), 1.63–1.76 (2H, m), 1.80–1.93 (2H, m), 3.22–3.32 (2H, m), 3.62–3.75 (2H, m), 3.87 (3H, s), 4.23–4.31 (1H, m), 5.47 (2H, bs), 6.63 (1H, d, J=8.5 Hz), 6.96 (1H, dd, J=8.5, 3.1 Hz), 7.41 (1H, d, J=3.1 Hz).

The following compound of Reference Example 53 was obtained in the same manner as described in Reference Example 2.

REFERENCE EXAMPLE 53

Methyl 5-[(1-t-butoxycarbonyl-4-piperidyl)oxy]-N-[(7-cyano-2-naphthyl)methyl]anthranylate Starting compound: methyl 5-[(1-t-butoxycarbonyl-4-piperidyl)oxy]anthranylate, 7-formyl-2-naphthalenecarbonitrile.

Mass spectrometry data (m/z): 515 (M)$^+$.

Nuclear magnetic resonance spectrum (CDCl$_3$, TMS internal standard) δ: 1.46 (9H, s), 1.61–1.73 (2H, m), 1.79–1.91 (2H, m), 3.21–3.31 (2H, m), 3.61–3.73 (2H, m), 3.89 (3H, s), 4.21–4.30 (1H, m), 4.62 (2H, s), 6.55 (1H, d, J=9.1 Hz), 6.95 (1H, dd, J=9.1, 3.1 Hz), 7.52 (1H, d, J=3.0 Hz), 7.58 (1H, d, J=8.2 Hz), 7.64 (1H, d, J=8.5 Hz), 7.83 (1H, s), 7.87 (1H, d, J=8.5 Hz), 7.89 (1H, d, J=8.5 Hz), 8.05 (1H, bs), 8.18 (1H, s).

The following compound of Reference Example 54 was obtained in the same manner as described in Reference Example 2.

REFERENCE EXAMPLE 54

7-[[4-[[(3S)-1-t-Butoxycarbonyl-3-pyrrolidinyl]oxy]anilino]methyl]-2-naphthalenecarbonitrile Starting compound: 7-formyl-2-naphthalenecarbonitrile, 4-[[(3S)-1-t-butoxycarbonyl-4-pyrrolidinyl]oxy]aniline.

Mass spectrometry data (m/z): 443 (M)$^+$.

Nuclear magnetic resonance spectrum (CdCl$_3$, TMS internal standard) δ: 1.45 (9H, s), 1.92–2.18 (2H, m), 3.40–3.65 (4H, m), 4.30 (1H, bs), 4.50 (2H, s), 4.68–4.77 (1H, m), 6.54–6.66 (2H, m), 6.74 (2H, d, J=8.8 Hz), 7.58 (1H, d, J=8.3 Hz), 7.66 (1H, d, J=9.8 Hz), 7.85–7.93 (3H, m), 8.17–8.23 (1H, m).

The following compound of Reference Example 55 was obtained in the same manner as described in Reference Example 18.

REFERENCE EXAMPLE 55

Ethyl N-[N-[[4-[(3S)-1-t-butoxycarbonyl-3-pyrrolidinyl]oxy]phenyl]-N-[(7-cyano-2-naphthyl)methyl]sulfamoyl]carbamate Starting compound: 7-[[4-[[(3S)-1-t-butoxycarbonyl-3-pyrrolidinyl]oxy]anilino]methyl-2-naphthalenecarbonitrile.

Mass spectrometry data (m/z): 594 (M)$^+$.

Nuclear magnetic resonance spectrum (CDCl$_3$, TMS internal standard) δ: 1.36 (3H, t, J=6.8 Hz), 1.44 (9H, s), 1.96–2.20 (2H, m), 3.39–3.60 (4H, m), 4.33 (2H, q, J=6.8 Hz), 4.70–4.82 (1H, m), 5.21 (2H, s), 6.75 (2H, d, J=8.8 Hz), 7.17 (2H, d, J=8.8 Hz), 7.32 (1H, bs), 7.58 (1H, d, J=8.6 Hz), 7.62–7.70 (2H, m), 7.84 (1H, d, J=8.3 Hz), 7.87 (1H, d, J=8.3 Hz), 8.13 (1H, s).

REFERENCE EXAMPLE 56

Ethyl[N-[4-[(1-t-butoxycarbonyl-4-piperidyl)oxy]phenyl]-N-[(7-cyano-2-naphthyl)methyl]sulfamoyl]acetate (500 mg) was dissolved in 10 ml of acetonitrile, 0.52 ml of methyl iodide and 136 mg of potassium carbonate were added to the solution, and the mixture was stirred under reflux for 5 hours and 30 minutes. After cooling the reaction solution, the precipitate was removed by filtration, and the resulting filtrate was concentrated under a reduced pressure. The resulting residue was applied to silica gel column chromatography, which was eluted with hexane:ethyl acetate (3:1) to give 415 mg of ethyl 2-[N-[4-[(1-t-butoxycarbonyl-4-piperidyl)oxy]phenyl]-N-[(7-cyano-2-naphthyl)methyl]sulfamoyl]propionate.

Mass spectrometry data (m/z): 621 (M)$^+$.

Nuclear magnetic resonance spectrum (CDCl$_3$, TMS internal standard) δ: 1.21–2.15 (19H, m), 3.08–3.79 (4H, m), 4.00–5.32 (6H, m), 6.65–6.89 (2H, m), 7.18–7.38 (2H, m), 7.41–8.07 (6H, m).

The following compounds of Reference Examples 57 and 58 were obtained in the same manner as described in Reference Example 56.

REFERENCE EXAMPLE 57

Ethyl 2-[N-[4-[(1-t-butoxycarbonyl-4-piperidyl)oxy] phenyl]-N-[(7-cyano-2-naphthyl)methyl]sulfamoyl] butylate Starting compound: ethyl N-[4-[(1-t-butoxycarbonyl-4-piperidyl)oxy]phenyl]-N-[(7-cyano-2-naphthyl)methyl] sulfamoylacetate.

Mass spectrometry data (m/z): 635 (M)$^+$.

Nuclear magnetic resonance spectrum (CDCl$_3$, TMS internal standard) δ: 0.90–1.11 (6H, m), 1.45 (9H, s), 1.50–2.32 (6H, m), 3.12–4.10 (4H, m), 4.14–5.25 (6H, m), 6.67–6.87 (2H, m), 7.16–7.32 (2H, m), 7.44–7.92 (7H, m), 8.05 (1H, s).

REFERENCE EXAMPLE 58

Ethyl 2-[N-[4-[(1-t-butoxycarbonyl-4-piperidyl)oxy] phenyl]-N-[(7-cyano-2-naphthyl)methyl]sulfamoyl] valerate Starting compound: ethyl[N-[4-[(1-t-butoxycarbonyl-4-piperidyl)oxy]phenyl]-N-[(7-cyano-2-naphthyl)methyl] sulfamoyl]acetate.

Mass spectrometry data (m/z): 649 (M)$^+$.

Nuclear magnetic resonance spectrum (CDCl$_3$, TMS internal standard) δ: 0.77–1.06 (6H, m), 1.15–1.40 (4H, m), 1.45 (9H, s), 1.54–2.32 (4H, m), 3.08–3.83 (4H, m), 3.92 5.28 (6H, m), 6.71–6.89 (2H, m), 7.19–7.36 (2H, m), 7.45–7.94 (7H, m), 8.05 (1H, s).

EXAMPLE 1

N-[4-[(1-t-Butoxycarbonyl-4-piperidyl)oxy]phenyl]-N-[(7-cyano-2-naphthyl)methyl]acetamide obtained in Reference Example 3 (128 mg) was dissolved in a mixed solution of 2 ml dichloromethane and 5 ml ethanol. While stirring, this solution was cooled to −20° C. and hydrogen chloride was introduced until saturation. This reaction solution was stirred at 5° C. for 4 days and then evaporated. Ethanol solution (5 ml) which has been saturated with ammonia at 10° C. was added to the resulting residue, and the mixture was stirred at 5° C. for 6 days. The reaction solution was evaporated, and the resulting residue was purified by an ODS (YMC-GEL ODS-A 120-230/70) column chromatography using methanol:water (2:98) as the eluent, followed by addition of a small amount of 1N hydrochloric acid and freeze-drying to give 92 mg of N-[(7-amidino-2-naphthyl) methyl]-N-[4-[(4-piperidyl)oxy]phenyl]acetamide dihydrochloride.

Mass spectrometry data (m/z): 417 (M-2HCl+1)$^+$.

Nuclear magnetic resonance spectrum (DMSO-d$_6$, TMS internal standard) δ: 1.75–7.85 (2H, m), 1.86 (3H, s), 2.03–2.11 (2H, m), 2.96–3.05 (2H, m), 3.13–3.22 (2H, m), 4.53–4.64 (1H, m), 5.03 (2H, s), 6.96 (2H, d, J=8.5 Hz), 7.15 (2H, d, J=8.5 Hz), 7.59 (1H, d, J=8.6 Hz), 7.81 (1H, d, J=8.6 Hz), 7.85 (1H, s), 8.01 (1H, d, J=7.9 Hz), 8.11 (1H, d, J=8.6 Hz), 8.47 (1H, s), 9.07 (1H, brs), 9.14 (1H, brs), 9.28 (2H, s), 9.50 (2H, s).

The following compounds of Examples 2 to 11 were obtained in the same manner as described in Example 1.

EXAMPLE 2

N-[(7-Amidino-2-naphthyl)methyl]-N-[4-[(4-piperidyl)oxy]phenyl]oxamide dihydrochloride Starting compound: ethyl-N-[4-[(1-t-butoxycarbonyl-4-piperidyl)oxy]phenyl]-N-[(7-cyano-2-naphthyl)methyl] oxamate.

Mass spectrometry data (m/z): 446 (M-2HCl+1)$^+$.

Nuclear magnetic resonance spectrum (DMSO-d$_6$, TMS internal standard) δ: 1.72–1.80 (2H, m), 2.00–2.09 (2H, m), 2.95–3.05 (2H, m), 3.11–3.21 (2H, m), 4.52–4.60 (1H, m), 5.01 (2H, s), 6.90 (2H, d, J=9.2 Hz), 7.15 (2H, d, J=8.5 Hz), 7.47 (1H, s), 7.61 (1H, d, J=8.5 Hz), 7.82 (1H, d, J=8.5 Hz), 7.89 (1H, s), 8.04 (2H, d, J=8.5 Hz), 8.08–8.13 (3H, m), 8.46 (1H, s), 9.05 (1H, bs), 9.13 (1H, bs), 9.29 (2H, s), 9.52 (2H, s).

EXAMPLE 3

N-[(7-Amidino-2-naphthyl)methyl]-N-[4-[(4-piperidyl)oxy]phenyl]cyclopropanecarboxamide dihydrochloride Starting compound: N-[4-[(1-t-butoxycarbonyl-4-piperidyl)oxy]phenyl]-N-[(7-cyano-2-naphthyl)methyl] cyclopropanecarboxamide.

Mass spectrometry data (m/z): 443 (M-2HCl+1)$^+$.

Nuclear magnetic resonance spectrum (DMSO-d$_6$, TMS internal standard) δ: 0.67–0.63 (2H, m), 0.80–0.88 (2H, m), 1.34–1.38 (1H, m), 1.80–1.82 (2H, m), 2.00–2.10 (2H, m), 3.01–3.04 (2H, m), 3.12–3.18 (2H, m), 4.60–4.62 (1H, m), 5.06 (2H, s), 6.98 (2H, d, J=9.2 Hz), 7.16 (2H, d, J=9.2 Hz), 7.54 (1H, d, J=8.0 Hz), 7.81 (1H, s), 7.82 (1H, d, J=9.8 Hz), 8.01 (1H, d, J=8.6 Hz), 8.10 (1H, d, J=9.2 Hz), 8.48 (1H, s), 9.17 (1H, bs), 9.24 (1H, bs), 9.33 (2H, s), 9.52 (2H, s).

EXAMPLE 4

N-[(7-Amidino-2-naphthyl)methyl]-N-[4-[(4-piperidyl)oxy]phenyl]benzamide dihydrochloride Starting compound: N-[4-[(1-t-butoxycarbonyl-4-piperidyl)oxy]phenyl]-N-[(7-cyano-2-naphthyl)methyl] benzamide.

Mass spectrometry data (m/z): 479 (M-2HCH+1)$^+$.

Nuclear magnetic resonance spectrum (DMSO-d$_6$, TMS internal standard) δ: 1.72–1.74 (2H, m), 1.97–2.00 (2H, m), 2.95–2.98 (2H, m), 3.10–3.12 (2H, m), 4.49–4.51 (1H, m), 5.26 (2H, s), 6.78 (2H, d, J=9.2 Hz), 7.03 (2H, d, J=8.6 Hz), 7.24–7.30 (3H, m), 7.36 (2H, d, J=7.3 Hz), 7.68 (1H, d, J=8.5 Hz), 7.84 (1H, d, J=8.5 Hz), 7.97 (1H, s), 8.03 (1H, d, J=8.6 Hz), 8.11 (1H, d, J=8.6 Hz), 8.55 (1H, s), 9.23 (1H, bs), 9.32 (1H, bs), 9.41 (2H, s), 9.58 (2H, s).

EXAMPLE 5

N-[(7-Amidino-2-naphthyl)methyl]-N-[4-[(4-piperidyl)oxy]phenyl]ethanecarboxamide dihydrochloride Starting compound: N-[4-[(1-t-butoxycarbonyl-4-piperidyl)oxy]phenyl]-N-[(7-cyano-2-naphthyl)methyl] ethanecarboxamide.

Mass spectrometry data (m/z): 431 (M-2HCl+1)$^+$.

Nuclear magnetic resonance spectrum (DMSO-d$_6$, TMS internal standard) δ: 0.99 (3H, t, J=7.3 Hz), 1.84–1.85 (2H, m), 2.09–2.10 (4H, m), 3.02–3.04 (2H, m), 3.14–3.16 (2H, m), 5.04 (2H, s), 6.97 (2H, d, J=9.1 Hz), 7.12 (2H, d, J=9.0 Hz), 7.68 (1H, d, J=8.5 Hz), 7.84 (1H, d, J=8.5 Hz), 7.88 (1H, s), 8.01–8.11 (2H, m), 8.56 (1H, s), 9.20 (1H, bs), 9.32 (1H, bs), 9.52 (2H, s), 9.69 (2H, s).

EXAMPLE 6

N-[(7-Amidino-2-naphthyl)methyl]-N-[4-[(4-piperidyl)oxy]phenyl]cyclohexanecarboxamide dihydrochloride Starting compound: N-[4-[(1-t-butoxycarbonyl-4-piperidyl)oxy]phenyl]-N-[(7-cyano-2-naphthyl)methyl] cyclohexanecarboxamide.

Mass spectrometry data (m/z): 485 (M-2HCl+1)⁺.

Nuclear magnetic resonance spectrum (DMSO-$d_6$, TMS internal standard) δ: 0.91–0.93 (2H, m), 1.13–1.15 (1H, m), 1.41–1.48 (2H, m), 1.51–1.53 (1H, m), 1.63–1.71 (4H, m), 1.81–1.83 (2H, m), 2.06–2.10 (2H, m), 2.18–2.23 (1H, m), 3.00–3.04 (2H, m), 3.16–3.18 (2H, m), 4.60–4.62 (1H, m), 4.98 (2H, s), 6.97 (2H, d, J=8.6 Hz), 7.09 (2H, d, J=8.5 Hz), 7.54 (1H, d, J=7.3 Hz), 7.79 (1H, s), 7.83 (1H, d, J=6.7 Hz), 8.01 (1H, d, J=8.6 Hz), 8.10 (1H, d, J=9.2 Hz), 8.49 (1H, s), 9.22 (1H, bs), 9.29 (1H, bs), 9.37 (2H, s), 9.55 (2H, s).

EXAMPLE 7

N-[(7-Amidino-2-naphthyl)methyl]-N-[4-[(4-piperidyl)oxy]phenyl]-1-naphthalenecarboxamide dihydrochloride Starting compound: N-[4-[(1-t-butoxycarbonyl-4-piperidyl)oxy]phenyl]-N-[(7-cyano-2-naphthyl)methyl]-1-naphthalenecarboxamide.

Mass spectrometry data (m/z): 529 (M-2HCl+1)⁺.

Nuclear magnetic resonance spectrum (DMSO-$d_6$, TMS internal standard) δ: 1.60–1.64 (2H, m), 1.84–1.89 (2H, m), 2.86–2.90 (2H, m), 3.01–3.05 (2H, m), 4.32–4.36 (1H, m), 5.40 (1H, s), 6.59 (2H, d, J=9.2 Hz), 6.95 (2H, d, J=8.5 Hz), 7.34 (1H, t, J=7.9 Hz), 7.44 (1H, d, J=7.3 Hz), 7.52 (1H, t, J=7.3 Hz), 7.61 (1H, t, J=7.9 Hz), 7.81 (2H, t, J=8.5 Hz), 7.87 (2H, d, J=7.3 Hz), 8.03 (1H, s), 8.07–8.15 (3H, m), 8.61 (1H, s), 9.20 (1H, bs), 9.30 (1H, bs), 9.45 (2H, s), 9.64 (2H, s).

EXAMPLE 8

N-[(7-Amidino-2-naphthyl)methyl]-N-[4-[(4-piperidyl)oxy]phenyl]-2-fluorobenzamide dihydrochloride Starting compound: N-[4-[(1-t-butoxycarbonyl-4-piperidyl)oxy]phenyl]-N-[(7-cyano-2-naphthyl)methyl]-2-fluorobenzamide.

Mass spectrometry data (m/z): 497 (M-2HCl+1)⁺.

Nuclear magnetic resonance spectrum (DMSO-$d_6$, TMS internal standard) δ: 1.68–1.71 (2H, m), 1.90–1.96 (2H, m), 2.91–2.95 (2H, m), 3.05–3.10 (2H, m), 4.41–4.47 (1H, m), 5.27 (2H, s), 6.75 (2H, d, J=9.2 Hz), 7.00 (2H, d, J=9.2 Hz), 7.06 (1H, t, J=9.2 Hz), 7.11 (1H, t, J=7.3 Hz), 7.30–7.32 (1H, m), 7.45 (1H, t, J=6.1 Hz), 7.69 (1H, d, J=8.6 Hz), 7.85 (1H, d, J=8.5 Hz), 7.96 (1H, s), 8.07 (1H, d, J=8.6 Hz), 8.13 (1H, d, J=8.5 Hz), 8.53 (1H, s), 9.18 (1H, bs), 9.26 (1H, bs), 9.39 (2H, s), 9.58 (2H, s).

EXAMPLE 9

N-[(7-Amidino-2-naphthyl)methyl]-N-[4-[(4-piperidyl)oxy]phenyl]-3-methoxybenzamide dihydrochloride Starting compound: N-[4-(1-t-butoxycarbonyl-4-piperidyl)oxy]phenyl]-N-[(7-cyano-2-naphthyl)methyl]-3-methoxybenzamide.

Mass spectrometry data (m/z): 509 (M-2HCl+1)⁺.

Nuclear magnetic resonance spectrum (DMSO-$d_6$, TMS internal standard) δ: 1.70–1.76 (2H, m), 1.92–2.01 (2H, m), 2.91–2.97 (2H, m), 3.11–3.16 (2H, m), 3.64 (3H, s), 4.50–4.52 (1H, m), 5.26 (2H, s), 6.80 (2H, d, J=9.2 Hz), 6.85 (1H, d, J=6.1 Hz), 6.90–6.93 (2H, m), 7.05 (2H, d, J=7.9 Hz), 7.15 (1H, t, J=7.9 Hz), 7.68 (1H, d, J=9.8 Hz), 7.83 (1H, d, J=6.7 Hz), 7.95 (1H, s), 8.03 (1H, d, J=8.5 Hz), 8.11 (1H, d, J=8.55 Hz), 8.54 (1H, s), 9.18 (1H, bs), 9.24 (1H, bs), 9.36 (2H, s), 9.55 (2H, s).

EXAMPLE 10

N-[(7-Amidino-2-naphthyl)methyl]-N-[4-[(4-piperidyl)oxy]phenyl]-2-thiophenamide dihydrochloride Starting compound: N-[4-[(1-t-butoxycarbonyl-4-piperidyl)oxy]phenyl]-N-[(7-cyano-2-naphthyl)methyl]-2-thiophenamide.

Mass spectrometry data (m/z): 485 (M-2HCl+1)⁺.

Nuclear magnetic resonance spectrum (DMSO-$d_6$, TMS internal standard) δ: 1.81–1.83 (2H, m), 2.03–2.07 (2H, m), 3.00–3.07 (2H, m), 3.15–3.18 (2H, m), 4.61–4.65 (1H, m), 5.20 (2H, s), 6.76 (1H, s), 6.93 (1H, t, J=4.3 Hz), 6.98 (2H, d, J=8.5 Hz), 7.19 (2H, d, J=8.6 Hz), 7.65–7.68 (2H, m), 7.83 (1H, d, J=8.6 Hz), 7.94 (1H, s), 8.02 (1H, d, J=8.5 Hz), 8.11 (1H, d, J=8.6 Hz), 9.22 (1H, bs), 9.28 (1H, bs), 9.35 (2H, s), 9.53 (2H, s).

EXAMPLE 11

N-[(7-Amidino-2-naphthyl)methyl]-N-[4-[(4-piperidyl)oxy]phenyl]-2-pyridinecarboxamide trihydrochloride Starting compound: N-[4-[(1-t-butoxycarbonyl-4-piperidyl)oxy]phenyl]-N-[(7-cyano-2-naphthyl)methyl]-3-pyridinecarboxamide.

Mass spectrometry data (m/z): 480 (M-3HCl+1)⁺.

Nuclear magnetic resonance spectrum (DMSO-$d_6$, TMS internal standard) δ: 1.71–1.75 (2H, m), 1.96–1.99 (2H, m), 2.95–2.97 (2H, m), 3.00–3.17 (2H, m), 4.50–4.52 (1H, m), 5.30 (1H, s), 6.82 (2H, d, J=8.6 Hz), 7.15 (2H, d, J=8.5 Hz), 7.65–7.67 (1H, m), 7.73 (1H, d, J=8.6 Hz), 7.84 (1H, d, J=8.6 Hz), 8.01 (1H, s), 8.04 (1H, d, J=7.9 Hz), 8.12 (1H, d, J=8.6 Hz), 8.14–8.15 (1H, m), 8.56 (1H, s), 8.66 (1H, s), 8.75 (1H, s), 9.21 (2H, bs), 9.38 (1H, bs), 9.40 (2H, s), 9.58 (2H, s).

EXAMPLE 12

N-[(7-Amidino-2-naphthyl)methyl]-N-[4-[(4-piperidyl)oxy]phenyl]acetamide dihydrochloride (56 mg) was dissolved in 2 ml of ethanol, 28 mg of ethyl acetoimidate hydrochloride and 36 mg of triethylamine were added to the solution, and the mixture was stirred at room temperature for 2 days. The reaction solution was evaporated, and the resulting residue was purified by an ODS (YMC-GEL ODS-A 120-230/70) column chromatography using methanol:water (2:98) as the eluent, followed by addition of a small amount of 1N hydrochloric acid and freeze-drying to give 60 mg of N-[4-[(1-acetoimidoyl-4-piperidyl)oxy]phenyl]-N-[(7-amidino-2-naphthyl)methyl]acetamide dihydrochloride.

Mass spectrometry data (m/z): 458 (M-2HCl+1)⁺.

Nuclear magnetic resonance spectrum (DMSO-$d_6$, TMS internal standard) δ: 1.61–1.76 (2H, m), 1.87 (3H, s), 1.95–2.06 (2H, m), 2.28 (3H, m), 3.43–3.55 (2H, m), 3.65–3.73 (1H, m), 3.75–3.84 (1H, m), 4.65 (1H, bs), 5.03 (2H, s), 6.96 (2H, d, J=8.5 Hz), 7.15 (2H, d, J=8.5 Hz), 7.59 (1H, d, J=8.5 Hz), 7.81 (1H, d, J=8.5 Hz), 7.85 (1H, s), 8.01 (1H, d, J=8.5 Hz), 8.11 (1H, d, J=8.5 Hz), 8.48 (1H, s), 8.80 (1H, s), 9.30 (2H, s), 9.33 (1H, s), 9.51 (2H, s).

The following compounds of Examples 13 to 22 were obtained in the same manner as described in Example 12.

EXAMPLE 13

N-[4-[(1-Acetoimidoyl-4-piperidyl)oxy]phenyl]-N-[(7-amidino-2-naphthyl)methyl]oxamide dihydrochloride Starting compound: N-[(7-amidino-2-naphthyl)methyl]-N-[4-[(4-piperidyl)oxy]phenyl]oxamide dihydrochloride.

Mass spectrometry data (m/z): 487 (M-2HCl+1)$^+$.

Nuclear magnetic resonance spectrum (DMSO-$d_6$, TMS internal standard) δ: 1.61–1.75 (2H, m), 1.95–2.05 (2H, m), 2.27 (3H, s), 3.43–3.54 (2H, m), 3.45–3.75 (1H, m), 3.75–3.82 (1H, m), 4.61 (1H, bs), 5.08 (2H, s), 6.91 (2H, d, J=8.5 Hz), 7.15 (1H, d, J=8.5 Hz), 7.47 (1H, s), 7.62 (1H, d, J=8.5 Hz), 7.82 (1H, d, J=8.5 Hz), 7.90 (1H, s), 8.04 (1H, d, J=8.5 Hz), 8.10–8.15 (2H, m), 8.46 (1H, s), 8.75 (1H, s), 8.24 (2H, s), 8.27 (1H, s), 9.50 (2H, s).

EXAMPLE 14

N-[4-[(1-Acetoimidoyl-4-piperidyl)oxy]phenyl]-N-[(7-amidino-2-naphthyl)methyl]cyclopropanecarboxamide dihydrochloride Starting compound: N-[(7-amidino-2-naphthyl)methyl]-N-[4-[(4-piperidyl)oxy]phenyl]cyclopropanecarboxamide dihydrochloride.

Mass spectrometry data (m/z): 484 (M-2HCl+1)$^+$.

Nuclear magnetic resonance spectrum (DMSO-$d_6$, TMS internal standard) δ: 0.64–0.68 (2H, m), 0.84–0.89 (2H, m), 1.37–1.39 (1H, m), 1.68–1.75 (2H, m), 2.00–2.09 (2H, m), 2.28 (3H, s), 3.45–3.49 (2H, m), 3.69–3.80 (2H, m), 4.61–4.67 (1H, m), 5.08 (2H, s), 6.98 (2H, d, J=8.5 Hz), 7.17 (2H, d, J=9.2 Hz), 7.55 (1H, d, J=8.6 Hz), 7.80–7.83 (1H, m), 8.01 (1H, d, J=8.6 Hz), 8.10 (1H, d, J=8.6 Hz), 8.47 (1H, s), 8.79 (1H, s), 9.22–9.30 (3H, m), 9.49 (2H, s).

EXAMPLE 15

N-[4-[(1-Acetoimidoyl-4-piperidyl)oxy]phenyl]-N-[(7-amidino-2-naphthyl)methyl]benzamide dihydrochloride Starting compound: N-[(7-amidino-2-naphthyl)methyl]-N-[4-[(4-piperidyl)oxy]phenyl]benzamide dihydrochloride.

Mass spectrometry data (m/z): 520 (M-2HCl+1)$^+$.

Nuclear magnetic resonance spectrum (DMSO-$d_6$, TMS internal standard) δ: 1.51–1.61 (2H, m), 1.87–1.99 (2H, m), 2.26 (3H, m), 3.02–3.08 (2H, m), 3.62–3.71 (2H, m), 4.52–4.59 (1H, m), 5.27 (2H, s), 6.79 (2H, d, J=8.6 Hz), 7.02 (2H, d, J=8.5 Hz), 7.13 (1H, s), 7.23–7.35 (4H, m), 7.69 (1H, d, J=8.4 Hz), 7.81 (1H, d, J=8.5 Hz), 7.97 (1H, s), 8.03 (1H, d, J=8.6 Hz), 8.11 (1H, d, J=8.6 Hz), 8.52 (1H, s), 8.74 (1H, s), 9.27 (3H, s), 9.50 (2H, s).

EXAMPLE 16

N-[4-[(1-Acetoimidoyl-4-piperidyl)oxy]phenyl]-N-[(7-amidino-2-naphthyl)methyl]ethanecarboxamide dihydrochloride Starting compound: N-[(7-amidino-2-naphthyl)methyl]-N-[4-[(4-piperidyl)oxy]phenyl]ethanecarboxamide dihydrochloride.

Mass spectrometry data (m/z): 472 (M-2HCl+1)$^+$.

Nuclear magnetic resonance spectrum (DMSO-$d_6$, TMS internal standard) δ: 0.99 (3H, t, J=9.3 Hz), 1.64–1.80 (2H, m), 1.94–2.14 (4H, m), 2.28 (3H, s), 3.02–3.09 (2H, m), 3.62–3.80 (2H, m), 4.60–4.64 (1H, m), 5.03 (2H, s), 6.95 (2H, d, J=9.2 Hz), 7.12 (2H, d, J=8.5 Hz), 7.48 (1H, d, J=8.5 Hz), 7.78–7.86 (2H, m), 8.00 (1H, d, J=8.4 Hz), 8.11 (1H, d, J=8.6 Hz), 8.48 (1H, s), 8.82 (1H, s), 9.30 (3H, s), 9.51 (2H, s).

EXAMPLE 17

N-[4-[(1-Acetoimidoyl-4-piperidyl)oxy]phenyl]-N-[(7-amidino-2-naphthyl)methyl]cyclohexanecarboxamide dihydrochloride Starting compound: N-[(7-amidino-2-naphthyl)methyl]-N-[4-[(4-piperidyl)oxy]phenyl]cyclohexanecarboxamide dihydrochloride.

Mass spectrometry data (m/z): 526 (M-2HCl+1)$^+$.

Nuclear magnetic resonance spectrum (DMSO-$d_6$, TMS internal standard) δ: 0.90–0.93 (2H, m), 1.13–1.16 (1H, m), 1.43–1.46 (2H, m), 1.50–1.53 (1H, m), 1.64–1.70 (6H, m), 2.00–2.10 (2H, m), 2.10–2.21 (1H, m), 2.28 (3H, s), 3.45–3.49 (2H, m), 3.69–3.80 (2H, m), 4.64–4.68 (1H, m), 4.99 (2H, s), 6.97 (2H, d, J=8.6 Hz), 7.09 (2H, d, J=8.5 Hz), 7.54 (1H, d, J=8.5 Hz), 7.79–7.83 (2H, m), 8.01 (1H, d, J=8.6 Hz), 8.11 (1H, d, J=8.6 Hz), 8.47 (1H, s), 8.80 (1H, s), 9.30 (3H, s), 9.51 (2H, s).

EXAMPLE 18

N-[4-[(1-Acetoimidoyl-4-piperidyl)oxy]phenyl]-N-[(7-amidino-2-naphthyl)methyl]-1-naphthalenecarboxamide dihydrochloride Starting compound: N-[(7-amidino-2-naphthyl)methyl]-N-[4-[(4-piperidyl)oxy]phenyl]-1-naphthalenecarboxamide dihydrochloride.

Mass spectrometry data (m/z): 570 (M-2HCl+1)$^+$.

Nuclear magnetic resonance spectrum (DMSO-$d_6$, TMS internal standard) δ: 1.42–1.55 (2H, m), 1.78–1.89 (2H, m), 2.27 (3H, s), 3.37–3.42 (2H, m), 3.57–3.65 (2H, m), 4.38–4.44 (1H, m), 5.39 (2H, s), 6.59 (2H, d, J=8.8 Hz), 6.95 (2H, d, J=8.3 Hz), 7.34 (1H, t, J=7.8 Hz), 7.43 (1H, d, J=6.8 Hz), 7.53 (1H, t, J=7.3 Hz), 7.62 (1H, t, J=7.3 Hz), 7.79–7.89 (4H, m), 8.04–8.17 (4H, m), 8.53 (1H, s), 8.61 (1H, s), 9.17 (3H, s), 9.48 (2H, s).

EXAMPLE 19

N-[4-[(1-Acetoimidoyl-4-piperidyl)oxy]phenyl]-N-[(7-amidino-2-naphthyl)methyl]-2-fluorobenzamide dihydrochloride Starting compound: N-[(7-amidino-2-naphthyl)methyl]-N-[4-[(4-piperidyl)oxy]phenyl]-2-fluorobenzamide dihydrochloride.

Mass spectrometry data (m/z): 538 (M-2HCl+1)$^+$.

Nuclear magnetic resonance spectrum (DMSO-$d_6$, TMS internal standard) δ: 1.52–1.62 (2H, m), 1.86–1.94 (2H, m), 2.25 (3H, s), 3.40–3.45 (2H, m), 3.65–3.73 (2H, m), 4.46–4.56 (1H, m), 5.26 (2H, s), 6.75 (2H, d, J=8.6 Hz), 6.99 (2H, d, J=8.6 Hz), 7.05 (1H, t, J=8.5 Hz), 7.11 (1H, t, J=7.3 Hz), 7.30–7.32 (1H, m), 7.69 (1H, d, J=7.9 Hz), 7.83 (1H, d, J=8.6 Hz), 7.96 (1H, s), 8.07 (1H, d, J=8.6 Hz), 8.13 (1H, d, J=8.5 Hz), 8.50 (1H, s), 8.76 (1H, s), 9.31 (3H, s), 9.53 (2H, s).

EXAMPLE 20

N-[4-[(1-Acetoimidoyl-4-piperidyl)oxy]phenyl]-N-[(7-amidino-2-naphthyl)methyl]-3-methoxybenzamide dihydrochloride Starting compound: N-[(7-amidino-2-naphthyl)methyl]-N-[4-[(4-piperidyl)oxy]phenyl]-3-methoxybenzamide dihydrochloride.

Mass spectrometry data (m/z): 549 (M-2HCl+1)$^+$.

Nuclear magnetic resonance spectrum (DMSO-$d_6$, TMS internal standard) δ: 1.57–1.68 (2H, m), 1.90–1.98 (2H, m), 2.25 (3H, s), 3.41–3.48 (2H, m), 3.63 (3H, s), 3.70–3.78 (2H, m), 4.54–4.58 (1H, m), 5.26 (2H, s), 6.80 (2H, d, J=9.2 Hz), 6.85–6.94 (3H, m), 7.05 (2H, d, J=7.9 Hz), 7.16 (1H, t, J=7.9 Hz), 7.68 (1H, d, J=8.5 Hz), 7.81 (1H, d, J=7.3 Hz), 7.97 (1H, s), 8.03 (1H, d, J=8.5 Hz), 8.11 (1H, d, J=8.6 Hz), 8.51 (1H, s), 8.72 (1H, s), 9.24 (3H, s), 9.49 (2H, s).

EXAMPLE 21

N-[4-[(1-Acetoimidoyl-4-piperidyl)oxy]phenyl]-N-[(7-amidino-2-naphthyl)methyl]thiophenamide dihydrochloride Starting compound: N-[(7-amidino-2-naphthyl)methyl]-N-[4-[(4-piperidyl)oxy]phenyl]-2-thiophenamide dihydrochloride.

Mass spectrometry data (m/z): 526 (M-2HCl+1)$^+$.

Nuclear magnetic resonance spectrum (DMSO-$d_6$, TMS internal standard) δ: 1.64–1.71 (2H, m), 1.98–2.08 (2H, m), 2.29 (3H, s), 3.42–3.58 (2H, m), 3.71–3.82 (2H, m), 4.62–4.72 (1H, m), 5.20 (2H, s), 6.76 (1H, d, J=3.1 Hz), 6.93 (1H, t, J=4.9 Hz), 6.99 (2H, d, J=8.6 Hz), 7.17 (2H, d, J=8.6 Hz), 7.65 (1H, d, J=10.4 Hz), 7.69 (1H, d, J=4.3 Hz), 7.83 (1H, d, J=8.6 Hz), 7.95 (1H, s), 8.03 (1H, d, J=8.5 Hz), 8.11 (1H, d, J=8.6 Hz), 8.51 (1H, s), 8.85 (1H, s), 9.37 (3H, s), 9.52 (2H, s).

EXAMPLE 22

N-[4-[(1-Acetoimidoyl-4-piperidyl)oxy]phenyl]-N-[(7-amidino-2-naphthyl)methyl]-3-pyridinecarboxamide trihydrochloride Starting compound: N-[(7-amidino-2-naphthyl)methyl]-N-[4-[(4-piperidyl)oxy]phenyl]-2-pyridinecarboxamide trihydrochloride.

Mass spectrometry data (m/z): 521 (M-3HCl+1)$^+$.

Nuclear magnetic resonance spectrum (DMSO-$d_6$, TMS internal standard) δ: 1.56–1.64 (2H, m), 1.91–1.99 (2H, m), 2.27 (3H, s), 3.41–3.52 (2H, m), 3.64–3.80 (2H, m), 4.52–4.58 (1H, m), 5.30 (2H, s), 6.83 (2H, d, J=7.9 Hz), 7.14 (2H, d, J=7.9 Hz), 7.28–7.31 (2H, m), 7.61–7.66 (1H, m), 7.72 (1H, d, J=8.6 Hz), 7.86 (1H, d, J=8.5 Hz), 8.00 (1H, s), 8.04 (1H, d, J=8.6 Hz), 8.12 (1H, d, J=8.6 Hz), 8.58 (1H, s), 8.74–8.79 (1H, m), 8.92 (1H, s), 9.45 (4H, s), 9.62 (2H, s).

EXAMPLE 23

Ethyl N-[4-[(1-t-butoxycarbonyl-4-piperidyl)oxy]phenyl]-N-[(7-cyano-2-naphthyl)methyl]oxamate obtained in Reference Example 4 (325 mg) was dissolved in a mixed solution of 2 ml dichloromethane and 5 ml ethanol. While stirring, this solution was cooled to −20° C. and hydrogen chloride was introduced until saturation. This reaction solution was stirred at −5° C. for 2 days and evaporated. The resulting residue was dissolved in 5 ml of ethanol, 224 mg of ammonium acetate was added to the solution, and the mixture was stirred at 5° C. for 3 days and then at room temperature for 1 day. This reaction solution was evaporated, and the resulting residue was purified by an ODS (YMC-GEL ODS-A 120-230/70) column chromatography. Partially purified ethyl N-[(7-amidino-2-naphthyl)methyl]-N-[4-[(4-piperidyl)oxy]phenyl]oxamate was obtained from a fraction eluted with methanol. The partially purified ethyl N-[(7-amidino-2-naphthyl)methyl]-N-[4-[(4-piperidyl)oxy]phenyl]oxamate (236 mg) was dissolved in 5 ml of ethanol, and 123 mg of ethyl acetoimidate hydrochloride and 156 mg of triethylamine were added to the solution, and the mixture was stirred at room temperature for 15 hours. The reaction solution was evaporated, and the resulting residue was purified by the ODS (YMC-GEL ODS-A 120-230/70) column chromatography using methanol:water (5:95) as the eluent, followed by addition of a small amount of 1N hydrochloric acid and freeze-drying to give 194 mg of ethyl N-[4-[(1-acetoimidoyl-4-piperidyl)oxy]phenyl]-N-[(7-amidino-2-naphthyl)methyl]oxamate dihydrochloride.

Mass spectrometry data (m/z): 516 (M-2HCl+1)$^+$.

Nuclear magnetic resonance spectrum (DMSO-$d_6$, TMS internal standard) δ: 0.89 (3H, t, J=7.3 Hz), 1.60–1.73 (2H, m), 1.94–2.05 (2H, m), 2.27 (3H, s), 3.42–3.55 (2H, m), 3.64–3.72 (1H, m), 3.72–3.81 (1H, m), 3.99 (2H, q, J=7.3 Hz), 4.62–4.68 (1H, m), 5.13 (2H, s), 6.97 (2H, d, J=9.2 Hz), 7.13 (2H, d, J=9.2 Hz), 7.55 (1H, d, J=8.6 Hz), 7.83 (1H, d, J=8.6 Hz), 7.88 (1H, s), 8.05 (1H, d, J=8.6 Hz), 8.13 (1H, d, J=8.6 Hz), 8.49 (1H, s), 8.76 (1H, bs), 9.22–9.33 (3H, m), 9.50 (2H, s).

EXAMPLE 24

1-[4-[(1-Acetoimidoyl-4-piperidyl)oxy]phenyl]-1-[(7-amidino-2-naphthyl)methyl]-3-ethylurea dihydrochloride Starting compound: 1-[4-[(1-t-butoxycarbonyl-4-piperidyl)oxy]phenyl]-1-[(7-cyano-2-naphthyl)methyl]-3-ethylurea.

Mass spectrometry data (m/z): 487 (M-2HCl+1)$^+$.

Nuclear magnetic resonance spectrum (DMSO-$d_6$, TMS internal standard) δ: 0.99 (3H, t, J=7.3 Hz), 1.61–1.73 (2H, m), 1.95–2.05 (2H, m), 2.28 (3H, s), 3.01–3.13 (2H, m), 3.45–3.59 (2H, m), 3.64–3:84 (2H, m), 4.58–4.65 (1H, m), 4.97 (2H, s), 5.73 (1H, t, J=5.5 Hz), 6.93 (2H, d, J=8.6 Hz), 7.08 (2H, d, J=9.2 Hz), 7.60 (1H, d, J=8.5 Hz), 7.75–7.86 (2H, m), 8.00 (1H, d, J=8.5 Hz), 8.10 (1H, d, J=9.2 Hz), 8.46 (1H, s), 8.85 (1H, s), 9.23–9.40 (3H, m), 9.51 (2H, s).

EXAMPLE 25

Ethyl 3-[4-[(1-acetoimidoyl-4-piperidyl)oxy]phenyl]-3-[(7-amidino-2-naphthyl)methyl]ureido-1-acetate dihydrochloride Starting compound: ethyl 3-[4-[(1-t-butoxycarbonyl-4-piperidyl)oxy]phenyl]-3-[(7-cyano-2-naphthyl)methyl]ureido-1-acetate.

Mass spectrometry data (m/z): 545 (M-2HCl+1)$^+$.

Nuclear magnetic resonance spectrum (DMSO-$d_6$, TMS internal standard) δ: 1.21 (3H, t, J=6.7 Hz), 1.52–1.67 (2H, m), 1.95–2.06 (2H, m), 2.28 (3H, s), 3.44–3.58 (2H, m), 3.65–3.83 (4H, m), 4.10 (2H, q, J=6.7 Hz), 4.60–4.66 (1H, m), 4.99 (2H, s), 6.12 (1H, t, J=5.8 Hz), 6.96 (2H, d, J=8.6 Hz), 7.13 (2H, d, J=9.2 Hz), 7.63 (1H, d, J=8.6 Hz), 7.81 (1H, d, J=8.6 Hz), 7.83 (1H, s), 8.01 (1H, d, J=8.6 Hz), 8.11 (1H, d, J=8.6 Hz), 8.43 (1H, s), 8.82 (1H, s), 8.28 (2H, s), 9.33 (1H, s) 9.50 (2H, s).

EXAMPLE 26

Ethyl N-[4-[(1-acetoimidoyl-4-piperidyl)oxy]phenyl]-N-[(7-amidino-2-naphthyl)methyl]carbamate dihydrochloride Starting compound: ethyl N-[4-[(1-t-butoxycarbonyl-4-piperidyl)oxy]phenyl]-N-[(7-cyano-2-naphthyl)methyl]carbamate.

Mass spectrometry data (m/z): 488 (M-2HCl+1)⁺.

Nuclear magnetic resonance spectrum (DMSO-$d_6$, TMS internal standard) δ: 1.16 (3H, t, J=7.0 Hz), 1.61–1.77 (2H, m), 1.95–2.06 (2H, m), 2.29 (3H, s), 3.43–3.57 (2H, m), 3.65–3.75 (1H, m), 3.75–3.83 (1H, m), 4.12 (2H, q, J=7.0 Hz), 4.58–4.65 (1H, m), 5.03 (2H, s), 6.91 (2H, d, J=8.5 Hz), 7.15 (2H, d, J=8.5 Hz), 7.60 (1H, d, J=8.5 Hz), 7.82 (1H, d, J=8.5 Hz), 7.86 (1H, s), 8.03 (1H, d, J=8.5 Hz), 8.11 (1H, d, J=8.5 Hz), 8.50 (1H, s), 8.81 (1H, s), 9.33 (2H, s), 9.35 (1H, s), 9.53 (2H, s).

EXAMPLE 27

1-[4-[(1-Acetoimidoyl-4-piperidyl)oxy]phenyl]-1-[(7-amidino-2-naphthyl)methyl]-3-ethylthiourea dihydrochloride Starting compound: 1-[4-[(1-t-butoxycarbonyl-4-piperidyl)oxy]phenyl]-1-[(7-cyano-2-naphthyl)methyl]-3-ethylthiourea.

Mass spectrometry data (m/z): 503 (M-2HCl+1)⁺.

Nuclear magnetic resonance spectrum (DMSO-$d_6$, TMS internal standard) δ: 1.60 (3H, t), 1.61–1.76 (2H, m), 1.94–2.05 (2H, m), 2.28 (3H, s), 3.40–3.55 (4H, m), 3.64–3.74 (1H, m), 3.74–3.83 (1H, m), 6.97 (2H, d, J=8.9 Hz), 7.01 (1H, t, J=5.5 Hz), 7.05 (2H, d, J=8.9 Hz), 7.69 (1H, d, J=8.5 Hz), 7.81 (1H, d, J=10.4 Hz), 7.88 (1H, s), 8.00 (1H, d, J=8.5 Hz), 8.10 (1H, d, J=8.5 Hz), 8.46 (1H, s), 8.84 (1H, s), 9.28 (2H, s), 9.34 (1H, s), 9.50 (2H, s).

EXAMPLE 28

N-[4-[(1-Acetoimidoyl-4-piperidyl)oxy]phenyl]-N-[(7-amidino-2-naphthyl)methyl]ethanesulfonamide dihydrochloride Starting compound: N-[4-[(1-t-butoxycarbonyl-4-piperidyl)oxy]phenyl]-N-[(7-cyano-2-naphthyl)methyl]ethanesulfonamide.

Mass spectrometry data (m/z): 508 (M-2HCl+1)⁺.

Nuclear magnetic resonance spectrum (DMSO-$d_6$, TMS internal standard) δ: 1.33 (3H, t, J=7.3 Hz), 1.59–1.73 (2H, m), 1.93–2.03 (2H, m), 2.27 (3H, s), 3.26 (2H, q, J=7.3 Hz), 3.43–3.54 (2H, m), 3.63–3.71 (1H, m), 3.71–3.80 (1H, m), 4.58–4.64 (1H, m), 5.07 (2H, s), 6.91 (2H, d, J=9.2 Hz), 7.33 (2H, d, J=9.2 Hz), 7.65 (1H, d, J=8.5 Hz), 7.81 (1H, d, J=8.5 Hz), 7.90 (1H, s), 8.01 (1H, d, J=8.5 Hz), 8.09 (1H, d, J=9.2 Hz), 8.47 (1H, s), 8.74 (1H, s), 9.26 (2H, s), 9.28 (1H, s), 9.50 (2H, s).

EXAMPLE 29

Ethyl N-[4-[(1-acetoimidoyl-4-piperidyl)oxy]phenyl]-N-[(7-amidino-2-naphthyl)methyl]oxamate obtained in Example 23 (100 mg) was dissolved in 20 ml of concentrated hydrochloric acid and the solution was allowed to stand at 5° C. for 9 days. The reaction solution was evaporated, and the resulting residue was purified by an ODS (YMC-GEL ODS-A 120-230/70) column chromatography using methanol:water (3:97) as the eluent, followed by addition of a small amount of 1N hydrochloric acid and freeze-drying to give 23 mg of N-[4-[(1-acetoimidoyl-4-piperidyl)oxy]phenyl]-N-[(7-amidino-2-naphthyl)methyl]oxamic acid dihydrochloride.

Mass spectrometry data (m/z): 488 (M-2HCl+1)⁺.

Nuclear magnetic resonance spectrum (DMSO-$d_6$, TMS internal standard) δ: 1.60–1.75 (2H, m), 1.94–2.04 (2H, m), 2.27 (3H, s), 3.40–3.52 (2H, m), 3.64–3.81 (2H, m), 4.57–4.65 (1H, m), 5.09 (2H, s), 6.94 (2H, d, J=8.5 Hz), 7.16 (2H, d, J=8.5 Hz), 7.56 (1H, d, J=9.2 Hz), 7.82 (1H, d, J=9.2 Hz), 7.89 (1H, s), 8.04 (1H, d, J=8.5 Hz), 8.12 (1H, d, J=8.5 Hz), 8.46 (1H, s), 8.72 (1H, s), 9.17–9.30 (3H, m), 9.46 (2H, s), 14.0 (1H, bs).

EXAMPLE 30

Ethyl 3-[4-[(1-acetoimidoyl-4-piperidyl)oxy]phenyl]-3-[(7-amidino-2-naphthyl)methyl]ureido-1-acetate dihydrochloride obtained in Example 25 (109 mg) was dissolved in 20 ml of 1N hydrochloric acid and the solution was heated under reflux for 10 minutes. The reaction solution was evaporated, and the resulting residue was purified by an ODS (YMC-GEL ODS-A 120-230/70) column chromatography using methanol:water (5:95) as the eluent, followed by addition of a small amount of 1N hydrochloric acid and freeze-drying to give 74 mg of 3-[4-[(1-acetoimidoyl-4-piperidyl)oxy]phenyl]-3-[(7-amidino-2-naphthyl)methyl]ureido-1-acetic acid dihydrochloride.

Mass spectrometry-data (m/z): 517 (M-2HCl+1)⁺.

Nuclear magnetic resonance spectrum (DMSO-$d_6$, TMS internal standard) δ: 1.62–1.78 (2H, m), 1.93–2.08 (2H, m), 2.28 (3H, s), 3.40–3.85 (6H, m), 4.58–4.68 (1H, m), 4.99 (2H, s), 6.01 (1H, t, J=5.6 Hz), 6.96 (2H, d, J=8.8 Hz), 7.14 (2H, d, J=8.8 Hz), 7.62 (1H, d, J=8.3 Hz), 7.81 (1H, d, J=8.8 Hz), 7.86 (1H, s), 8.01 (1H, d, J=8.3 Hz), 8.11 (1H, d, J=8.8 Hz), 8.84 (1H, s), 9.31 (2H, s), 9.35 (1H, s), 9.51 (2H, s).

The following compound was obtained in the same manner as described in Example 23.

EXAMPLE 31

7-[[4-[(1-Acetoimidoyl-4-piperidyl)oxy]anilino]methyl]-2-naphthamidine trihydrochloride Starting compound: 7-[[4-[(1-t-butoxycarbonyl-4-piperidyl)oxy]anilino]methyl]-2-naphthalenecarbonitrile.

Mass spectrometry data (m/z): 416 (M-3HCl+1)⁺.

Nuclear magnetic resonance spectrum (DMSO-$d_6$, TMS internal standard) δ: 1.60–1.73 (2H, m), 1.88–1.99 (2H, m), 2.27 (3H, s), 3.42–3.55 (2H, m), 3.63–3.77 (2H, m), 4.35–4.42 (1H, m), 4.45 (2H, d, J=6.1 Hz), 6.16 (1H, d, J=6.1 Hz), 6.55 (2H, d, J=8.5 Hz), 6.75 (2H, d, J=8.5 Hz), 7.74 (1H, d, J=8.5 Hz), 7.79 (2H, d, J=8.5 Hz), 7.99 (1H, s), 8.03 (1H, d, J=8.5 Hz), 8.11 (1H, d, J=8.5 Hz), 8.43 (1H, s), 9.0–9.6 (8H, br).

EXAMPLE 32

N-[4-[(1-t-Butoxycarbonyl-4-piperidyl)oxy]phenyl]-N-[(7-cyano-2-naphthyl)methyl]-2-methoxybenzamide obtained in Reference Example 19 (80 mg) was dissolved in 5 ml of ethanol. While stirring, this solution was cooled to −70° C. and hydrogen chloride was introduced until saturation. The reaction solution was stirred at 5° C. for 16 hours and then evaporated. The resulting residue was dissolved in 5 ml of ethanol, 52 mg of ammonium acetate was added, and the mixture was stirred at room temperature for 3 days. The reaction solution was evaporated, and the resulting residue was purified by an ODS (YMC-GEL ODS-A RO-230/70) column chromatography using methanol:water (100:0) as the eluent, followed by addition of a small amount of 1N hydrochloric acid and freeze-drying to give 80 mg of N-[(7-amidino-2-naphthyl)methyl]-N-[[(4-piperidyl)oxy]phenyl]-2-methoxybenzamide dihydrochloride.

Mass spectrometry data (m/z): 509 (M-2HCl+1)⁺.

Nuclear magnetic resonance spectrum (DMSO-$d_6$, TMS internal standard) δ: 1.62–1.74 (2H, m), 1.90–2.00 (2H, m), 2.87–3.00 (2H, m), 3.02–3.14 (2H, m), 3.81 (3H, s), 4.41–4.50 (1H, m), 5.22 (2H, s), 6.69 (2H, d, J=9.2 Hz), 6.83 (2H, d, J=8.6 Hz), 6.95 (2H, d, J=9.2 Hz), 7.20–7.24 (1H, m), 7.27 (1H, d, J=7.9 Hz), 7.73–7.75 (1H, m), 7.84 (1H, d, J=8.6 Hz), 7.99 (1H, s), 8.07 (1H, d, J=8.6 Hz), 8.13 (1H, d, J=8.5 Hz), 8.50 (1H, s), 9.10 (1H, brs), 9.20 (1H, brs), 9.36 (2H, s), 9.57 (2H, s).

The following compound of Example 33 was obtained in the same manner as described in Example 12.

EXAMPLE 33

N-[4-[(1-Acetoimidoyl-4-piperidyl)oxy]phenyl]-N-[(7-amidino-2-naphthyl)methyl]-2-methoxybenzamide dihydrochloride Starting compound: N-[(7-amidino-2-naphthyl)methyl]-N-[[(4-piperidyl)oxy]phenyl]-2-methoxybenzamide dihydrochloride.

Mass spectrometry data (m/z): 550 (M-2HCl+1)$^+$.

Nuclear magnetic resonance spectrum (DMSO-$d_6$, TMS internal standard) δ: 1.44–1.62 (2H, m), 1.82–1.86 (2H, m), 2.26 (3H, s), 3.40–3.46 (2H, m), 3.63–3.79 (2H, m), 3.70 (3H, m), 4.46–4.50 (1H, m), 5.23 (2H, s), 6.69 (2H, d, J=9.2 Hz), 6.83 (2H, d, J=7.9 Hz), 6.95 (2H, d, J=8.5 Hz), 7.20 (1H, t, J=8.6 Hz), 7.27 (1H, d, J=7.3 Hz), 7.23 (1H, d, J=8.6 Hz), 7.85 (1H, d, J=8.5 Hz), 7.99 (1H, s), 8.08 (1H, d, J=8.6 Hz), 8.13 (1H, d, J=8.5 Hz), 8.52 (1H, s), 8.86 (1H, s), 9.41 (3H, s), 9.60 (2H, s).

The following compound of Example 34 was obtained in the same manner as described in Example 32.

EXAMPLE 34

N-[(7-Amidino-2-naphthyl)methyl]-N-[[(4-piperidyl)oxy]phenyl]-4-methoxybenzamide dihydrochloride Starting compound: N-[4-[(1-t-butoxycarbonyl-4-piperidyl)oxy]phenyl]-N-[(7-cyano-2-naphthyl)methyl]-4-methoxybenzamide.

Mass spectrometry data (m/z): 509 (M-2HCl+1)$^+$.

Nuclear magnetic resonance spectrum (DMSO-$d_6$, TMS internal standard) δ: 1.70–1.81 (2H, m), 1.96–2.07 (2H, m), 2.96–3.00 (2H, m), 3.07–3.18 (2H, m), 3.71 (3H, s), 4.48–4.56 (1H, m), 5.26 (2H, s), 6.79 (2H, d, J=8.6 Hz), 6.82 (2H, d, J=9.2 Hz), 7.03 (2H, d, J=8.6 Hz), 7.31 (2H, d, J=8.6 Hz), 7.67 (1H, d, J=9.8 Hz), 7.84 (1H, d, J=6.7 Hz), 7.95 (1H, s), 8.02 (1H, d, J=8.5 Hz), 8.10 (1H, d, J=8.5 Hz), 8.54 (1H, s), 9.24 (1H, brs), 9.33 (1H, brs), 9.41 (2H, s), 9.58 (2H, s).

The following compound of Example 35 was obtained in the same manner as described in Example 12.

EXAMPLE 35

N-[4-[(1-Acetoimidoyl-4-piperidyl)oxy]phenyl]-N-[(7-amidino-2-naphthyl)methyl]-4-methoxybenzamide dihydrochloride Starting compound: N-[(7-amidino-2-naphthyl]methyl]-N-[4-(4-piperidyl)oxy]phenyl]-4-methoxybenzamide dihydrochloride.

Mass spectrometry data (m/z): 550 (M-2HCl+1)$^+$.

Nuclear magnetic resonance spectrum (DMSO-$d_6$, TMS internal standard) δ: 1.55–1.68 (2H, m), 1.86–2.00 (2H, m), 2.27 (3H, s), 3.41–3.49 (2H, m), 3.66–3.78 (2H, m), 3.72 (3H, s), 4.54–4.60 (1H, m), 5.26 (2H, s), 6.79 (2H, d, J=9.2 Hz), 6.82 (2H, d, J=9.2 Hz), 7.03 (2H, d, J=8.5 Hz), 7.31 (2H, d, J=8.6 Hz), 7.68 (1H, t, J=10.4 Hz), 7.82 (1H, d, J=8.5 Hz), 7.95 (1H, s), 8.02 (1H, d, J=8.5 Hz), 8.10 (1H, d, J=8.6 Hz), 8.52 (1H, s), 8.85 (1H, s), 9.37 (3H, s), 9.55 (2H, s).

The following compound of Example 36 was obtained in the same manner as described in Example 32.

EXAMPLE 36

N-[(7-Amidino-2-naphthyl)methyl]-N-[4-[(4-piperidyl)oxy]phenyl]-4-pyridinecarboxamide trihydrochloride Starting compound: N-[4-[(1-t-butoxycarbonyl-4-piperidyl)oxy]phenyl]-N-[(7-cyano-2-naphthyl)methyl]-4-pyridinecarboxamide.

Mass spectrometry data (m/z): 480 (M-3HCl+1)$^+$.

Nuclear magnetic resonance spectrum (DMSO-$d_6$, TMS internal standard) δ: 1.68–1.78 (2H, m), 1.92–2.01 (2H, m), 2.84–3.00 (2H, m), 3.02–3.18 (2H, m), 4.44–4.57 (1H, m), 5.30 (2H, s), 6.80 (2H, d, J=9.2 Hz), 7.15 (2H, d, J=8.5 Hz), 7.74 (1H, d, J=8.6 Hz), 7.85–7.87 (3H, m), 8.01 (1H, s), 8.05 (1H, d, J=8.5 Hz), 8.13 (1H, d, J=8.5 Hz), 8.60 (1H, s), 8.78 (2H, brs), 9.28 (2H, brs), 9.37 (1H, brs), 9.44 (2H, s), 9.62 (2H, s)

The following compound of Example 37 was obtained in the same manner as described in Example 12.

EXAMPLE 37

N-[4-[(1-Acetoimidoyl-4-piperidyl)oxy]phenyl]-N-[(7-amidino-2-naphthyl)methyl]-4-pyridinecarboxamide trihydrochloride Starting compound: N-[(7-amidino-2-naphthyl]methyl]-N-[4-[(4-piperidyl)oxy]phenyl]-4-pyridinecarboxamide trihydrochloride.

Mass spectrometry data (m/z): 521 (M-3HCl+1)$^+$.

Nuclear magnetic resonance spectrum (DMSO-$d_6$, TMS internal standard) δ: 1.55–1.62 (2H, m), 1.92–2.02 (2H, m), 2.28 (3H, s), 3.40–3.50 (2H, m), 3.64–3.81 (2H, m), 4.54–4.57 (1H, m), 5.31 (2H, s), 6.81 (2H, d, J=8.5 Hz), 7.16 (2H, d, J=8.5 Hz), 7.75 (1H, d, J=8.5 Hz), 7.87 (1H, d, J=8.5 Hz), 8.00 (2H, br), 8.06 (1H, d, J=8.5 Hz), 8.13 (1H, d, J=8.5 Hz), 8.63 (1H, s), 8.46 (2H, br), 8.85 (1H, s), 9.50 (3H, s), 9.68 (2H, s).

The following compound of Example 38 was obtained in the same manner as described in Example 32.

EXAMPLE 38

N-[(7-Amidino-2-naphthyl)methyl]-N-[4-[(4-piperidyl)oxy]phenyl]-2-pyridinecarboxamide trihydrochloride Starting compound: N-[4-[(1-t-butoxycarbonyl-4-piperidyl)oxy]phenyl]-N-[(7-cyano-2-naphthyl)methyl]-2-pyridinecarboxamide.

Mass spectrometry data (m/z): 480 (M-3HCl+1)$^+$.

Nuclear magnetic resonance spectrum (DMSO-$d_6$, TMS internal standard) δ: 1.62–1.78 (2H, m), 1.89–2.05 (2H, m), 2.88–3.00 (2H, m), 3.04–3.16 (2H, m), 4.00–4.10 (1H, m), 5.28 (2H, s), 6.75 (2H, d, J=8.5 Hz), 7.03 (2H, d, J=8.5 Hz), 7.32–7.41 (1H, m), 7.56–7.64 (1H, m), 7.73 (1H, d, J=8.6 Hz), 7.76 (1H, d, J=8.6 Hz), 7.80–7.89 (1H, m), 8.00 (1H, s), 8.05–8.09 (1H, m), 8.09 (1H, d, J=8.5 Hz), 8.43 (1H, s), 8.56 (1H, s), 9.12 (2H, brs), 9.26 (3H, brs), 9.38 (2H, s), 9.57 (2H, s).

The following compound of Example 39 was obtained in the same manner as described in Example 12.

EXAMPLE 39

N-[4-[(1-Acetoimidoyl-4-piperidyl)oxy]phenyl]-N-[(7-amidino-2-naphthyl)methyl]-2-pyridinecarboxamide trihydrochloride Starting compound: N-[(7-amidino-2-naphthyl)methyl]-N-[4-[(4-piperidyl)oxy]phenyl]-2-pyridinecarboxamide trihydrochloride.

Mass spectrometry data (m/z): 521 (M-3HCl+1)$^+$.

Nuclear magnetic resonance spectrum (DMSO-$d_6$, TMS internal standard) δ: 1.52–1.64 (2H, m), 1.86–1.97 (2H, m), 2.25 (3H, s), 3.36–3.48 (2H, m), 3.60–3.79 (2H, m), 4.46–4.52 (1H, m), 5.27 (2H, s), 6.67–6.75 (2H, br), 6.91–7.00 (2H, m), 7.22–7.28 (1H, br), 7.51–7.58 (1H, br), 7.72 (1H, d, J=8.5 Hz), 7.76 (2H, d, J=7.9 Hz), 7.95 (1H, s), 8.02–8.04 (1H, br), 8.09 (1H, d, J=8.5 Hz), 8.36 (1H, s), 8.57 (1H, s), 8.72 (1H, s), 9.28 (3H, s), 9.50 (2H, s).

The following compound of Example 40 was obtained in the same manner as described in Example 32.

EXAMPLE 40

N-[(7-Amidino-2-naphthyl)methyl]-N-[4-[(4-piperidyl)oxy]phenyl]-2-methoxyacetamide dihydrochloride Starting compound: N-[4-[(1-t-butoxycarbonyl-4-piperidyl)oxy]phenyl]-N-[(7-cyano-2-naphthyl)methyl]-2-methoxyacetamide.

Mass spectrometry data (m/z): 447 (M-2HCl+1)$^+$.

Nuclear magnetic resonance spectrum (DMSO-$d_6$, TMS internal standard) δ: 1.78–1.84 (2H, m), 2.01–2.10 (2H, m), 2.97–3.05 (2H, m), 3.10–3.19 (2H, m), 3.83 (3H, s), 4.57–4.62 (1H, m), 5.00 (2H, s), 6.95 (2H, d, J=9.2 Hz), 7.15 (2H, d, J=8.5 Hz), 7.59 (1H, d, J=8.6 Hz), 7.82 (1H, d, J=6.7 Hz), 7.86 (1H, s), 8.01 (1H, d, J=8.6 Hz), 8.11 (1H, d, J=8.6 Hz), 8.48 (1H, s), 9.19 (1H, brs), 9.26 (1H, brs), 9.35 (2H, s), 9.54 (2H, s).

The following compound of Example 41 was obtained in the same manner as described in Example 12.

EXAMPLE 41

N-[4-[(1-Acetoimidoyl-4-piperidyl)oxy]phenyl]-N-[(7-amidino-2-naphthyl)methyl]-2-methoxyacetamide dihydrochloride Starting compound: N-[(7-amidino-2-naphthyl)methyl]-N-[4-[(4-piperidyl)oxy]phenyl]-2-methoxyacetanilide dihydrochloride.

Mass spectrometry data (m/z): 488 (M-2HCl+1)$^+$.

Nuclear magnetic resonance spectrum (DMSO-$d_6$, TMS internal standard) δ: 1.60–1.78 (2H, m), 1.96–2.03 (2H, m), 2.28 (3H, s), 3.25 (3H, s), 3.40–3.58 (2H, m), 3.60–3.75 (2H, m), 3.83 (2H, s), 4.60–4.68 (1H, m), 5.03 (2H, s), 6.95 (2H, d, J=9.2 Hz), 7.15 (2H, d, J=8.5 Hz), 7.59 (1H, d, J=8.6 Hz), 7.82 (1H, d, J=8.5 Hz), 7.86 (1H, s), 8.02 (1H, d, J=8.5 Hz), 8.11 (1H, d, J=8.6 Hz), 8.46 (1H, s), 8.83 (1H, s), 8.33 (3H, s), 9.53 (2H, s).

The following compound of Example 42 was obtained in the same manner as described in Example 32.

EXAMPLE 42

Ethyl N-[(7-amidino-2-naphthyl)methyl]-N-[4-[(4-piperidyl)oxy]phenyl]malonamate dihydrochloride Starting compound: ethyl N-[4-[(1-t-butoxycarbonyl-4-piperidyl)oxy]phenyl]-N-[(7-cyano-2-naphthyl)methyl]malonamate dihydrochloride.

Mass spectrometry data (m/z): 489 (M-2HCl+1)$^+$.

Nuclear magnetic resonance spectrum (DMSO-$d_6$, TMS internal standard) δ: 1.37 (3H, t, J=6.7 Hz), 1.74–1.83 (2H, m), 2.01–2.10 (2H, m), 2.96–3.03 (2H, m), 3.10–3.21 (2H, m), 3.30 (2H, s), 4.02 (2H, q, J=7.3 Hz), 4.56–4.62 (1H, m), 5.05 (2H, s), 6.96 (2H, d, J=8.6 Hz), 7.14 (2H, d, J=6.1 Hz), 7.63 (1H, d, J=6.7 Hz), 7.76 (1H, d, J=7.3 Hz), 7.85 (1H, s), 8.03 (1H, d, J=8.5 Hz), 8.11 (1H, d, J=8.6 Hz), 8.49 (1H, s), 9.20 (1H, brs), 9.29 (1H, brs), 9.39 (2H, s), 9.57 (2H, s).

The following compound of Example 43 was obtained in the same manner as described in Example 12.

EXAMPLE 43

Ethyl N-[4-[(1-acetoimidoyl-4-piperidyl)oxy]phenyl]-N-[(7-amidino-2-naphthyl)methyl]malonamate dihydrochloride Starting compound: ethyl N-[(7-amidino-2-naphthyl)methyl]-N-[4-[(4-piperidyl)oxy]phenyl]malonamate dihydrochloride.

Mass spectrometry data (m/z): 530 (M-2HCl+1)$^+$.

Nuclear magnetic resonance spectrum (DMSO-$d_6$, TMS internal standard) δ: 1.14 (3H, t, J=7.3 Hz), 1.60–1.75 (2H, m), 1.95–2.06 (2H, m), 2.27 (3H, s), 3.29 (2H, s), 3.38–3.55 (2H, m), 3.64–3.83 (2H, m), 4.01 (2H, q, J=7.3 Hz), 4.60–4.64 (1H, m), 5.07 (2H, s), 6.96 (2H, d, J=8.6 Hz), 7.13 (2H, d, J=9.2 Hz), 7.62 (1H, d, J=8.5 Hz), 7.81 (1H, d, J=8.5 Hz), 7.87 (1H, s), 8.03 (1H, d, J=8.5 Hz), 8.12 (1H, d, J=8.6 Hz), 8.43 (1H, s), 8.76 (1H, s), 8.26 (3H, s), 9.50 (2H, s).

The following compound of Example 44 was obtained in the same manner as described in Example 32.

EXAMPLE 44

Ethyl N-[(7-amidino-2-naphthyl)methyl]-N-[4-[(4-piperidyl)oxy]phenyl]succinamate dihydrochloride Starting compound: ethyl N-[4-[(1-t-butoxycarbonyl-4-piperidyl)oxy]phenyl]-N-[(7-cyano-2-naphthyl)methyl]succinamate dihydrochloride.

Mass spectrometry data (m/z): 503 (M-2HCl+1)$^+$.

Nuclear magnetic resonance spectrum (DMSO-$d_6$, TMS internal standard) δ: 1.18 (3H, t, J=6.7 Hz), 1.78–1.84 (2H, m), 2.04–2.14 (2H, m), 2.34 (2H, t, J=6.1 Hz), 2.56 (2H, t, J=6.1 Hz), 2.94–3.06 (2H, m), 3.12–3.22 (2H, m), 4.06 (2H, q, J=6.7 Hz), 4.56–4.64 (1H, m), 5.03 (2H, s), 6.98 (2H, d, J=9.2 Hz), 7.15 (2H, d, J=8.6 Hz), 7.58 (1H, d, J=9.2 Hz), 7.83–7.85 (2H, m), 8.01 (1H, d, J=8.6 Hz), 8.08–8.12 (1H, m), 8.48 (1H, s), 9.29 (1H, brs), 9.38 (1H, brs), 9.41 (2H, s), 9.58 (2H, s).

The following compound of Example 45 was obtained in the same manner as described in Example 12.

EXAMPLE 45

Ethyl N-[4-[(1-acetoimidoyl-4-piperidyl)oxy]phenyl]-N-[(7-amidino-2-naphthyl)methyl]succinate dihydrochloride Starting compound: ethyl N-[(7-amidino-2-naphthyl)methyl]-N-[4-[(4-piperidyl)oxy]phenyl]succinamate dihydrochloride.

Mass spectrometry data (m/z): 544 (M-2HCl+1)$^+$.

Nuclear magnetic resonance spectrum (DMSO-$d_6$, TMS internal standard) δ: 1.18 (3H, t, J=6.7 Hz), 1.61–1.76 (2H, m), 1.96–2.08 (2H, m), 2.29 (3H, s), 2.34 (2H, t, J=6.1 Hz), 2.55 (2H, t, J=6.1 Hz), 3.43–3.55 (2H, m), 3.64–3.86 (2H, m), 4.06 (2H, q, J=6.7 Hz), 4.60–4.69 (1H, m), 5.03 (2H, s), 6.98 (2H, d, J=9.15 Hz), 7.14 (2H, d, J=8.6 Hz), 7.58 (1H, d, J=8.5 Hz), 7.80–7.92 (2H, m), 8.01 (1H, d, J=8.6 Hz), 8.11 (1H, d, J=8.6 Hz), 8.48 (1H, s), 8.93 (1H, s), 9.43 (3H, s), 9.59 (2H, s).

The following compound of Example 46 was obtained in the same manner as described in Example 32.

EXAMPLE 46

N-[(7-Amidino-2-naphthyl)methyl]-N-[4-[(4-piperidyl)oxy]phenyl]-2,6-difluorobenzamide dihydrochloride Starting compound: N-[4-[(1-t-butoxycarbonyl-4-piperidyl)oxy]phenyl]-N-[(7-cyano-2-naphthyl)methyl]-2,6-difluorobenzamide dihydrochloride.

Mass spectrometry data (m/z): 515 (M-2HCl+1)$^+$.

Nuclear magnetic resonance spectrum (DMSO-$d_6$, TMS internal standard) δ: 1.64–1.72 (2H, m), 1.91–2.00 (2H, m), 2.87–3.00 (2H, m), 3.02–3.17 (2H, m), 4.41–4.50 (1H, m), 5.27 (1H, s), 6.79 (2H, d, J=8.6 Hz), 6.97–7.03 (4H, m), 7.35–7.38 (1H, m), 7.67 (1H, d, J=9.8 Hz), 7.86 (1H, d, J=8.6 Hz), 7.93 (1H, s), 8.10 (1H, d, J=8.5 Hz), 8.14 (1H, d, J=8.6 Hz), 8.47 (1H, s), 9.08 (1H, brs), 9.19 (1H, brs), 9.34 (2H, s), 9.55 (2H, s).

The following compound of Example 47 was obtained in the same manner as described in Example 12.

EXAMPLE 47

N-[4-[(1-Acetoimidoyl-4-piperidyl)oxy]phenyl]-N-[(7-amidino-2-naphthyl)methyl]-2,6-difluorobenzamide dihydrochloride Starting compound: N-[(7-amidino-2-naphthyl)methyl]-N-[4-[(4-piperidyl)oxy]phenyl]-2,6-difluorobenzamide dihydrochloride.

Mass spectrometry data (m/z): 556 (M-2HCl+1)$^+$.

Nuclear magnetic resonance spectrum (DMSO-$d_6$, TMS internal standard) δ: 1.54–1.61 (2H, m), 1.85–1.96 (2H, m), 2.28 (3H, s), 3.38–3.45 (2H, m), 3.63–3.73 (2H, m), 4.50–4.57 (1H, m), 5.26 (2H, s), 6.80 (2H, d, J=9.2 Hz), 6.97–7.03 (4H, m), 7.34–7.38 (1H, m), 7.67 (1H, d, J=8.5 Hz), 7.84 (1H, d, J=8.5 Hz), 7.93 (1H, s), 8.09 (1H, d, J=8.5 Hz), 8.14 (1H, d, J=8.6 Hz), 8.46 (1H, s), 8.75 (1H, s), 9.28 (3H, s), 9.52 (2H, s).

The following compound of Example 48 was obtained in the same manner as described in Example 32.

EXAMPLE 48

N-[(7-Amidino-2-naphthyl)methyl]-N-[4-[(4-piperidyl)oxy]phenyl]-2-dimethylaminoacetamide trihydrochloride Starting compound: N-[4-[(1-t-butoxycarbonyl-4-piperidyl)oxy]phenyl]-N-[(7-cyano-2-naphthyl)methyl]-2-dimethylaminoacetamide.

Mass spectrometry-data (m/z): 460 (M-3HCl+1)$^+$.

Nuclear magnetic resonance spectrum (DMSO-$d_6$, TMS internal standard) δ: 1.77–1.89 (2H, m), 2.01–2.14 (2H, m), 2.82 (6H, s), 2.96–3.08 (2H, m), 3.11–3.23 (2H, m), 3.97 (2H, s), 4.41–4.45 (1H, m), 5.07 (2H, s), 7.02 (2H, d, J=9.3 Hz), 7.22 (2H, d, J=8.8 Hz), 7.50 (1H, d, J=8.8 Hz), 7.79 (1H, s), 7.94–7.96 (3H, m), 8.45 (1H, s), 9.43 (2H, brs), 9.49 (1H, brs), 9.99 (4H, s).

The following compound of Example 49 was obtained in the same manner as described in Example 12.

EXAMPLE 49

N-[4-[(1-Acetoimidoyl-4-piperidyl)oxy]phenyl]-N-[(7-amidino-2-naphthyl)methyl]-2-dimethylaminoacetamide trihydrochloride Starting compound: N-[(7-amidino-2-naphthyl)methyl]-N-[4-[(4-piperidyl)oxy]phenyl]-2-dimethylaminoacetamide trihydrochloride.

Mass spectrometry data (m/z): 501 (M-3HCl+1)$^+$.

Nuclear magnetic resonance spectrum (DMSO-$d_6$, TMS internal standard) δ: 1.64–1.73 (2H, m), 1.93–2.10 (2H, m), 2.31 (3H, s), 2.82 (6H, s), 3.46–3.61 (2H, m), 3.69–3.86 (2H, m), 3.98 (2H, s), 4.68–4.69 (1H, m), 5.24 (2H, s), 7.02 (2H, d, J=8.8 Hz), 7.21 (2H, d, J=8.8 Hz), 7.43–7.55 (2H, m), 7.78 (1H, s), 7.93–7.95 (2H, m), 8.11–8.18 (1H, brs), 8.45 (1H, s), 9.05 (1H, s), 9.54 (1H, s), 10.03 (1H, s).

The following compound of Example 50 was obtained in the same manner as described in Example 32.

EXAMPLE 50

Ethyl N-[(7-amidino-2-naphthyl)methyl]carbamoyl]-N-[N-[4-(4-piperidyl)oxy]phenyl]carbonate dihydrochloride Starting compound: ethyl N-[N-[4-(1-t-butoxycarbonyl-4-piperidyl)oxy]phenyl]-N-[(7-cyano-2-naphthyl)methyl]carbamoyl]carbonate.

Mass spectrometry data (m/z): 490 (M-2HCl+1)$^+$.

Nuclear magnetic resonance spectrum (DMSO-$d_6$, TMS internal standard) δ: 1.12 (3H, t, J=6.7 Hz), 1.74–1.82 (2H, m), 2.01–2.10 (2H, m), 2.98–3.03 (2H, m), 3.10–3.19 (2H, m), 4.01 (2H, q, J=6.7 Hz), 4.56–4.62 (1H, m), 5.02 (2H, s), 6.93 (2H, d, J=9.2 Hz), 7.13 (2H, d, J=8.5 Hz), 7.62 (1H, d, J=8.5 Hz), 7.75 (1H, d, J=6.7 Hz), 7.86 (1H, s), 8.00 (1H, d, J=8.6 Hz), 8.07 (1H, d, J=7.9 Hz), 8.51 (1H, s), 8.89 (1H, s), 9.12 (1H, brs), 9.20 (1H, brs), 9.32 (2H, s), 9.51 (2H, s).

The following compound of Example 51 was obtained in the same manner as described in Example 12.

EXAMPLE 51

Ethyl N-[N-[4-(1-acetoimidoyl-4-piperidyl)oxy]phenyl]-N-[(7-amidino-2-naphthyl)methyl]carbamoyl]carbonate dihydrochloride Starting compound: ethyl N-[(7-amidino-2-naphthyl)methyl]carbamoyl]-N-[N-[4-(4-piperidyl)oxy]phenyl]carbonate dihydrochloride.

Mass spectrometry data (m/z): 531 (M-2HCl+1)$^+$.

Nuclear magnetic resonance spectrum (DMSO-$d_6$, TMS internal standard) δ: 1.12 (3H, t, J=7.3 Hz), 1.71–1.75 (2H, m), 1.94–2.08 (2H, m), 2.28 (3H, s), 3.48–3.54 (2H, m), 3.69–3.83 (2H, m), 4.01 (2H, q, J=7.3 Hz), 4.60–4.68 (1H, m), 5.03 (2H, s), 6.94 (2H, d, J=9.3 Hz), 7.12 (2H, d, J=8.8 Hz), 7.60 (1H, d, J=9.8 Hz), 7.81 (1H, d, J=6.8 Hz), 7.90 (1H, s), 8.01 (1H, d, J=8.8 Hz), 8.11 (1H, d, J=8.8 Hz), 8.45 (1H, s), 8.82 (1H, s), 8.97 (1H, s), 9.29 (3H, s), 9.52 (2H, s).

The following compound of Example 52 was obtained in the same manner as described in Example 32.

EXAMPLE 52

N-[(7-Amidino-2-naphthyl)methyl]-N-[4-[(4-piperidyl)oxy]phenyl]benzenesulfonamide dihydrochloride Starting compound: N-[4-[(1-t-butoxycarbonyl-4-piperidyl)oxy]phenyl]-N-[(7-cyano-2-naphthyl)methyl]benzenesulfonamide.

Mass spectrometry data (m/z): 515 (M-2HCl+1)$^+$.

Nuclear magnetic resonance spectrum (DMSO-d$_6$, TMS internal standard) δ: 1.68–1.80 (2H, m), 1.97–2.07 (2H, m), 2.93–3.06 (2H, m), 3.10–3.22 (2H, m), 4.50–4.57 (1H, m), 4.99 (2H, s), 6.84 (2H, d, J=8.5 Hz), 6.98 (2H, d, J=9.2 Hz), 7.64–7.72 (5H, m), 7.76 (1H, t, J=7.3 Hz), 7.81 (1H, d, J=8.5 Hz), 7.92 (1H, s), 8.01 (1H, d, J=8.6 Hz), 8.08 (1H, d, J=8.6 Hz), 8.45 (1H, s), 9.04 (1H, brs), 9.11 (1H, brs), 9.28 (2H, s), 9.50 (2H, s).

The following compound of Example 53 was obtained in the same manner as described in Example 12.

EXAMPLE 53

N-[4-[(1-Acetoimidoyl-4-piperidyl)oxy]phenyl]-N-[(7-amidino-2-naphthyl)methyl]benzenesulfonamide dihydrochloride Starting compound: N-[(7-amidino-2-naphthyl]methyl]-N-[4-[(4-piperidyl)oxy]phenyl]benzenesulfonamide dihydrochloride.

Mass spectrometry data (m/z): 556 (M-2HCl+1)$^+$.

Nuclear magnetic resonance spectrum (DMSO-d$_6$, TMS internal standard) δ: 1.58–1.70 (2H, m), 1.91–2.03 (2H, m), 2.27 (3H, s), 3.42–3.49 (2H, m), 3.67–3.77 (2H, m), 4.58–4.61 (1H, m), 4.99 (2H, s), 6.84 (2H, d, J=9.2 Hz), 6.98 (2H, d, J=8.5 Hz), 7.64–7.76 (6H, m), 7.82 (1H, d, J=10.4 Hz), 7.92 (1H, s), 8.01 (1H, d, J=8.6 Hz), 8.09 (1H, d, J=8.5 Hz), 8.46 (1H, s), 8.81 (1H, s), 9.34 (3H, s), 9.53 (2H, s).

The following compound of Example 54 was obtained in the same manner as described in Example 23.

EXAMPLE 54

N-[4-[(1-Acetoimidoyl-4-piperidyl)oxy]phenyl]-N-[(7-amidino-2-naphthyl)methyl]methanesulfonamide dihydrochloride Starting compound: N-[4-[(1-t-butoxycarbonyl-4-piperidyl)oxy]phenyl]-N-[t7-cyano-2-naphthyl)methyl]methanesulfonamide.

Mass spectrometry data (m/z): 494 (M-2HCl+1)$^+$.

Nuclear magnetic resonance spectrum (DMSO-d$_6$, TMS internal standard) δ: 1.60–1.74 (2H, m), 1.94–2.03 (2H, m), 2.27 (3H, s), 3.13 (3H, s), 3.43–4.55 (2H, m), 3.63–3.73 (1H, m), 3.73–3.80 (1H, m), 4.60–4.65 (1H, m), 5.03 (2H, s), 6.93 (2H, d, J=9.2 Hz), 7.34 (2H, d, J=8.5 Hz), 7.66 (1H, dd, J=8.6, 1.2 Hz), 7.81 (1H, dd, J=8.6, 1.8 Hz), 7.91 (1H, s), 8.01 (1H, d, J=8.6 Hz), 8.09 (1H, d, J=8.5 Hz), 8.47 (1H, s), 8.74 (1H, s), 9.20–9.11 (3H, m), 9.48 (2H, s).

The following compound of Example 55 was obtained in the same manner as described in Example 23.

EXAMPLE 55

N-[4-[(1-Acetoimidoyl-4-piperidyl)oxy]phenyl]-N-[(7-amidino-2-naphthyl)methyl]benzylsulfonamide dihydrochloride Starting compound: N-[4-[(1-t-butoxycarbonyl-4-piperidyl)oxy]phenyl]-N-[(7-cyano-2-naphthyl)methyl]benzylsulfonamide.

Mass spectrometry data (m/z): 570 (M-2HCl+1)$^+$.

Nuclear magnetic resonance spectrum (DMSO-d$_6$, TMS internal standard) δ: 1.61–1.74 (2H, m), 1.94–2.04 (2H, m), 2.27 (3H, s), 3.42–3.55 (2H, m), 3.64–3.80 (2H, m), 4.58–4.62 (1H, m), 4.62 (2H, s), 4.97 (2H, s), 6.88 (2H, d, J=9.2 Hz), 7.22 (2H, d, J=9.2 Hz), 7.39–7.51 (5H, m), 7.62 (1H, dd, J=1.2, 8.6 Hz), 7.75 (1H, dd, J=1.5, 8.9 Hz), 7.89 (1H, s), 8.00 (1H, d, J=8:5 Hz), 8.09 (1H, d, J=8.6 Hz), 8.45 (1H, s), 8.72 (1H, bs), 9.16–9.29 (3H, m), 9.47 (2H, bs).

The following compound of Example 56 was obtained in the same manner as described in Example 23.

EXAMPLE 56

N-[4-[(1-Acetoimidoyl-4-piperidyl)oxy]phenyl]-N-[(7-amidino-2-naphthyl)methyl]propanesulfonamide dihydrochloride Starting compound: N-[4-[(1-t-butoxycarbonyl-4-piperidyl)oxy]phenyl]-N-[(7-cyano-2-naphthyl)methyl]propanesulfonamide.

Mass spectrometry data (m/z): 522 (M-2HCl+1)$^+$.

Nuclear magnetic resonance spectrum (DMSO-d$_6$, TMS internal standard) δ: 1.03 (3H, t, J=7.6 Hz), 1.60–1.73 (2H, m), 1.74–1.85 (2H, m), 1.93–2.03 (2H, m), 2.27 (3H, s), 3.21–3.25 (2H, m), 3.42–3.56 (2H, m), 3.63–3.71 (1H, m), 3.75–3.82 (1H, m), 4.59–4.63 (1H, m), 5.05 (2H, s), 6.92 (2H, d, J=8.5 Hz), 7.33 (2H, d, J=8.5 Hz), 7.66 (1H, dd, J=8.6, 1.2 Hz), 7.82 (1H, dd, J=8.5, 1.8 Hz), 7.89 (1H, s), 8.01 (1H, d, J=8.6 Hz), 8.09 (1H, d, J=8.5 Hz), 8.48 (1H, s), 8.80 (1H, s), 9.28–9.38 (3H, m), 9.52 (2H, s).

The following compound of Example 57 was obtained in the same manner as described in Example 32.

EXAMPLE 57

N-[(7-Amidino-2-naphthyl)methyl]-N-[4-[(4-piperidyl)oxy]phenyl]butanesulfonamide dihydrochloride Starting compound: N-[4-[(1-t-butoxycarbonyl-4-piperidyl)oxy]phenyl]-N-[(-7-cyano-2-naphthyl)methyl]butanesulfonamide.

Mass spectrometry data (m/z): 495 (M-2HCl+1)$^+$.

Nuclear magnetic resonance spectrum (DMSO-d$_6$, TMS internal standard) δ: 0.92 (3H, t, J=7.3 Hz), 1.41–1.46 (2H, m), 1.70–1.82 (2H, m), 2.03–2.06 (4H, m), 2.92–3.04 (2H, m), 3.10–3.20 (2H, m), 3.24 (2H, t, J=7.9 Hz), 4.52–4.60 (1H, m), 5.06 (2H, s), 6.91 (2H, d, J=9.2 Hz), 7.33 (2H, d, J=9.2 Hz), 7.65 (1H, d, J=8.6 Hz), 7.80 (1H, d, J=8.6 Hz), 7.89 (1H, s), 8.01 (1H, d, J=8.6 Hz), 8.09 (1H, d, J=8.6 Hz), 8.46 (1H, s), 9.02 (1H, brs), 9.10 (1H, brs), 9.27 (2H, s), 9.49 (2H, s).

The following compound of Example 58 was obtained in the same manner as described in Example 12.

EXAMPLE 58

N-[4-[(1-Acetoimidoyl-4-piperidyl)oxy]phenyl]-N-[(7-amidino-2-naphthyl)methyl]butanesulfonamide dihydrochloride Starting compound: N-[(7-amidino-2-naphthyl]methyl]-N-[4-[(4-piperidyl)oxy]phenyl]butanesulfonamide dihydrochloride.

Mass spectrometry data (m/z): 536 (M-2HCl+1)$^+$.

Nuclear magnetic resonance spectrum (DMSO-d$_6$, TMS internal standard) δ: 0.92 (3H, t, J=7.3 Hz), 1.41–1.46 (2H, m), 1.62–1.78 (4H, m), 1.91–2.01 (2H, m), 2.27 (3H, s), 3.24 (2H, t, J=7.9 Hz), 4.58–4.62 (1H, m), 5.06 (2H, s), 6.91 (2H, d, J=9.2 Hz), 7.33 (2H, d, J=9.2 Hz), 7.65 (1H, d, J=8.5 Hz), 7.80 (1H, d, J=6.7 Hz), 7.90 (1H, s), 8.01 (1H, d, J=8.6 Hz), 8.09 (1H, d, J=8.5 Hz), 8.46 (1H, s), 7.12 (1H, s), 9.22 (3H, s), 9.47 (2H, s).

The following compound of Example 59 was obtained in the same manner as described in Example 32.

EXAMPLE 59

N-[(7-Amidino-2-naphthyl)methyl]-N-[4-[(4-piperidyl)oxy]phenyl]trifluoromethanesulfonamide dihydrochloride Starting compound: N-[4-[(1-t-butoxycarbonyl-4-piperidyl)oxy]phenyl]-N-[(7-cyano-2-naphthyl)methyl]trifluoromethanesulfonamide.

Mass spectrometry data (m/z): 507 (M-2HCl+1)$^+$.

Nuclear magnetic resonance spectrum (DMSO-d$_6$, TMS internal standard) δ: 1.72–1.81 (2H, m), 1.97–2.08 (2H, m), 2.96–3.06 (2H, m), 3.09–3.20 (2H, m), 4.56–4.62 (1H, m), 5.25 (2H, s), 6.95 (2H, d, J=9.2 Hz), 7.29 (2H, d, J=9.2 Hz), 7.61 (1H, d, J=8.5 Hz), 7.85 (1H, d, J=8.5 Hz), 7.91 (1H, s), 8.03 (1H, d, J=7.9 Hz), 8.11 (1H, d, J=9.2 Hz), 8.51 (1H, s), 9.13 (1H, brs), 9.21 (1H, brs), 9.35 (2H, s), 9.54 (2H, s).

The following compound of Example 60 was obtained in the same manner as described in Example 12.

EXAMPLE 60

N-[4-[(1-Acetoimidoyl-4-piperidyl)oxy]phenyl]-N-[(7-amidino-2-naphthyl)methyl]trifluoromethanesulfonamide dihydrochloride Starting compound: N-[(7-amidino-2-naphthyl)methyl]-N-[4-[(4-piperidyl)oxy]phenyl]trifluoromethanesulfonamide dihydrochloride.

Mass spectrometry-data (m/z): 548 (M-2HCl+1)$^+$.

Nuclear magnetic resonance spectrum (DMSO-d$_6$, TMS internal standard) δ: 1.60–1.74 (2H, m), 1.92–2.05 (2H, m), 2.26 (3H, s), 3.44–3.50 (2H, m), 3.67–3.76 (2H, m), 4.63–4.65 (1H, m), 5.25 (2H, s), 6.95 (2H, d, J=9.2 Hz), 7.30 (2H, d, J=9.2 Hz), 7.60 (1H, d, J=6.7 Hz), 7.83 (1H, d, J=7.3 Hz), 7.92 (1H, s), 8.04 (1H, d, J=8.6 Hz), 8.12 (1H, d, J=8.6 Hz), 8.48 (1H, s), 8.68 (1H, s), 9.20 (3H, s), 9.47 (2H, s).

The following compound of Example 61 was obtained in the same manner as described in Example 32.

EXAMPLE 61

N-[(7-Amidino-2-naphthyl)methyl]-N-[4-[(4-piperidyl)oxy]phenyl]isopropanesulfonamide dihydrochloride Starting compound: N-[4-[(1-t-butoxycarbonyl-4-piperidyl)oxy]phenyl]-N-[(7-cyano-2-naphthyl)methyl]isopropanesulfonamide.

Mass spectrometry data (m/z): 481 (M-2HCl+1)$^+$.

Nuclear magnetic resonance spectrum (DMSO-d$_6$, TMS internal standard) δ: 1.35 (6H, d, J=6.4 Hz), 1.69–1.80 (2H, m), 1.96–2.06 (2H, m), 2.94–3.06 (2H, m), 3.11–3.27 (3H, m), 4.50–4.57 (1H, m), 5.11 (2H, s), 6.89 (2H, d, J=8.8 Hz), 7.33 (2H, d, J=8.8 Hz), 7.64 (1H, d, J=8.3 Hz), 7.79 (1H, d, J=8.8 Hz), 7.88 (1H, s), 8.01 (1H, d, J=8.8 Hz), 8.09 (1H, d, J=8.8 Hz), 8.44 (1H, s), 8.81 (1H, brs), 8.86 (1H, brs), 9.15 (2H, s), 9.45 (2H, s).

The following compound of Example 62 was obtained in the same manner as described in Example 12.

EXAMPLE 62

N-[4-[(1-Acetoimidoyl-4-piperidyl)oxy]phenyl]-N-[(7-amidino-2-naphthyl)methyl]isopropanesulfonamide dihydrochloride Starting compound: N-[(7-amidino-2-naphthyl)methyl]-N-[4-[(4-piperidyl)oxy]phenyl]isopropanesulfonamide dihydrochloride.

Mass spectrometry data (m/z): 522 (M-2HCl+1)$^+$.

Nuclear magnetic resonance spectrum (DMSO-d$_6$, TMS internal standard) δ: 1.35 (d, 6H, J=6.8 Hz), 1.60–1.73 (2H, m), 1.92–2.01 (2H, m), 2.26 (3H, s), 3.03–3.10 (1H, m), 3.40–3.49 (2H, m), 3.67–3.76 (2H, m), 4.60–4.67 (1H, m), 5.11 (2H, s), 6.90 (2H, d, J=9.3 Hz), 7.32 (2H, d, J=9.3 Hz), 7.64 (1H, d, J=8.8 Hz), 7.80 (1H, d, J=6.8 Hz), 7.88 (1H, s), 8.01 (1H, d, J=8.3 Hz), 8.09 (1H, d, J=8.8 Hz), 8.46 (1H, s), 8.72 (1H, s), 9.23 (3H, s), 9.58 (2H, s).

The following compound of Example 63 was obtained in the same manner as described in Example 23.

EXAMPLE 63

Ethyl N-[N-[4-[(1-acetoimidoyl-4-piperidyl)oxy]phenyl]-N-[7-amidino-2-naphthyl)methyl]sulfamoyl]carbamate dihydrochloride Starting compound: ethyl N-[N-[4-[(1-t-butoxycarbonyl-4-piperidyl)oxy]phenyl]-N-[(7-cyano-2-naphthyl)methyl]sulfamoyl]carbamate.

Mass spectrometry data (m/z): 567 (M-2HCl+1)$^+$.

Nuclear magnetic resonance spectrum (DMSO-d$_6$, TMS internal standard) δ: 1.27 (3H, t, J=7.3 Hz), 1.60–1.75 (2H, m), 1.95–2.03 (2H, m), 2.27 (3H, s), 3.41–3.57 (2H, m), 3.63–3.73 (1H, m), 3.73–3.82 (1H, m), 4.23 (2H, q, J=7.3 Hz), 4.60–4.67 (1H, m), 5.17 (2H, s), 6.96 (2H, d, J=9.2 Hz), 7.23 (2H, d, J=8.5 Hz), 7.65 (1H, d, J=7.3 Hz), 7.82 (1H, d, J=8.5 Hz), 7.91 (1H, s), 8.03 (1H, d, J=8.5 Hz), 8.10 (1H, d, J=8.5 Hz), 8.47 (1H, s), 8.81 (1H, bs), 9.23–9.40 (3H, m), 9.51 (2H, s), 11.52 (1H, s).

The following compound of Example 64 was obtained in the same manner as described in Example 32.

EXAMPLE 64

N-[(7-Amidino-2-naphthyl)methyl]-N-[4-[(4-piperidyl)oxy]phenyl]-4-nitrobenzenesulfonamide dihydrochloride Starting compound: N-[4-[(1-t-butoxycarbonyl-4-piperidyl)oxy]phenyl]-N-[(7-cyano-2-naphthyl)methyl]-4-nitrobenzenesulfonamide.

Mass spectrometry data (m/z): 560 (M-2HCl+1)$^+$.

Nuclear magnetic resonance spectrum (DMSO-d$_6$, TMS internal standard) δ: 1.71–1.82 (2H, m), 2.00–2.08 (2H, m), 2.91–3.03 (2H, m), 3.08–3.19 (2H, m), 4.51–4.60 (1H, m), 5.03 (2H, s), 6.86 (2H, d, J=8.6 Hz), 7.02 (2H, d, J=9.2 Hz), 7.66 (1H, d, J=8.6 Hz), 7.83 (1H, d, J=6.7 Hz), 7.90 (1H, s), 7.98 (2H, d, J=8.6 Hz), 8.02 (1H, d, J=8.5 Hz), 8.09 (1H, d, J=8.5 Hz), 8.45 (2H, d, J=9.2 Hz), 8.48 (1H, s), 9.22 (1H, brs), 9.29 (1H, brs), 9.38 (2H, s), 9.56 (2H, s).

The following compound of Example 65 was obtained in the same manner as described in Example 12.

EXAMPLE 65

N-[4-[(1-Acetoimidoyl-4-piperidyl)oxy]phenyl]-N-[(7-amidino-2-naphthyl)methyl]-4-nitrobenzenesulfonamide dihydrochloride Starting compound: N-[(7-amidino-2-naphthyl)methyl]-N-[4-[(4-piperidyl)oxy]phenyl]-4-nitrobenzenesulfonamide dihydrochloride.

Mass spectrometry data (m/z): 601 (M-2HCl+1)$^+$.

Nuclear magnetic resonance spectrum (DMSO-d$_6$, TMS internal standard) δ: 1.63–1.68 (2H, m), 1.84–2.02 (2H, m), 2.27 (3H, s), 3.47–3.51 (2H, m), 3.66–3.79 (2H, m), 4.58–4.62 (1H, m), 5.03 (2H, s), 6.86 (2H, d, J=8.5 Hz), 7.02 (2H, d, J=9.2 Hz), 7.66 (1H, d, J=8.5 Hz), 7.83 (1H, d, J=8.6 Hz), 7.91 (1H, s), 7.98 (1H, d, J=9.2 Hz), 8.02 (1H, d, J=8.5 Hz), 8.09 (1H, d, J=8.6 Hz), 8.45–8.48 (3H, m), 8.82 (1H, s), 9.34 (3H, s), 9.54 (2H, s).

The following compound of Example 66 was obtained in the same manner as described in Example 23.

EXAMPLE 66

Ethyl 4-[N-[4-[(1-acetoimidoyl-4-piperidyl)oxy] phenyl]-N-[(7-amidino-2-naphthyl)methyl] sulfamoyl)benzoate dihydrochloride Starting compound: 4-N-[4-[(1-t-butoxycarbonyl-4-piperidyl)oxy]phenyl]-N-[(7-cyano-2-naphthyl)methyl] sulfamoyl]benzoic acid.

Mass spectrometry data (m/z): 628 (M-2HCl+1)$^+$.

Nuclear magnetic resonance spectrum (DMSO-d$_6$, TMS internal standard) δ: 1.37 (3H, t, J=7.0 Hz), 1.57–1.73 (2H, m), 1.92–2.02 (2H, m), 2.26 (3H, s), 3.40–3.50 (2H, m), 3.62–3.80 (2H, m), 4.39 (2H, q, J=7.0 Hz), 4.55–4.62 (1H, m), 5.00 (2H, s), 6.85 (2H, d, J=9.2 Hz), 6.99 (2H, d, J=8.6 Hz), 7.66 (1H, d, J=8.6 Hz), 7.81 (1H, dd, J=1.8, 9.2 Hz), 7.85 (2H, d, J=8.5 Hz), 7.92 (1H, s), 8.02 (1H, d, J=8.6 Hz), 8.09 (1H, d, J=8.5 Hz), 8.18 (2H, d, J=8.6 Hz), 8.44 (1H, s), 8.71 (1H, s), 9.13–9.27 (3H, m), 9.47 (2H, s).

The following compound of Example 67 was obtained in the same manner as described in Example 23.

EXAMPLE 67

Ethyl 3-[N-[4-[(1-acetoimidoyl-4-piperidyl)oxy]-phenyl]-N-[(7-amidino-2-naphthyl)methyl] sulfamoyl]benzoate dihydrochloride Starting compound: 3-[N-[4-[(1-t-butoxycarbonyl-4-piperidyl)oxy]phenyl]-N-[(7-cyano-2-naphthyl)methyl] sulfamoyl]benzoic acid.

Mass spectrometry data (m/z): 628 (M-2HCl+1)$^+$.

Nuclear magnetic resonance spectrum (DMSO-d$_6$, TMS internal standard) δ: 1.33 (3H, t, J=7.0 Hz), 1.58–1.72 (2H, m), 1.93–2.02 (2H, m), 2.26 (3H, s), 3.41–3.52 (2H, m), 3.63–3.80 (2H, m), 4.36 (2H, q, J=7.0 Hz), 4.56–4.63 (1H, m), 4.99 (2H, s), 6.86 (2H, d, J=9.2 Hz), 7.02 (2H, d, J=8.5 Hz), 7.67 (1H, d, J=8.6 Hz), 7.78–7.86 (2H, m), 7.93 (1H, s), 7.99–8.03 (2H, m), 8.05–8.12 (2H, m), 8.30 (1H, d, J=7.9 Hz), 8.44 (1H, s), 8.71 (1H, bs), 9.14–9.30 (3H, m), 9.47 (2H, s)

The following compound of Example 68 was obtained in the same manner as described in Example 23.

EXAMPLE 68

Methyl 2-[N-[4-[(1-acetoimidoyl-4-piperidyl)oxy]-phenyl]-N-[(7-amidino-2-naphthyl)methyl] sulfamoyl]benzoate dihydrochloride Starting compound: methyl 2-[N-[4-[(1-t-butoxycarbonyl-4-piperidyl)oxy]phenyl]-N-[(7-cyano-2-naphthyl)methyl]sulfamoyl]benzoate.

Mass spectrometry data (m/z): 614 (M-2HCl+1)$^+$.

Nuclear magnetic resonance spectrum (DMSO-d$_6$, TMS internal standard) δ: 1.57–1.73 (2H, m), 1.91–2.02 (2H, m), 2.26 (3H, s), 3.41–3.51 (2H, m), 3.63–3.80 (5H, m), 4.55–4.62 (1H, m), 5.08 (2H, s), 6.87 (2H, d, J=9.2 Hz), 7.08 (2H, d, J=9.2 Hz), 7.60–7.71 (4H, m), 7.75–7.84 (2H, m), 7.93 (1H, s), 8.02 (1H, d, J=8:5 Hz), 8.10 (1H, d, J=8.5 Hz), 8.45 (1H, s), 8.72 (1H, bs), 9.12–9.20 (3H, m), 9.48 (2H, bs).

The following compound of Example 69 was obtained in the same manner as described in Example 23.

EXAMPLE 69

N-[4-[(1-Acetoimidoyl-4-piperidyl)oxy]phenyl]-N-[ (7-amidino-2-naphthyl)methyl]sulfonamide dihydrochloride Starting compound: t-butyl N-[N-[4-[(1-t-butoxycarbonyl-4-piperidyl)oxy]phenyl]-N-[(7-cyano-2-naphthyl)methyl]sulfamoyl]carbamate.

Mass spectrometry data (m/z): 495 (M-2HCl+1)$^+$.

Nuclear magnetic resonance spectrum (DMSO-d$_6$, TMS internal standard) δ: 1.59–1.74 (2H, m), 1.93–2.03 (2H, m), 2.27 (3H, s), 3.43–3.57 (2H, m), 3.63–3.71 (1H, m), 3.73–3.81 (1H, m), 4.56–4.63 (1H, m), 4.90 (2H, s), 6.89 (2H, d, J=9.2 Hz), 7.20 (2H, s), 7.27 (2H, d, J=9.2 Hz), 7.71 (1H, d, J=7.6 Hz), 7.80 (1H, dd, J=1.8, 8.6 Hz), 7.92 (1H, s), 7.99 (1H, d, J=8.5 Hz), 8.08 (1H, d, J=8.6 Hz), 8.44 (1H, s), 8.80 (1H, bs), 9.24–9.37 (3H, m), 9.51 (2H, s).

The following compound of Example 70 was obtained in the same manner as described in Example 32.

EXAMPLE 70

Ethyl [N-[(7-amidino-2-naphthyl)methyl]-N-[4-[(4-piperidyl)oxy]phenyl]sulfamoyl]acetate dihydrochloride Starting compound: ethyl [N-[4-[(1-t-butoxycarbonyl-4-piperidyl)oxy]phenyl]-N-[(7-cyano-2-naphthyl)methyl] sulfamoyl]acetate.

Mass spectrometry data (m/z): 525 (M-2HCl+1)$^+$.

Nuclear magnetic resonance spectrum (DMSO-d$_6$, TMS internal standard) δ: 1.26 (3H, t, J=7.3 Hz), 1.74–1.82 (2H, m), 1.97–2.09 (2H, m), 2.97–3.04 (2H, m), 3.10–3.21 (2H, m), 3.23 (2H, q, J=6.7 Hz), 4.43 (2H, s), 4.51–4.62 (1H, m), 5.05 (2H, s), 6.94 (2H, d, J=9.2 Hz), 7.32 (2H, d, J=9.2 Hz), 7.64 (1H, d, J=9.8 Hz), 7.80 (1H, d, J=8.6 Hz), 7.90 (1H, s), 8.01 (1H, d, J=9.2 Hz), 8.09 (1H, d, J=8.5 Hz), 8.46 (1H, s), 8.98 (1H, brs), 9.05 (1H, brs), 9.25 (2H, s), 9.48 (2H, s).

The following compound of Example 71 was obtained in the same manner as described in Example 12.

EXAMPLE 71

Ethyl [N-[4-[(1-acetoimidoyl-4-piperidyl)oxy] phenyl]-N-[(7-amidino-2-naphthyl)methyl] sulfamoyl]acetate dihydrochloride Starting compound: ethyl [N-[(7-amidino-2-naphthyl] methyl]-N-[4-[(4-piperidyl)oxy]phenyl]sulfamoyl]acetate dihydrochloride.

Mass spectrometry data (m/z): 566 (M-2HCl+1)$^+$.

Nuclear magnetic resonance spectrum (DMSO-d$_6$, TMS internal standard) δ: 1.25 (3H, t, J=7.3 Hz), 1.61–1.74 (2H, m), 1.94–2.04 (2H, m), 2.26 (3H, s), 3.43–3.51 (2H, m), 3.64–3.78 (2H, m), 4.23 (2H, q, J=7.3 Hz), 4.43 (2H, s), 4.59–4.65 (1H, m), 5.05 (2H, s), 6.94 (2H, d, J=9.2 Hz), 7.32 (2H, d, J=9.2 Hz), 7.64 (1H, d, J=8.5 Hz), 7.79 (1H, d, J=8.6 Hz), 7.92 (1H, s), 8.01 (1H, d, J=8.0 Hz), 8.10 (1H, d, J=8.5 Hz), 8.45 (1H, s), 8.64 (1H, s), 9.12 (3H, s), 9.43 (2H, s).

The following compound of Example 72 was obtained in the same manner as described in Example 32.

EXAMPLE 72

Ethyl 3-[N-[(7-amidino-2-naphthyl)methyl]-N-[4-[(4-piperidyl)oxy]phenyl]sulfamoyl]propionate dihydrochloride Starting compound: ethyl 3-[N-[4-[(1-t-butoxycarbonyl-4-piperidyl)oxy]phenyl]-N-[(7-cyano-2-naphthyl)methyl]sulfamoyl]propionate dihydrochloride.

Mass spectrometry data (m/z): 539 (M-2HCl+1)$^+$.

Nuclear magnetic resonance spectrum (DMSO-d$_6$, TMS internal standard) δ: 1.20 (3H, t, J=7.3 Hz), 1.72–1.84 (2H, m), 1.99–2.13 (2H, m), 2.82 (2H, t, J=7.3 Hz), 2.97–3.10 (2H, m), 3.12–3.22 (2H, m), 3.53 (2H, t, J=7.3 Hz), 4.11 (2H, q, J=6.7 Hz), 4.56–4.62 (1H, m), 5.07 (2H, s), 6.92 (2H, d, J=8.5 Hz), 7.35 (2H, d, J=8.6 Hz), 7.64 (1H, d, J=8.5 Hz), 7.82 (1H, d, J=8.5 Hz), 7.89 (1H, s), 8.01 (1H, d, J=8.6 Hz), 8.09 (1H, d, J=8.5 Hz), 8.43 (1H, s), 9.12 (1H, brs), 9.21 (1H, brs), 9.33 (2H, s), 9.52 (2H, s).

The following compound of Example 73 was obtained in the same manner as described in Example 12.

EXAMPLE 73

Ethyl 3-[N-[4-[(1-acetoimidoyl-4-piperidyl)oxy]phenyl]-N-[(7-amidino-2-naphthyl)methyl]sulfamoyl]propionate dihydrochloride Starting compound: ethyl 3-[N-[(7-amidino-2-naphthyl)methyl]-N-[4-[(4-piperidyl)oxy]phenyl]sulfamoyl]propionate dihydrochloride.

Mass spectrometry data (m/z): 580 (M-2HCl+1)$^+$.

Nuclear magnetic resonance spectrum (DMSO-d$_6$, TMS internal standard) δ: 1.20 (3H, t, J=7.3 Hz), 1.58–1.73 (2H, m), 1.94–2.08 (2H, m), 2.29 (3H, s), 2.82 (2H, t, J=7.3 Hz), 3.47–3.49 (2H, m), 3.53 (2H, t, J=7.3 Hz), 3.68–3.75 (2H, m), 4.11 (2H, q, J=7.3 Hz), 4.58–4.64 (1H, m), 5.07 (2H, s), 6.92 (2H, d, J=8.6 Hz), 7.35 (2H, d, J=8.6 Hz), 7.64 (1H, d, J=8.5 Hz), 7.79 (1H, d, J=8.6 Hz), 7.90 (1H, s), 8.01 (1H, d, J=8.6 Hz), 8.09 (1H, d, J=9.1 Hz), 8.45 (1H, s), 8.66 (1H, s), 9.16 (3H, s), 9.45 (2H, s).

The following compound of Example 74 was obtained in the same manner as described in Example 30.

EXAMPLE 74

4-[N-[4-[(1-Acetoimidoyl-4-piperidyl)oxy]phenyl]-N-[(7-amidino-2-naphthyl)methyl]sulfamoyl]benzoic acid dihydrochloride Starting compound: ethyl 4-[N-[4-[(1-acetoimidoyl-4-piperidyl)oxy]phenyl]-N-[(7-amidino-2-naphthyl)methyl]sulfamoyl]benzoate dihydrochloride.

Mass spectrometry data (m/z): 600 (M-2HCl+1)$^+$.

Nuclear magnetic resonance spectrum (DMSO-d$_6$, TMS internal standard) δ: 1.57–1.72 (2H, m), 1.91–2.02 (2H, m), 2.26 (3H, s), 3.40–3.51 (2H, m), 3.62–3.80 (2H, m), 4.55–4.62 (1H, m), 5.01 (2H, s), 6.85 (2H, d, J=9.2 Hz), 7.00 (2H, d, J=9.2 Hz), 7.67 (1H, d, J=9.5 Hz), 7.77–7.85 (3H, m), 7.92 (1H, s), 8.02 (1H, d, J=8.6 Hz), 8.09 (1H, d, J=8.5 Hz), 8.16 (2H, d, J=8.6 Hz), 8.45 (1H, s), 8.74 (1H, s), 9.18–9.34 (3H, m), 9.49 (2H, s), 13.53 (1H, bs).

The following compound of Example 75 was obtained in the same manner as described in Example 30.

EXAMPLE 75

[N-[4-[(1-Acetoimidoyl-4-piperidyl)oxy]phenyl]-N-[(7-amidino-2-naphthyl)methyl]sulfamoyl]acetic acid dihydrochloride Starting compound: ethyl]-N-[4-[(1-acetoimidoyl-4-piperidyl)oxy]phenyl]-N-[(7-amidino-2-naphthyl)methyl]sulfamoyl]acetate dihydrochloride.

Mass spectrometry data (m/z): 538 (M-2HCl+1)$^+$.

Nuclear magnetic resonance spectrum (DMSO-d$_6$, TMS internal standard) δ: 1.61–1.75 (2H, m), 1.92–2.04 (2H, m), 2.27 (3H, s), 3.47–3.52 (2H, m), 3.68–3.78 (2H, m), 4.30 (2H, s), 4.58–4.64 (1H, m), 5.05 (2H, s), 6.94 (2H, d, J=9.2 Hz), 7.32 (2H, d, J=8.5 Hz), 7.65 (1H, d, J=8.6 Hz), 7.82 (1H, d, J=8.5 Hz), 7.90 (1H, s), 8.01 (1H, d, J=8.6 Hz), 8.09 (1H, d, J=9.2 Hz), 8.48 (1H, s), 8.80 (1H, s), 9.33 (3H, s), 9.52 (2H, s).

EXAMPLE 76

N-[4-[(1-t-Butoxycarbonyl-4-piperidyl)oxy]phenyl]-N-[(7-cyano-2-naphthyl)methyl]-4-nitrobenzenesulfonamide obtained in Reference Example 38 (450 mg) was dissolved in 10 ml of ethyl acetate, 1.6 g of stannic chloride dihydrate was added to the solution, and the mixture was heated under reflux for 5 hours. The reaction solution was cooled and then saturated sodium bicarbonate aqueous solution was added, and the thus formed precipitate was filtered using celite. The organic layer was washed with water and brine in that order, dried over anhydrous sodium sulfate, and then evaporated. The resulting crude N-[(7-cyano-2-naphthyl)methyl]-N-[4-[(4-piperidyl)oxy]phenyl]-4-aminobenzenesulfonamide was dissolved in a mixed solution of 5 ml of ethanol and 5 ml of chloroform. This solution was cooled to −70° C. while stirring and hydrogen chloride was introduced until saturations Then, the solution was stirred at room temperature for 2 days and then evaporated. The resulting residue was dissolved in 5 ml of ethanol, 1.0 g of ammonium acetate was added to the solution, and the mixture was stirred at room temperature for 4 days. The reaction solution was evaporated, and the resulting residue was purified by an ODS (YMC-GEL ODS-A 120-230/70) column chromatography using methanol:water (100:0) as the eluent, followed by addition of a small amount of 1N hydrochloric acid and freeze-drying to give 109 mg of N-[(7-amidino-2-naphthyl)methyl]-N-[4-[(4-piperidyl)oxy]phenyl]-4-aminobenzenesulfonamide trihydrochloride.

Mass spectrometry data (m/z): 530 (M-3HCl+1)$^+$.

Nuclear magnetic resonance spectrum (DMSO-d$_6$, TMS internal standard) δ: 1.71–1.80 (2H, m), 1.98–2.06 (2H, m), 2.91–3.02 (2H, m), 3.10–3.21 (2H, m), 4.51–4.57 (1H, m), 4.88 (2H, s), 6.69 (2H, d, J=9.15 Hz), 6.83 (2H, d, J=9.2 Hz), 6.99 (2H, d, J=9.2 Hz), 7.32 (2H, d, J=8.5 Hz), 7.66 (1H, d, J=8.5 Hz), 7.79 (1H, d, J=8.6 Hz), 7.90 (1H, s), 7.92 (1H, d, J=8.5 Hz), 8.07 (1H, d, J=8.6 Hz), 8.43 (1H, s), 9.10 (1H, brs), 9.19 (1H, brs), 9.32 (2H, s), 9.51 (2H, s).

The following compound of Example 77 was obtained in the same manner as described in Example 12.

EXAMPLE 77

N-[4-[(1-Acetoimidoyl-4-piperidyl)oxy]phenyl]-N-[(7-amidino-2-naphthyl)methyl]-4-aminobenzenesulfonamide trihydrochloride Starting compound: N-[(7-amidino-2-naphthyl]methyl]-N-[4-[(4-piperidyl)oxy]phenyl]-4-aminobenzenesulfonamide trihydrochloride.

Mass spectrometry data (m/z): 571 (M-3HCl+1)$^+$.

Nuclear magnetic resonance spectrum (DMSO-d$_6$, TMS internal standard) δ: 1.57–1.72 (2H, m), 1.91–2.02 (2H, m), 2.28 (3H, s), 3.40–3.53 (2H, m), 3.66–3.76 (2H, m), 4.20–4.25 (2H, br), 4.52–4.61 (1H, m), 4.87 (2H, s), 6.65 (2H, d, J=8.8 Hz), 6.83 (2H, d, J=8.8 Hz), 6.99 (2H, d, J=8.8 Hz), 7.30 (2H, d, J=8.8 Hz), 7.66 (1H, d, J=8.8 Hz), 7.79

(1H, d, J=10.3 Hz), 7.91 (1H, s), 7.98 (1H, d, J=8.8 Hz), 8.07 (1H, d, J=8.3 Hz), 8.43 (1H, s), 8.76 (1H, s), 9.27 (3H, s), 9.49 (2H, s).

The following compound of Example 78 was obtained in the same manner as described in Example 32.

The following compound of Example 80 was obtained in the same manner of Example 32.

EXAMPLE 80

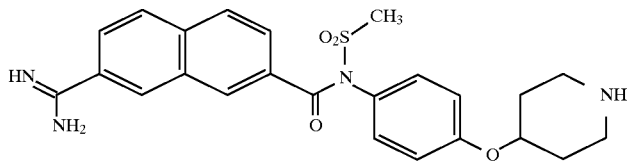

7-Amidino-N-methylsulfonyl-N-[4-[(4-piperidyl)oxy]phenyl]-2-naphthalenecarboxamide dihydrochloride Starting compound: N-[4-[(1-t-butoxycarbonyl-4-piperidyl)oxy]phenyl]-7-cyano-N-methylsulfonyl-2-naphthalenecarboxamide.

Mass spectrometry data (m/z): 467 (M-2HCl+1)$^+$.

Nuclear magnetic resonance spectrum (DMSO-d$_6$, TMS internal standard) δ: 1.65–1.77 (2H, m), 1.84–2.06 (2H, m), 2.92–3.04 (2H, m), 3.09–3.20 (2H, m), 3.59 (3H, s), 4.51–4.61 (1H, m), 6.90 (2H, d, J=8.8 Hz), 7.42 (2H, d, J=8.8 Hz), 7.72 (1H, dd, J=8.8, 1.5 Hz), 7.87 (1H, d, J=9.5 Hz), 7.94 (1H, d, J=8.8 Hz), 8.11 (1H, d, J=8.8 Hz), 8.34 (1H, s), 8.49 (1H, s), 8.71–8.92 (2H, m), 9.20 (2H, s), 9.51 (2H, s).

The following compound of Example 81 was obtained in the same manner as described in Example 12.

EXAMPLE 78

N-[(7-Amidino-2-naphthyl)methyl]-N'-methyl-N-[4-[(4-piperidyl)oxy]phenyl]sulfamide dihydrochloride Starting compound: t-butyl N-[N-[4-[(1-t-butoxycarbonyl-4-piperidyl)oxy]phenyl]-N-[(7-cyano-2-naphthyl)methyl]sulfamoyl]-N-methylcarbamate.

Mass spectrometry data (m/z): 468 (M-2HCl+1)$^+$.

Nuclear magnetic resonance spectrum (DMSO-d$_6$, TMS internal standard) δ: 1.70–1.82 (2H, m), 1.96–2.08 (2H, m), 2.67 (3H, d, J=4.9 Hz), 2.93 3.06 (2H, m), 3.11–3.21 (2H, m), 4.49–4.59 (1H, m), 4.96 (2H, s), 6.89 (2H, d, J=8.8 Hz), 7.27 (2H, d, J=9.3 Hz), 7.38–7.46 (1H, m), 7.65 (1H, d, J=8.3 Hz), 7.80 (1H, d, J=8.8 Hz), 7.89 (1H, s), 7.99 (1H, d, J=8.3 Hz), 8.08 (1H, d, J=8.8 Hz), 8.43 (1H, s), 8.90–9.13 (2H, m), 9.23 (2H, s), 9.48 (2H, s).

The following compound of Example 79 was obtained in the same manner of Example 12.

EXAMPLE 81

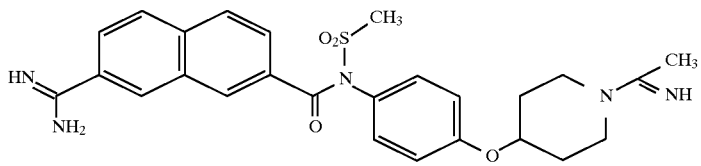

N-[4-[(1-Acetoimidoyl-4-piperidyl)oxy]phenyl]-7-amidino-N-methylsulfonyl-2-naphthalenecarboxamide dihydrochloride Starting compound: 7-amidino-N-methylsulfonyl-N-[4-[(4-piperidyl)oxy]phenyl]-2-naphthalenecarboxamide dihydrochloride.

Mass spectrometry-data (m/z): 508 (M-2HCl+1)$^+$.

Nuclear magnetic resonance spectrum (DMSO-d$_6$, TMS internal standard) δ: 1.55–1.70 (2H, m), 1.89–2.00 (2H, m), 2.26 (3H, s), 3.40–3.50 (2H, m), 3.60 (3H, s), 3.62–3.69 (1H, m), 3.69–3.78 (1H, m), 4.57–4.67 (1H, m), 6.91 (2H, d, J=9.2 Hz), 7.42 (2H, d, J=9.2 Hz), 7.72 (1H, dd, J=1.5, 8.9 Hz), 7.89 (1H, dd, J=1.8, 8.5 Hz), 7.94 (1H, d, J=8.6 Hz), 8.11 (1H, d, J=8.6 Hz), 8.34 (1H, s), 8.51 (1H, s), 8.65–8.74 (1H, m), 9.17–9.31 (3H, m), 9.54 (2H, s).

The following compound of Example 82 was obtained in the same manner as described in Example 32.

EXAMPLE 79

N-[4-[(1-Acetoimidoyl-4-piperidyl)oxy]phenyl]-N-[(7-amidino-2-naphthyl)methyl]-N'-methylsulfamide dihydrochloride Starting compound: N-[(7-amidino-2-naphthyl)methyl]-N'-methyl-N-[4-[(4-piperidyl)oxy]phenyl]sulfamide dihydrochloride.

Mass spectrometry data (m/z): 509 (M-2HCl+1)$^+$.

Nuclear magnetic resonance spectrum (DMSO-d$_6$, TMS internal standard) δ: 1.59–1.73 (2H, m), 1.92–2.03 (2H, m), 2.27 (3H, s), 2.67 (3H, d, J=4.9 Hz), 3.41–3.55 (2H, m), 3.63–3.72 (1H, m), 3.72–3.81 (1H, m), 4.56–4.63 (1H, m), 4.96 (2H, s), 6.89 (2H, d, J=9.2 Hz), 7.27 (2H, d, J=8.5 Hz), 7.39–7.46 (1H, m), 7.66 (1H, d, J=8.6 Hz), 7.81 (1H, dd, J=1.5, 8.8 Hz), 7.89 (1H, s), 8.00 (1H, d, J=8.5 Hz), 8.09 (1H, d, J=8.6 Hz), 8.45 (1H, s), 8.79 (1H, s), 9.23–9.40 (3H, m), 9.52 (2H, s).

EXAMPLE 82

Ethyl N-[N-[(7-amidino-2-naphthyl)methyl]-N-[(4-piperidyl)oxy]phenyl]sulfamoyl]-N-methylcarbamate dihydrochloride Starting compound: ethyl N-[N-[4-[(1-t-butoxycarbonyl-4-piperidyl)oxy]phenyl]-N-[(7-cyano-2-naphthyl)methyl]sulfamoyl]-N-methylcarbamate.

Mass spectrometry data (m/z): 540 (M-2HCl+1)$^+$.

Nuclear magnetic resonance spectrum (DMSO-d$_6$, TMS internal standard) δ: 1.35 (3H, t, J=7.0 Hz), 1.70–1.82 (2H, m), 1.96–2.10 (2H, m), 2.92 (3H, s), 2.94–3.08 (2H, m), 3.10–3.21 (2H, m), 4.36 (2H, q, J=7.0 Hz), 4.55–4.63 (1H, m), 5.18 (2H, s), 6.98 (2H, d, J=9.2 Hz), 7.22 (2H, d, J=9.2 Hz), 7.64 (1H, d, J=8.5 Hz), 7.82 (1H, d, J=8.5 Hz), 7.93 (1H, s), 8.04 (1H, d, J=8.6 Hz), 8.11 (1H, d, J=8.6 Hz), 8.47 (1H, s), 8.90–9.32 (3H, m), 9.49 (3H, s).

EXAMPLE 83

Ethyl N-[N-[4-[(1-acetoimidoyl-4-piperidyl)oxy] phenyl]-N-[(7-amidino-2-naphthyl)methyl sulfamoyl]-N-methylcarbamate dihydrochloride Starting compound: ethyl N-[N-[(7-amidino-2-naphthyl] methyl]-N-[4-[(4-piperidyl)oxy]phenyl]sulfamoyl]-N-methylcarbamate.

Mass spectrometry data (m/z): 581 (M-2HCl+1)$^+$.

Nuclear magnetic resonance spectrum (DMSO-d$_6$, TMS internal standard) δ: 1.35 (3H, t, J=7.0 Hz), 1.51–1.75 (2H, m), 1.94–2.06 (2H, m), 2.27 (3H, s), 2.92 (3H, s), 3.41–3.53 (2H, m), 3.64–3.73 (1H, m), 3.73–3.82 (1H, m), 4.36 (2H, q, J=7.0 Hz), 4.61–4.68 (1H, m), 5.18 (2H, s), 6.98 (2H, d, J=9.2 Hz), 7.22 (2H, d, J=9.2 Hz), 7.64 (1H, dd, J=1.2, 8.5 Hz), 7.83 (1H, dd, J=1.8, 8.5 Hz), 7.93 (1H, s), 8.05 (1H, d, J=8.6 Hz), 8.11 (1H, d, J=8.6 Hz), 8.48 (1H, s), 8.76 (1H, bs), 9.22–9.35 (3H, m), 9.51 (2H, s).

The following compound of Example 84 was obtained in the same manner as described in Example 32.

EXAMPLE 84

Methyl N-[N-[(7-amidino-2-naphthyl)methyl]-N-[4-[(4-piperidyl)oxy]phenyl]sulfamoyl]-N-ethoxycarbonylglycinate dihydrochloride Starting compound: methyl N-[N-[4-[(1-t-butoxycarbonyl-4-piperidyl)oxy]phenyl]-N-[(7-cyano-2-naphthyl)methyl]sulfamoyl]-N-ethoxycarbonylglycinate.

Mass spectrometry data (m/z): 598 (M-2HCl+1)$^+$.

Nuclear magnetic resonance spectrum (DMSO-d$_6$, TMS internal standard) δ: 1.30 (3H, t, J=7.0 Hz), 1.71–1.83 (2H, m), 1.98–2.09 (2H, m), 2.93–3.04 (2H, m), 3.10–3.21 (2H, m), 3.62 (3H, s), 4.17 (2H, s), 4.35 (2H, q, J=7.0 Hz), 4.54–4.62 (1H, m), 5.19 (2H, s), 6.96 (2H, d, J=9.2 Hz), 7.23 (2H, d, J=9.2 Hz), 7.63 (1H, d, J=9.5 Hz), 7.82 (1H, d, J=8.5 Hz), 7.91 (1H, s), 8.03 (1H, d, J=8.5 Hz), 8.11 (1H, d, J=8.6 Hz), 8.46 (1H, s), 8.95–9.15 (2H, m), 9.26 (2H, s), 9.50 (2H, s).

The following compound of Example 85 was obtained in the same manner as described in Example 12.

EXAMPLE 85

Methyl N-[N-[4-[(1-acetoimidoyl-4-piperidyl)oxy] phenyl]-N-[(7-amidino-2-naphthyl)methyl] sulfamoyl]-N-ethoxycarbonylglycinate dihydrochloride Starting compound: methyl N-[N-[(7-amidino-2-naphthyl]methyl]-N-[4-[(4-piperidyl)oxy]phenyl] sulfamoyl]-N-ethoxycarbonylglycinate. dihydrochloride Mass spectrometry data (m/z): 639 (M-2HCl+1)$^+$.

Nuclear magnetic resonance spectrum (DMSO-d$_6$, TMS internal standard) δ: 1.30 (3H, t, J=7.0 Hz), 1.60–1.75 (2H, m), 1.95–2.05 (2H, m), 2.27 (3H, s), 3.41–3.53 (2H, m), 3.62 (3H, s), 3.65–3.72 (1H, m), 3.75–3.82 (1H, m), 4.17 (2H, s), 4.35 (2H, q, J=7.0 Hz), 4.60–4.67 (1H, m), 5.19 (2H, s), 6.96 (2H, d, J=9.2 Hz), 7.23 (2H, d, J=9.2 Hz), 7.63 (1H, d, J=8.6 Hz), 7.83 (1H, d, J=8.6 Hz), 7.91 (1H, s), 8.04 (1H, d, J=8.6 Hz), 8.11 (1H, d, J=8.6 Hz), 8.47 (1H, s), 8.79 (1H, s), 9.26–9.35 (3H, m), 9.52 (2H, s).

The following compound of Example 86 was obtained in the same manner as described in Example 30.

EXAMPLE 86

N-[N-[4-[(1-Acetoimidoyl-4-piperidyl)oxy]phenyl]-N-[(7-amidino-2-naphthyl)methyl]sulfamoyl]-N-ethoxycarbonylglycine dihydrochloride Starting compound: methyl N-[N-[4-[(1-acetoimidoyl-4-piperidyl)oxy]phenyl]-N-[(7-amidino-2-naphthyl)methyl] sulfamoyl]-N-ethoxycarbonylglycinate dihydrochloride.

Mass spectrometry data (m/z): 625 (M-2HCl+1)$^+$.

Nuclear magnetic resonance spectrum (DMSO-d$_6$, TMS internal standard) δ: 1.30 (3H, t, J=7.0 Hz), 1.61–1.73 (2H, m), 1.95–2.05 (2H, m), 2.27 (3H, s), 3.41–3.53 (2H, m), 3.62–3.72 (1H, m), 3.72–3.82 (1H, m), 4.01 (2H, s), 4.34 (2H, q, J=7.0 Hz), 4.59–4.68 (1H, m), 5.19 (2H, s), 6.96 (2H, d, J=9.2 Hz), 7.23 (2H, d, J=9.2 Hz), 7.64 (1H, d, J=8.5 Hz), 7.82 (1H, d, J=8.5 Hz), 7.92 (1H, s), 8.03 (1H, d, J=8.5 Hz), 8.11 (1H, d, J=8.6 Hz), 8.46 (1H, s), 8.74 (1H, s), 9.20–9.40 (3H, m), 9.48 (2H, s), 13.01 (1H, bs).

The following compound of Example 87 was obtained in the same manner as described in Example 32.

EXAMPLE 87

Ethyl N-[N-[(7-amidino-2-naphthyl)methyl]-N-[4-[(4-piperidyl)oxy]phenyl]sulfamoyl]glycinate dihydrochloride Starting compound: ethyl N-[N-[4-[(1-t-butoxycarbonyl-4-piperidyl)oxy]phenyl]-N-[(7-cyano-2-naphthyl)methyl] sulfamoyl]-N-t-butoxycarbonylglycinate.

Mass spectrometry data (m/z): 540 (M-2HCl+1)$^+$.

Nuclear magnetic resonance spectrum (DMSO-d$_6$, TMS internal standard) δ: 1.21 (3H, t, J=7.0 Hz), 1.70–1.81 (2H, m), 1.95–2.06 (2H, m), 2.93–3.05 (2H, m), 3.07–3.19 (2H, m), 3.83 (2H, d, J=6.7 Hz), 4.14 (2H, q, J=7.0 Hz), 4.49–4.57 (1H, m), 4.94 (2H, s), 6.88 (2H, d, J=8.5 Hz), 7.28 (2H, d, J=8.6 Hz), 7.65 (1H, d, J=8.5 Hz), 7.80 (1H, d, J=8.6 Hz), 7.88 (1H, s), 7.98 (1H, d, J=8.5 Hz), 8.03–8.13 (2H, m), 8.42 (1H, s), 8.90–9.12 (2H, m), 9.25 (2H, s), 9.48 (2H, s).

The following compound of Example 88 was obtained in the same manner of Example 12.

EXAMPLE 88

Ethyl N-[N-[4-[(1-acetoimidoyl-4-piperidyl)oxy] phenyl]-N-[(7-amidino-2-naphthyl)methyl] sulfamoyl]glycinate dihydrochloride Starting compound: ethyl N-[N-[(7-amidino-2-naphthyl] methyl]-N-[4-[(4-piperidyl)oxy]phenyl]sulfamoyl]glycinate dihydrochloride.

Mass spectrometry data (m/z): 581 (M-2HCl+1)$^+$.

Nuclear magnetic resonance spectrum (DMSO-d$_6$, TMS internal standard) δ: 1.21 (3H, t, J=7.3 Hz), 1.60–1.73 (2H, m), 1.92–2.02 (2H, m), 2.27 (3H, s), 3.42–3.55 (2H, m), 3.63–3.70 (1H, m), 3.70–3.80 (1H, m), 3.83 (2H, d, J=6.1

Hz), 4.14 (2H, q, J=7.3 Hz), 4.56–4.62 (1H, m), 4.94 (2H, s), 6.89 (2H, d, J=9.2 Hz), 7.28 (2H, d, J=9.2 Hz), 7.65 (1H, d, J=8.5 Hz), 7.80 (1H, d, J=8.6 Hz), 7.89 (1H, s), 7.99 (1H, d, J=8.5 Hz), 8.04–8.10 (2H, m), 8.43 (1H, s), 8.74 (1H, s), 9.20–9.31 (3H, m), 9.48 (2H, s).

The following compound of Example 89 was obtained in the same manner of Example 29.

EXAMPLE 89

N-[N-[4-[(1-Acetoimidoyl-4-piperidyl)oxy]phenyl]-N-[(7-amidino-2-naphthyl)methyl]sulfamoyl]glycine dihydrochloride Starting compound: ethyl N-[N-[4-[(1-acetoimidoyl-4-piperidyl)oxy]phenyl]-N-[(7-amidino-2-naphthyl)methyl]sulfamoyl]glycinate dihydrochloride.

Mass spectrometry data (m/z): 553 (M-2HCl+1)$^+$.

Nuclear magnetic resonance spectrum (DMSO-$d_6$, TMS internal standard) δ: 1.60–1.71 (2H, m), 1.90–2.02 (2H, m), 2.26 (3H, s), 3.40–3.55 (2H, m), 3.61–3.81 (4H, m), 4.56–4.62 (1H, m), 4.94 (2H, s), 6.88 (2H, d, J=9.2 Hz), 7.28 (2H, d, J=8.6 Hz), 7.64 (1H, d, J=8.5 Hz), 7.78 (1H, d, J=8.5 Hz), 7.81–7.93 (2H, m), 7.97 (1H, d, J=8.6 Hz), 8.07 (1H, d, J=8.6 Hz), 8.42 (1H, s), 8.71 (1H, s), 9.26 (1H, s), 9.30–9.50 (4H, m), 12.8 (bs).

EXAMPLE 90

Ethanol which has been saturated with ammonia at 10° C. (30 ml) was added to 384 mg of ethyl N-[N-[(7-amidino-2-naphthyl]methyl]-N-[4-[(4-piperidyl)oxy]phenyl] sulfamoyl]glycinate dihydrochloride, and the mixture was stirred at 5° C. for 5 days. The reaction solution was evaporated, and the resulting residue was dissolved in 5 ml of ethanol and 10 ml of methanol. Then, 1,007 mg of ethyl acetoimidate hydrochloride and 956 mg of triethylamine were added, and then the mixture was stirred at room temperature for 1 day. After evaporation of the reaction solution, the resulting residue was purified by an ODS (YMC-GEL ODS-A 120-230/70) column chromatography using methanol:water (1:99) as the eluent, followed by addition of a small amount of 1N hydrochloric acid and freeze-drying to give 260 mg of N-[N-[4-[(1-acetoimidoyl-4-piperidyl)oxy]phenyl]-N-[(7-amidino-2-naphthyl)methyl]sulfamoyl]glycinamide dihydrochloride.

Mass spectrometry data (m/z): 552 (M-2HCl+1)$^+$.

Nuclear magnetic resonance spectrum (DMSO-$d_6$, TMS internal standard) δ: 1.60–1.73 (2H, m), 1.91–2.02 (2H, m), 2.26 (3H, s), 3.42–3.51 (2H, m), 3.60–3.79 (4H, m), 4.57–4.62 (1H, m), 4.95 (2H, s), 6.87 (2H, d, J=8.5 Hz), 7.22 (1H, s), 7.29 (2H, d, J=8.6 Hz), 7.40 (1H, s), 7.65 (1H, d, J=8.5 Hz), 7.76–7.82 (2H, m), 7.89 (1H, s), 7.98 (1H, d, J=8.6 Hz), 8.08 (1H, d, J=9.2 Hz), 8.43 (1H, s), 8.69 (1H, s), 9.15–9.25 (3H, m), 9.47 (2H, s).

The following compound of Example 91 was obtained in the same manner of Example 32.

EXAMPLE 91

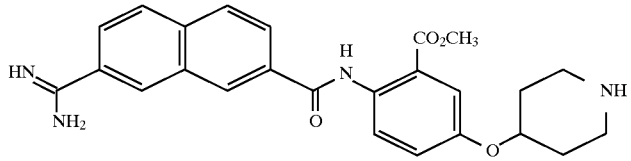

Methyl N-[(7-amidino-2-naphthyl)methyl]-5-[(4-piperidyl)oxy]anthranilate dihydrochloride Starting compound: methyl 5-[(1-t-butoxycarbonyl-4-piperidyl)oxy]-N-[(7-cyano-2-naphthyl)methyl]anthranilate.

Mass spectrometry data (m/z): 433 (M-2HCl+1)$^+$.

Nuclear magnetic resonance spectrum (DMSO-$d_6$, TMS internal standard) δ: 1.71–1.82 (2H, m), 1.95–2.06 (2H, m), 2.93–3.05 (2H, m), 3.12–3.22 (2H, m), 3.84 (3H, s), 4.36–4.42 (1H, m), 4.69 (2H, s), 6.68 (1H, d, J=9.2 Hz), 7.09 (1H, dd, J=9.1, 3.1 Hz), 7.43 (1H, d, J=3.1 Hz), 7.72 (1H, d, J=8.5 Hz), 7.81 (1H, d, J=8.5 Hz), 7.90 (1H, s), 7.98 (1H, bs), 8.06 (1H, d, J=8.5 Hz), 8.12 (1H, d, J=8.5 Hz), 8.45 (1H, s), 8.80–9.03 (2H, m), 9.22 (2H, s), 9.47 (2H, s).

The following compound of Example 92 was obtained in the same manner as described in Example 12.

EXAMPLE 92

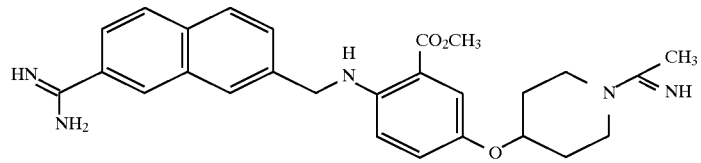

Methyl N-[(7-amidino-2-naphthyl)methyl]-5-[(1-acetoimidoyl-4-piperidyl)oxy]anthranilate dihydrochloride Starting compound: methyl N-[(7-amidino-2-naphthyl]methyl]-5-(4-piperidyloxy)anthranilate dihydrochloride.

Mass spectrometry data (m/z): 474 (M-2HCl+1)$^+$.

Nuclear magnetic resonance spectrum (DMSO-d$_6$, TMS internal standard) δ: 1.61–1.76 (2H, m), 1.90–2.01 (2H, m), 2.28 (3H, s), 3.45–3.80 (4H, m), 3.84 (3H, s), 4.42–4.49 (1H, m), 4.70 (2H, s), 6.69 (1H, d, J=9.1 Hz), 7.10 (1H, dd, J=9.1, 3.0 Hz), 7.43 (1H, d, J=3.1 Hz), 7.72 (1H, d, J=8.5 Hz), 7.82 (1H, d, J=8.5 Hz), 7.97 (1H, s), 8.0 (1H, bs), 8.06 (1H, d, J=8.5 Hz), 8.13 (1H, d, J=8.5 Hz), 8.47 (1H, s), 8.78 (1H, s), 9.25–9.35 (3H, m), 9.50 (2H, m).

EXAMPLE 93

Ethyl [N-[(7-amidino-2-naphthyl]methyl]-N-[4-[(4-piperidyl)oxy]phenyl]sulfamoyl]acetate dihydrochloride (490 mg) was dissolved in 1 ml of ethanol, 5 ml of ethanol which has been saturated with ammonia at 10° C. was added, and the mixture was stirred at 0° C. for 2 days. The reaction solution was evaporated, and the resulting residue was purified by an ODS (YMC-GEL ODS-A 120-230/70) column chromatography using water as the eluent to give 318 mg of [N-[(7-amidino-2-naphthyl)methyl]-N-[4-(4-piperidyl)oxy]phenyl]sulfamoyl]acetamide.

Mass spectrometry data (m/z): 496 (M+1)$^+$.

Nuclear magnetic resonance spectrum (DMSO-d$_6$, TMS internal standard) δ: 1.50–1.98 (2H, m), 1.86–1.94 (2H, m), 2.68–2.73 (2H, s), 2.96–3.06 (2H, m), 4.08 (2H, s), 4.38–4.42 (1H, m), 5.01 (2H, s), 6.89 (2H, d, J=8.6 Hz), 7.36 (2H, d, J=8.5 Hz), 7.53 (1H, s), 7.65 (1H, d, J=8.6 Hz), 7.89 (1H, d, J=6.7 Hz), 7.88 (2H, s), 8.00 (1H, d, J=8.5 Hz), 8.07 (1H, d, J=9.2 Hz), 8.42 (1H, s).

The following compound of Example 94 was obtained in the same manner as described in Example 23.

EXAMPLE 94

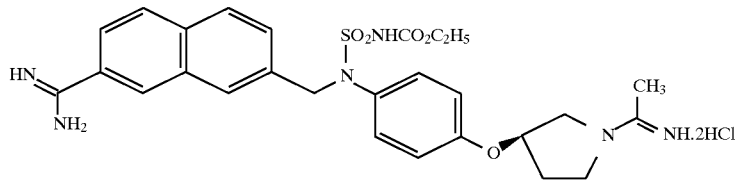

Ethyl N-[N-[4-[[(3S)-1-acetoimidoyl-3-pyrrolidinyl)oxy]phenyl]-N-[(7-amidino-2-naphthyl)methyl]sulfamoyl]carbamate dihydrochloride Starting compound: ethyl N-[N-[4-[[(3S)-1-t-butoxycarbonyl-3-pyrrolidinyl]oxy]phenyl]-N-[(7-cyano-2-naphthyl)methyl]sulfamoyl]carbamate.

Mass spectrometry data (m/z): 553 (M-2HCl+1)$^+$.

Nuclear magnetic resonance spectrum (DMSO-d$_6$, TMS internal standard) δ: 1.27 (3H, t, J=7.3 Hz), 2.07–2.30 (5H, m), 3.33–3.95 (4H, m), 4.23 (2H, q, J=7.3 Hz), 5.05–5.22 (2H, m), 6.90–6.99 (2H, m), 7.23–7.32 (2H, m), 7.64 (1H, d, J=8.5 Hz), 7.81 (1H, d, J=8.5 Hz), 7.92 (1H, d, J=4.3 Hz), 8.03 (1H, d, J=8.5 Hz), 8.10 (1H, d, J=8.5 Hz), 8.40–8.52 (2H, m), 9.15–9.30 (3H, m), 9.48 (2H, s), 11.54 (1H, s).

The following compounds of Examples 95 to 97 were obtained in the same manner as described in Example 32.

EXAMPLE 95

Ethyl 2-[N-[(7-amidino-2-naphthyl)methyl]-N-[4-[(4-piperidyl)oxy]phenyl]sulfamoyl]propionate dihydrochloride Starting compound: ethyl 2-[N-[4-[(1-t-butoxycarbonyl-4-piperidyl)oxy]phenyl]-N-[(7-cyano-2-naphthyl)methyl]sulfamoyl]propionate.

Mass spectrometry data (m/z): 539 (M-2HCl+1)$^+$.

Nuclear magnetic resonance spectrum (DMSO-d$_6$, TMS internal standard) δ: 1.29 (3H, t, J=7.3 Hz), 1.50–1.55 (5H, m), 1.84–1.96 (2H, m), 2.69–2.73 (2H, m), 2.99–3.02 (2H, m), 4.25–4.29 (2H, m), 4.39–4.42 (2H, m), 4.99 (1H, d, J=19.3 Hz), 5.11 (1H, d, J=15.9 Hz), 6.91 (2H, d, J=9.2 Hz), 7.32 (2H, d, J=9.2 Hz), 7.65 (1H, d, J=8.5 Hz), 7.82 (1H, d, J=8.5 Hz), 7.89 (1H, s), 8.03 (1H, d, J=8.5 Hz), 8.00 (1H, d, J=8.5 Hz), 8.44 (1H, s).

EXAMPLE 96

Ethyl 2-[N-[(7-amidino-2-naphthyl)methyl]-N-[4-[(4-piperidyl)oxy]phenyl]sulfamoyl]valerate dihydrochloride Starting compound: ethyl 2-[N-[4-[[(1-t-butoxycarbonyl-4-piperidyl)oxy]phenyl]-N-[(7-cyano-2-naphthyl)methyl]sulfamoyl]valerate.

Mass spectrometry data (m/z): 567 (M-2HCl+1)$^+$.

Nuclear magnetic resonance spectrum (DMSO-d$_6$, TMS internal standard) δ: 0.89 (3H, t, J=7.3 Hz), 1.25 (3H, t, J=7.3 Hz), 1.30–1.36 (2H, m), 1.51–1.55 (2H, m), 1.81–2.02 (4H, m), 2.68–2.72 (2H, m), 2.97–3.00 (2H, m), 4.24–4.29 (3H, m), 4.40–4.43 (1H, m), 5.00 (1H, d, J=15.2 Hz), 5.07 (1H, d, J=15.8 Hz), 6.89 (2H, d, J=9.1 Hz), 7.28 (2H, d, J=9.1 Hz), 7.62 (1H, d, J=6.7 Hz), 7.80 (1H, d, J=6.7 Hz), 7.86 (1H, s), 8.01 (1H, d, J=8.5 Hz), 8.08 (1H, d, J=8.5 Hz), 8.41 (1H, s).

EXAMPLE 97

Ethyl 2-[N-[(7-amidino-2-naphthyl)methyl]-N-[4-[(4-piperidyl)oxy]phenyl]sulfamoyl]butylate dihydrochloride Starting compound: ethyl 2-[N-[4-[[(1-t-butoxycarbonyl-4-piperidyl)oxy]phenyl]-N-[(7-cyano-2-naphthyl)methyl]sulfamoyl]butylate.

Mass spectrometry data (m/z): 553 (M-2HCl+1)$^+$.

Nuclear magnetic resonance spectrum (DMSO-d$_6$, TMS internal standard) δ: 0.94 (3H, t, J=7.3 Hz), 1.26 (3H, t, J=7.3 Hz), 1.49–1.51 (2H, m), 1.88–1.90 (2H, m), 1.98–2.05 (2H, m), 2.50–2.69 (2H, m), 2.96–2.99 (2H, m), 4.22–4.29 (3H, m), 4.38–4.40 (1H, m), 4.98 (1H, d, J=15.3 Hz), 5.06 (1H, d, J=15.3 Hz), 6.87 (2H, d, J=9.2 Hz), 7.28 (2H, d, J=8.5 Hz), 7.62 (1H, d, J=8.5 Hz), 7.80 (1H, d, J=8.6 Hz), 7.86 (1H, s), 8.00 (1H, d, J=8.6 Hz), 8.08 (1H, d, J=8.5 Hz), 8.41 (1H, s).

The following compounds of Examples 98 to 107 were obtained in the same manner as described in Example 12.

EXAMPLE 98

Ethyl 2-[N-[4-[(1-acetoimidoyl-4-piperidyl)oxy]phenyl]-N-[(7-amidino-2-naphthyl)methyl]sulfamoyl]propionate dihydrochloride Starting compound: ethyl 2-[N-[(7-amidino-2-naphthyl)methyl]-N-[4-[(4-piperidyl)oxy]phenyl]sulfamoyl]propionate dihydrochloride.

Mass spectrometry data (m/z): 580 (M-2HCl+1)$^+$.

Nuclear magnetic resonance spectrum (DMSO-d$_6$, TMS internal standard) δ: 1.27 (3H, t, J=7.3 Hz), 1.53 (3H, d, J=7.3 Hz), 1.61–1.76 (2H, m), 1.92–2.06 (2H, m), 2.29 (3H, s), 3.42–3.52 (2H, m), 3.62–3.80 (2H, m), 4.25 (2H, q, J=7.3 Hz), 4.41 (1H, q, J=6.7 Hz), 4.63–4.64 (1H, m), 4.99 (1H, d, J=15.3 Hz), 5.10 (1H, d, J=15.3 Hz), 6.94 (2H, d, J=8.5 Hz), 7.32 (2H, d, J=8.5 Hz), 7.64 (1H, d, J=8.5 Hz), 7.84–7.88 (3H, m), 8.02 (1H, d, J=8.5 Hz), 8.09 (1H, d, J=8.5 Hz), 8.50 (1H, s), 9.37 (6H, br).

EXAMPLE 99

Ethyl 2-[N-[4-[(1-acetoimidoyl-4-piperidyl)oxy]phenyl]-N-[(7-amidino-2-naphthyl)methyl]sulfamoyl]butylate dihydrochloride Starting compound: ethyl 2-[N-[(7-amidino-2-naphthyl)methyl]-N-[4-[(4-piperidyl)oxy]phenyl]sulfamoyl]butylate dihydrochloride.

Mass spectrometry data (m/z): 594 (M-2HCl+1)+.

Nuclear magnetic resonance spectrum (DMSO-d$_6$, TMS internal standard) δ: 0.95 (3H, t, J=7.3 Hz), 1.26 (3H, t, J=7.3 Hz), 1.50–1.66 (2H, br), 1.99–2.08 (4H, m), 2.29 (3H, s), 3.40–3.51 (2H, br), 3.71–3.79 (2H, br), 4.24–4.30 (3H, m), 4.63–4.64 (1H, m), 5.03 (1H, d, J=15.3 Hz), 5.05 (1H, d, J=15.3 Hz), 6.93 (2H, d, J=9.2 Hz), 7.31 (2H, d, J=9.2 Hz), 7.63 (1H, d, J=9.8 Hz), 7.85–7.87 (2H, m), 8.02 (1H, d, J=8.5 Hz), 8.09 (1H, d, J=8.5 Hz), 8.51 (1H, s), 9.43 (6H, br).

EXAMPLE 100

Ethyl 2-[N-[4-[(1-acetoimidoyl-4-piperidyl)oxy]phenyl]-N-[(7-amidino-2-naphthyl)methyl]sulfamoyl]valerate dihydrochloride Starting compound: ethyl 2-[N-[(7-amidino-2-naphthyl)methyl]-N-[4-[(4-piperidyl)oxy]phenyl]sulfamoyl]valerate dihydrochloride.

Mass spectrometry data (m/z): 608 (M-2HCl+1)+.

Nuclear magnetic resonance spectrum (DMSO-d$_6$, TMS internal standard) δ: 0.89 (3H, t, J=7.3 Hz), 1.25 (3H, t, J=7.3 Hz), 1.30–1.36 (2H, m), 1.67 (2H, br), 1.88–2.00 (4H, m), 2.28 (3H, s), 3.49 (2H, br), 3.75 (2H, br), 4.24–4.28 (3H, m), 4.60–4.68 (1H, m), 5.01 (1H, d, J=15.9 Hz), 5.08 (1H, d, J=15.9 Hz), 6.94 (2H, d, J=9.2 Hz), 7.31 (2H, d, J=8.6 Hz), 7.63 (1H, d, J=8.6 Hz), 7.84 (1H, d, J=8.5 Hz), 7.87 (1H, s), 8.02 (1H, d, J=8.5 Hz), 8.09 (1H, d, J=8.5 Hz), 8.49 (1H, s), 9.39 (6H, br).

EXAMPLE 101

[N-[4-[(1-Acetoimidoyl-4-piperidyl)oxy]phenyl]-N-[(7-amidino-2-naphthyl)methyl]sulfamoyl]acetamide dihydrochloride Starting compound: [N-[(7-amidino-2-naphthyl)methyl]-N-[4-[(4-piperidyl)oxy]phenyl]sulfamoyl]acetamide.

Mass spectrometry data (m/z): 537 (M-2HCl+1)+.

Nuclear magnetic resonance spectrum (DMSO-d$_6$, TMS internal standard) δ: 1.60–1.72 (2H, m), 1.94–2.02 (2H, m), 2.26 (3H, s), 3.42–3.51 (2H, m), 3.64–3.78 (2H, m), 4.07 (2H, s), 4.58–4.64 (1H, m), 5.01 (2H, s), 6.93 (2H, d, J=8.6 Hz), 7.38 (2H, d, J=9.2 Hz), 7.52 (1H, s), 7.66 (1H, d, J=8.6 Hz), 7.80 (1H, d, J=8.6 Hz), 7.84 (1H, s), 7.90 (1H, s), 8.00 (1H, d, J=8.6 Hz), 8.08 (1H, d, J=9.2 Hz), 8.44 (1H, s), 8.84–9.14 (5H, br).

The following compound of Example 102 was obtained in the same manner as described in Example 30.

EXAMPLE 102

2-[N-[4-[(1-Acetoimidoyl-4-piperidyl)oxy]phenyl]-N-[(7-amidino-2-naphthyl)methyl]sulfamoyl]propionic acid dihydrochloride Starting compound: ethyl 2-[N-[4-[(1-acetoimidoyl-4-piperidyl)oxy]phenyl]-N-[(7-amidino-2-naphthyl)methyl]sulfamoyl]propionate dihydrochloride.

Mass spectrometry data (m/z): 552 (M-2HCl+1)+.

Nuclear magnetic resonance spectrum (DMSO-d$_6$, TMS internal standard) δ: 1.50 (3H, d, J=6.7 Hz), 1.57–1.71 (2H, m), 1.91–2.04 (2H, m), 2.27 (3H, s), 3.40–3.54 (2H, m), 3.64–3.82 (2H, m), 4.25–4.29 (1H, m), 4.58–4.62 (1H, m), 4.97 (1H, d, J=15.3 Hz), 5.10 (1H, d, J=15.3 Hz), 6.92 (2H, d, J=9.2 Hz), 7.33 (2H, d, J=9.2 Hz), 7.64 (1H, d, J=8.5 Hz), 7.82 (1H, d, J=8.5 Hz), 7.88 (1H, s), 8.02 (1H, d, J=8.5 Hz), 8.09 (1H, d, J=9.2 Hz), 8.47 (1H, s), 8.79 (1H, s), 9.31–9.33 (3H, br), 9.51 (2H, s).

Chemical structures of the compounds obtained in the aforementioned Examples 1 to 79, 82 to 90, 93, and 95 to 102 are shown in the following Tables 2 to 11.

TABLE 2

| Example No. | R¹ | R⁷ | Salt |
|---|---|---|---|
| 1 | O=C(CH₃)– | H | 2 HCl |
| 2 | O=C(NH₂)–O– | H | 2 HCl |

TABLE 2-continued

[Structure: naphthalene with HN=C(NH2)- group at one end, and -CH2-N(R1)-phenyl-O-piperidine-N-R7 at the other end]

| Example No. | R¹ | R⁷ | Salt |
|---|---|---|---|
| 3 | -C(=O)-cyclopropyl | H | 2 HCl |
| 4 | -C(=O)-phenyl | H | 2 HCl |
| 5 | -C(=O)-C₂H₅ | H | 2 HCl |
| 6 | -C(=O)-cyclohexyl | H | 2 HCl |
| 7 | -C(=O)-(1-naphthyl) | H | 2 HCl |
| 8 | -C(=O)-(2-fluorophenyl) | H | 2 HCl |
| 9 | -C(=O)-(3-methoxyphenyl) | H | 2 HCl |
| 10 | -C(=O)-(2-thienyl) | H | 2 HCl |

TABLE 3
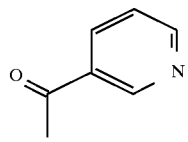
| Example No. | R¹ | R⁷ | Salt |
|---|---|---|---|
| 11 | 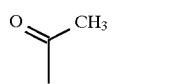 | H | 2 HCl |
| 12 | 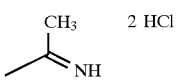 | 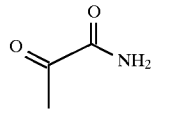 | 2 HCl |
| 13 | 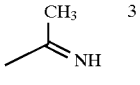 | 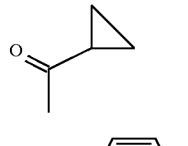 | 3 HCl |
| 14 | 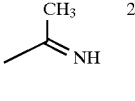 | 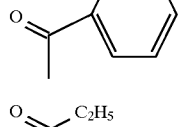 | 2 HCl |
| 15 | 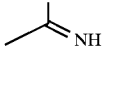 | 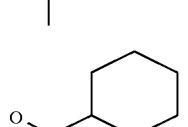 | 2 HCl |
| 16 | 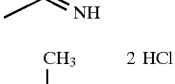 | 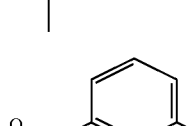 | 2 HCl |
| 17 | 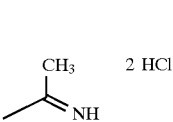 | 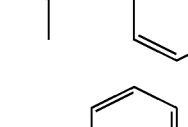 | 2 HCl |
| 18 |  | 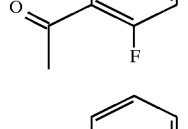 | 2 HCl |
| 19 |  | 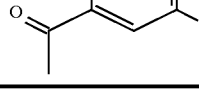 | 2 HCl |
| 20 | 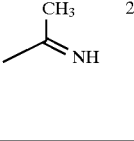 | | 2 HCl |

TABLE 4
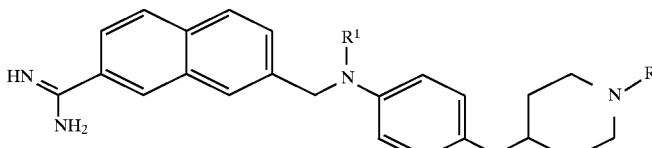
| Example No. | R¹ | R⁷ | Salt |
|---|---|---|---|
| 21 |  | 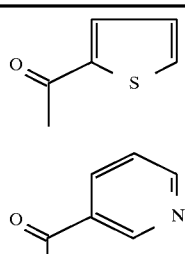 | 2 HCl |
| 22 |  | 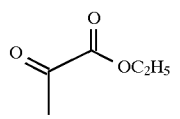 | 3 HCl |
| 23 |  | 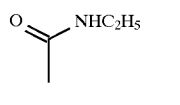 | 2 HCl |
| 24 |  | 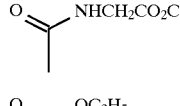 | 2 HCl |
| 25 |  | 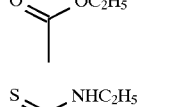 | 2 HCl |
| 26 |  | 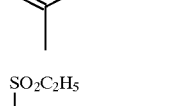 | 2 HCl |
| 27 |  | 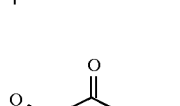 | 2 HCl |
| 28 | SO₂C₂H₅ |  | 2 HCl |
| 29 | 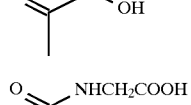 |  | 2 HCl |
| 30 | 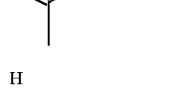 |  | 2 HCl |
| 31 | H |  | 2 HCl |

TABLE 5
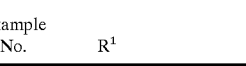
| Example No. | R¹ | R⁷ | Salt |
|---|---|---|---|
| 32 | 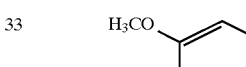 | H | 2 HCl |
| 33 | 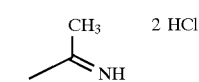 |  | 2 HCl |
| 34 |  | H | 2 HCl |
| 35 | 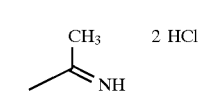 |  | 2 HCl |
| 36 |  | H | 3 HCl |
| 37 | 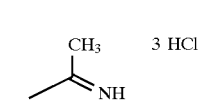 |  | 3 HCl |
| 38 |  | H | 3 HCl |
| 39 | 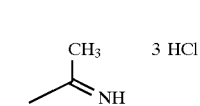 | 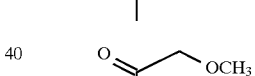 | 3 HCl |
| 40 | 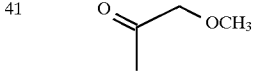 | H | 2 HCl |
| 41 | 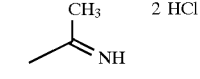 | 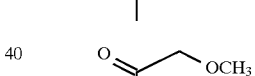 | 2 HCl |

TABLE 6

| Example No. | R¹ | R⁷ | Salt |
|---|---|---|---|
| 42 | O=C(CH₃)CH₂-CO₂C₂H₅ | H | 2 HCl |
| 43 | O=C(CH₃)CH₂-CO₂C₂H₅ | C(CH₃)=NH | 2 HCl |
| 44 | O=C(CH₃)CH₂CH₂-CO₂C₂H₅ | H | 2 HCl |
| 45 | O=C(CH₃)CH₂CH₂-CO₂C₂H₅ | C(CH₃)=NH | 2 HCl |
| 46 | O=C-(2,6-difluorophenyl) | H | 2 HCl |
| 47 | O=C-(2,6-difluorophenyl) | C(CH₃)=NH | 2 HCl |
| 48 | O=C(CH₃)CH₂-N(CH₃)₂ | H | 3 HCl |
| 49 | O=C(CH₃)CH₂-N(CH₃)₂ | C(CH₃)=NH | 3 HCl |
| 50 | O=C(CH₃)-NHCO₂C₂H₅ | H | 2 HCl |
| 51 | O=C(CH₃)-NHCO₂C₂H₅ | C(CH₃)=NH | 2 HCl |

TABLE 7
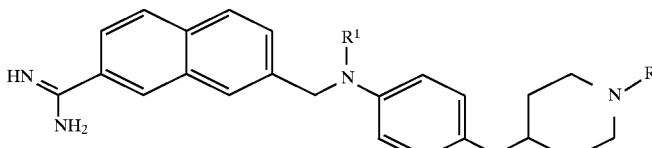
| Example No. | R¹ | R⁷ | Salt |
|---|---|---|---|
| 52 | 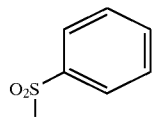 | H | 2 HCl |
| 53 | 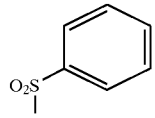 | 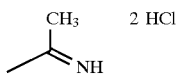 | 2 HCl |
| 54 | O₂S—CH₃ |  | 2 HCl |
| 55 | 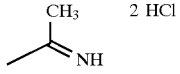 | 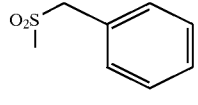 | 2 HCl |
| 56 | 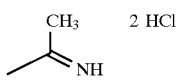 | 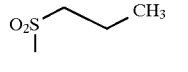 | 2 HCl |
| 57 | 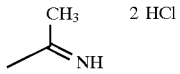 | H | 2 HCl |
| 58 | 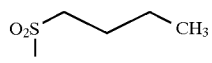 | 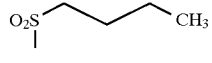 | 2 HCl |
| 59 | O₂S—CF₃ | H | 2 HCl |
| 60 | O₂S—CF₃ | 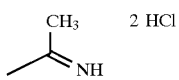 | 2 HCl |
| 61 |  | H | 2 HCl |

TABLE 8
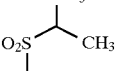
| Example No. | R¹ | R⁷ | Salt |
|---|---|---|---|
| 62 | 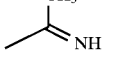 |  | 2 HCl |
| 63 | O₂SNHCO₂C₂H₅ | 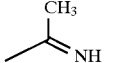 | 2 HCl |
| 64 | 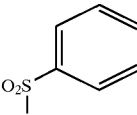 | H | 2 HCl |
| 65 | 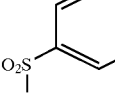 | 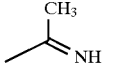 | 2 HCl |
| 66 | 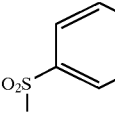 | 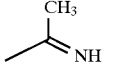 | 2 HCl |
| 67 | 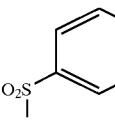 | 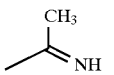 | 2 HCl |
| 68 | 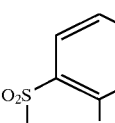 | 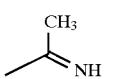 | 2 HCl |
| 69 | O₂SNH₂ |  | 2 HCl |
| 70 | 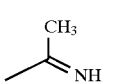 | H | 2 HCl |
| 71 | 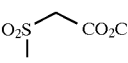 | 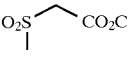 | 2 HCl |

TABLE 9

[Structure: 7-amidino-naphthalene-2-CH2-N(R1)-C6H4-O-(4-piperidinyl with N-R7)]

| Example No. | R¹ | R⁷ | Salt |
|---|---|---|---|
| 72 | $O_2S$-CH$_2$CH$_2$-CO$_2$C$_2$H$_5$ | H | 2 HCl |
| 73 | $O_2S$-CH$_2$CH$_2$-CO$_2$C$_2$H$_5$ | C(CH$_3$)=NH | 2 HCl |
| 74 | $O_2S$-(4-C$_6$H$_4$)-CO$_2$H | C(CH$_3$)=NH | 2 HCl |
| 75 | $O_2S$-CH$_2$-CO$_2$H | C(CH$_3$)=NH | 2 HCl |
| 76 | $O_2S$-(4-C$_6$H$_4$)-NH$_2$ | H | 3 HCl |
| 77 | $O_2S$-(4-C$_6$H$_4$)-NH$_2$ | C(CH$_3$)=NH | 3 HCl |
| 78 | O$_2$SNHCH$_3$ | H | 2 HCl |
| 79 | O$_2$SNHCH$_3$ | C(CH$_3$)=NH | 2 HCl |
| 82 | $O_2S$-N(CH$_3$)-CO$_2$C$_2$H$_5$ | H | 2 HCl |
| 83 | $O_2S$-N(CH$_3$)-CO$_2$C$_2$H$_5$ | C(CH$_3$)=NH | 2 HCl |

TABLE 10

[Structure: naphthalene with HN=C(NH2)- on one end and -CH2-N(R1)-C6H4-O-(piperidine-N-R7) on the other]

| Example No. | R¹ | R⁷ | Salt |
|---|---|---|---|
| 84 | O₂S-N(CH₂CO₂CH₃)-CO₂C₂H₅ | H | 2 HCl |
| 85 | O₂S-N(CH₂CO₂CH₃)-CO₂C₂H₅ | C(CH₃)=NH | 2 HCl |
| 86 | O₂S-N(CH₂CO₂H)-CO₂C₂H₅ | C(CH₃)=NH | 2 HCl |
| 87 | O₂S-N(H)-CH₂CO₂C₂H₅ | H | 2 HCl |
| 88 | O₂S-N(H)-CH₂CO₂C₂H₅ | C(CH₃)=NH | 2 HCl |
| 89 | O₂S-N(H)-CH₂CO₂H | C(CH₃)=NH | 2 HCl |
| 90 | O₂S-N(H)-CH₂CONH₂ | C(CH₃)=NH | 2 HCl |
| 93 | O₂S-CH₂-CONH₂ | H | — |
| 95 | O₂S-CH(CH₃)-CO₂C₂H₅ | H | 2 HCl |
| 96 | O₂S-CH(C₃H₇)-CO₂C₂H₅ | H | 2 HCl |

TABLE 11

[Structure: 7-amidino-naphthyl-CH2-N(R1)-phenyl-O-(4-piperidyl)-N-R7]

| Example No. | R¹ | R⁷ | Salt |
|---|---|---|---|
| 97 | O₂S(-CH(C₂H₅)-CO₂C₂H₅) | H | 2 HCl |
| 98 | O₂S(-CH(CH₃)-CO₂C₂H₅) | C(CH₃)=NH | 2 HCl |
| 99 | O₂S(-CH(C₂H₅)-CO₂C₂H₅) | C(CH₃)=NH | 2 HCl |
| 100 | O₂S(-CH(C₃H₇)-CO₂C₂H₅) | C(CH₃)=NH | 2 HCl |
| 101 | O₂S(-CH₂-CONH₂) | C(CH₃)=NH | 2 HCl |
| 102 | O₂S(-CH(CH₃)-CO₂H) | C(CH₃)=NH | 2 HCl |

The following compounds (1A) to (53A) can be produced easily in almost the same manner as described in the aforementioned Examples and production methods or by applying slight modifications which are obvious to those skilled in the art.

(1A) [N-[4-[(1-Acetoimidoyl-4-piperidyl)oxy]phenyl]-N-[(7-amidino-2-naphthyl)methyl]-2-thiophene sulfonamide dihydrochloride.

(2A) [N-[4-[(1-Acetoimidoyl-4-piperidyl)oxy]phenyl]-N-[(7-amidino-2-naphthyl)methyl]-2-fluorobenzenesulfonamide dihydrochloride.

(3A) [N-[4-[(1-Acetoimidoyl-4-piperidyl)oxy]phenyl]-N-[(7-amidino-2-naphthyl)methyl]methylsulfonylmethanesulfonamide dihydrochloride.

(4A) [N-[4-[(1-Acetoimidoyl-4-piperidyl)oxy]phenyl]-N-[(6-amidino-2-naphthyl)methyl]oxamide dihydrochloride.

(5A) [N-[4-[(1-Acetoimidoyl-4-piperidyl)oxy]phenyl]-N-[(5-amidino-2-naphthyl)methyl]oxamide dihydrochloride.

(6A) [N-[4-[(1-Acetoimidoyl-4-piperidyl)oxy]phenyl]-N-[(8-amidino-2-naphthyl)methyl]oxamide dihydrochloride.

(7A) [N-[4-[(1-Acetoimidoyl-3-piperidyl)oxy]phenyl]-N-[(7-amidino-2-naphthyl)methyl]oxamide dihydrochloride.

(8A) [N-[4-[(1-Acetoimidoyl-2-piperidyl)oxy]phenyl]-N-[(7-amidino-2-naphthyl)methyl]oxamide dihydrochloride.

(9A) N-[(7-Amidino-2-naphthyl)methyl]-N-[4-[(1-iminopropyl-4-piperidyl)oxy]phenyl]oxamide dihydrochloride.

(10A) N-[(7-Amidino-2-naphthyl)methyl]-N-[4-[(3-pyrrolidinyl)oxy]phenyl]oxamide dihydrochloride.

(11A) N-[(7-Amidino-2-naphthyl)methyl]-N-[4-[(3-pyrrolidinyl)oxy]phenyl]oxamate dihydrochloride.

(12A) 1-[(7-Amidino-2-naphthyl)methyl]-1-[4-[(3-pyrrolidinyl)oxy]phenyl]-3-ethylurea dihydrochloride.

(13A) N-[(7-Amidino-2-naphthyl)methyl]-N-[4-[(3-pyrrolidinyl)oxy]phenyl]ethoxycarbonylaniline dihydrochloride.

(14A) N-[(7-Amidino-2-naphthyl)methyl]-N-[4-[(3-pyrrolidinyl)oxy]phenyl]acetamide dihydrochloride.

(15A) N-[(7-Amidino-2-naphthyl)methyl]-N-[4-[(3-pyrrolidinyl)oxy]phenyl]ethanesulfonamide dihydrochloride.

(16A) N-[4-[(1-Acetoimidoyl-3-pyrrolidinyl)oxy]phenyl]-N-[(7-amidino-2-naphthyl)methyl]oxamide dihydrochloride.

(17A) N-[4-[(1-Acetoimidoyl-3-pyrrolidinyl)oxy]phenyl]-N-[(7-amidino-2-naphthyl)methyl]oxamate dihydrochloride.

(18A) 1-[4-[(1-Acetoimidoyl-3-pyrrolidinyl)oxy]phenyl]-1-[(7-amidino-2-naphthyl)methyl]-3-ethylurea dihydrochloride.

(19A) N-[4-[(1-Acetoimidoyl-3-pyrrolidinyl)oxy]phenyl]-N-[(7-amidino-2-naphthyl)methyl]ethoxycarbonylaniline dihydrochloride.

(20A) N-[4-[(1-Acetoimidoyl-3-pyrrolidinyl)oxy]phenyl]-N-[(7-amidino-2-naphthyl)methyl]acetamide dihydrochloride.
(21A) N-[4-[(1-Acetoimidoyl-3-pyrrolidinyl)oxy]phenyl]-N-[(7-amidino-2-naphthyl)methyl]ethanesulfonamide dihydrochloride.
(22A) N-[4-[(1-Acetoimidoyl-4-piperidyl)oxy]phenyl]-N-[(7-amidino-2-naphthyl)methyl]-2-aminoethanesulfonamide trihydrochloride.
(23A) N-[4-[(1-Acetoimidoyl-4-piperidyl)oxy]phenyl]-N-[(7-amidino-2-naphthyl)methyl]-2-dimethylaminoethanesulfonamide trihydrochloride.
(24A) N-[4-[(1-Acetoimidoyl-4-piperidyl)oxy]phenyl]-N-[(7-amidino-2-naphthyl)methyl]-2-hydroxyethanesulfonamide dihydrochloride.
(25A) N-[4-[(1-Acetoimidoyl-4-piperidyl)oxy]phenyl]-N-[(7-amidino-2-naphthyl)methyl]-2-methoxyethanesulfonamide dihydrochloride.
(26A) [N-[4-[(1-Acetoimidoyl-4-piperidyl)oxy]phenyl]-N-[(7-amidino-2-naphthyl)methyl]sulfamoyl]propionic acid dihydrochloride.
(27A) Methyl N-[N-[4-[(1-acetoimidoyl-4-piperidyl)oxy]phenyl]-N-[(7-amidino-2-naphthyl)methyl]sulfamoyl]glycinate dihydrochloride.
(28A) N-[N-[4-[(1-Acetoimidoyl-4-piperidyl)oxy]phenyl]-N-[(7-amidino-2-naphthyl)methyl]sulfamoyl]-N-methylglycine dihydrochloride.
(29A) Methyl N-[N-[4-[(1-acetoimidoyl-4-piperidyl)oxy]phenyl]-N-[(7-amidino-2-naphthyl)methyl]sulfamoyl]1-N-methylglycinate dihydrochloride.
(30A) N-[N-[4-[(1-Acetoimidoyl-4-piperidyl)oxy]phenyl]-N-[(7-amidino-2-naphthyl)methyl]sulfamoyl]-N-methylglycinamide dihydrochloride.
(31A) N-[N-[4-[(1-Acetoimidoyl-4-piperidyl)oxy]phenyl]-N-[(7-amidino-2-naphthyl)methyl]sulfamoyl]-N-ethoxycarbonylglycinamide dihydrochloride.
(32A) Methyl N-[N-[4-[(1-acetoimidoyl-4-piperidyl)oxy]phenyl]-N-[(7-amidino-2-naphthyl)methyl]sulfamoyl]carbamate dihydrochloride.
(33A) N-[4-[(1-Acetoimidoyl-4-piperidyl)oxy]phenyl]-N-[(7-amidino-2-naphthoyl)sulfamoyl]acetic acid dihydrochloride.
(34A) Ethyl N-[N-[4-[(1-acetoimidoyl-4-piperidyl)oxy]phenyl]-N-[(7-amidino-2-naphthoyl)sulfamoyl]carbamate dihydrochloride.
(35A) N-[N-[4-[(1-Acetoimidoyl-4-piperidyl)oxy]phenyl]-N-[(7-amidino-2-naphthyl)methyl]sulfamoyl]urea.
(36A) N-[N-[4-[(1-Acetoimidoyl-4-piperidyl)oxy]phenyl]-N-[(7-amidino-2-naphthyl)methyl]sulfamoyl]-N'-methylurea.
(37A) N-[N-[4-[(1-Acetoimidoyl-4-piperidyl)oxy]phenyl]-N-[(7-amidino-2-naphthyl)methyl]sulfamoyl]methanesulfonamide.
(38A) N-[N-[4-[(1-Acetoimidoyl-4-piperidyl)oxy]phenyl]-N-[(7-amidino-2-naphthyl)methyl]sulfamoyl]-N'-methylthiourea.
(39A) N-[4-[(1-Acetoimidoyl-4-piperidyl)oxy]phenyl]-N'-acetyl-N-[(7-amidino-2-naphthyl)methyl]sulfamide.
(40A) 2-[N-[4-[(1-Acetoimidoyl-4-piperidyl)oxy]phenyl]-N-[(7-amidino-2-naphthyl)methyl]sulfamoyl]butyric acid.
(41A) 2-[N-[4-[(1-Acetoimidoyl-4-piperidyl)oxy]phenyl]-N-[(7-amidino-2-naphthyl)methyl]sulfamoyl]valeric acid.
(42A) 2-[N-[4-[(1-Acetoimidoyl-4-piperidyl)oxy]phenyl]-N-[(7-amidino-2-naphthyl)methyl]sulfamoyl]isovaleric acid.
(43A) 2-[N-[4-[(1-Acetoimidoyl-4-piperidyl)oxy]phenyl]-N-[(7-amidino-2-naphthyl)methyl]sulfamoyl]-3-phenylpropionic acid.
(44A) [N-[4-[(1-Acetoimidoyl-4-piperidyl)oxy]phenyl]-N-[(7-amidino-2-naphthyl)methyl]difluoroacetic acid.
(45A) 2-[N-[4-[[(1-Acetoimidoyl-4-piperidyl)oxy]phenyl]-N-[(7-amidino-2-naphthyl)methyl]sulfamoyl]isobutyric acid.
(46A) 2-[N-[4-[(1-Acetoimidoyl-4-piperidyl)oxy]phenyl]-N-[(7-amidino-2-naphthyl)methyl]sulfamoyl]-2-ethylbutyric acid.
(47A) 1-[N-[4-[(1-Acetoimidoyl-4-piperidyl)oxy]phenyl]-N-[(7-amidino-2-naphthyl)methyl]sulfamoyl]-1-cyclohexanecarboxylic acid.
(48A) Ethyl 2-[N-[4-[(1-acetoimidoyl-4-piperidyl)oxy]phenyl]-N-[(7-amidino-2-naphthyl)methyl]sulfamoyl]isovalerate.
(49A) Ethyl 2-[N-[4-[(1-acetoimidoyl-4-piperidyl)oxy]phenyl]-N-[(7-amidino-2-naphthyl)methyl]sulfamoyl]-3-phenylpropionate.
(50A) Ethyl [N-[4-[(1-acetoimidoyl-4-piperidyl)oxy]phenyl]-N-[(7-amidino-2-naphthyl)methyl]sulfamoyl]difluoroacetate.
(51A) Ethyl [N-[4-[(1-acetoimidoyl-4-piperidyl)oxy]phenyl]-N-[(7-amidino-2-naphthyl)methyl]sulfamoyl]isobutyrate.
(52A) Ethyl 2-[N-[4-[(1-acetoimidoyl-4-piperidyl)oxy]phenyl]-N-[(7-amidino-2-naphthyl)methyl]sulfamoyl]-2-ethylbutyrate.
(53A) Ethyl 1-[N-[4-[(1-acetoimidoyl-4-piperidyl)oxy]phenyl]-N-[(7-amidino-2-naphthyl)methyl]sulfamoyl]-1-cyclohexanecarboxylate.

We claim:

1. An amidinonaphthyl derivative represented by the following formula (I)

(symbols in the formula have the following meanings;

$R^1$: a group represented by the formula —A—W—$R^4$,

A: a group represented by the formula $$-\overset{\overset{X}{\|}}{C}-,$$

a group represented by the formula $$-\overset{\overset{O}{\|}}{C}-\overset{\overset{O}{\|}}{C}-,$$

or a group represented by the formula —$SO_2$—,

X: an oxygen atom or a sulfur atom,

W: a single bond or a group represented by the formula —$NR^5$—, $R^4$: a hydroxyl group, a lower alkoxy group, a lower alkyl group which may be substituted, a cycloalkyl group which may be substituted, an aryl group which may be substituted, or a heteroaryl group which may be substituted, with the proviso that, when W is a group represented by the formula —NR$^5$—, R$^4$ may further be a hydrogen atom but is not a hydroxyl group or a lower alkoxy group, R$^5$: a hydrogen atom, a carbamoyl group, a lower alkoxycarbonyl group, a mono- or di-lower alkylaminocarbonyl group, a lower alkylsulfonyl group, a mono- or di-lower alkylaminothiocarbonyl group, a lower alkyl group which may be substituted, or a lower alkanoyl group which may be substituted, R$^2$: a lower alkyl group, R$^3$: a hydrogen atom, a halogen atom, a carboxyl group, an amino group, a cyano group, a nitro group, a hydroxyl group, a lower alkoxy group, a lower alkyl group, or a lower alkoxycarbonyl group, B: a lower alkylene group or a carbonyl group, and n: 0 or 1), or a pharmaceutically acceptable salt thereof.

2. The amidinonaphthyl derivative or a pharmaceutically acceptable salt thereof in the meaning of claim 1, wherein the lower alkyl group which may be substituted in the meaning of R$^4$ or R$^5$, the cycloalkyl group which may be substituted in the meaning of R$^4$ or the lower alkanoyl group which may be substituted in the meaning of R$^5$ is a lower alkyl group, a cycloalkyl group or a lower alkanoyl group which may be substituted with a member of the following group C, and the aryl group which may be substituted or the heteroaryl group which may be substituted in the meaning of R$^4$ is an aryl group or a heteroaryl group which may be substituted with a member of the following group D, group C: a halogen atom, a carboxyl group, a carbamoyl group, an amino group, a cyano group, a nitro group, a lower alkanoyl group, a lower alkoxy group, a lower alkoxycarbonyl group, a mono- or di-lower alkylamino group, an aryl group, an aralkyloxy group, an aryloxy group, a mercapto group, a lower alkylthio group, a lower alkylthiocarbonyl group, a hydroxyl group, or a mono- or di-lower alkylaminocarbonyl group group D: a halogen atom, a carboxyl group, an amino group, a cyano group, a nitro group, a hydroxyl group, a lower alkoxy group, a lower alkoxycarbonyl group, a mono- or di-lower alkylamino group, a lower alkanoyl group, or a lower alkyl group which may be substituted with a member of the group C.

3. The amidinonaphthyl derivative or a pharmaceutically acceptable salt thereof according to claim 2, wherein R$^4$ is a hydroxyl group; a lower alkoxy group; a lower alkyl group which may be substituted with a halogen atom, a carboxyl group, a carbamoyl group, an amino group, a lower alkoxy group, a lower alkoxycarbonyl group, a mono- or di-lower alkylamino group or a phenyl group; a cycloalkyl group which may be substituted with a halogen atom, a carboxyl group, a carbamoyl group, an amino group, a lower alkoxy group, a lower alkoxycarbonyl group, a mono- or di-lower alkylamino group or a phenyl group; an aryl group which may be substituted with a halogen atom, an amino group, a nitro group, a carboxyl group, a lower alkoxycarbonyl group or a lower alkoxy group; or a heteroaryl group which may be substituted with a halogen atom, an amino group, a nitro group, a carboxyl group, a lower alkoxycarbonyl group or a lower alkoxy group (with the proviso that, when W is a group represented by the formula —NR$^5$—, R$^4$ may further be a hydrogen atom but is not a hydroxyl group or a lower alkoxy group), R$^5$ is a hydrogen atom; a carbamoyl group; a lower alkoxycarbonyl group; a lower alkanoyl group; a mono- or di-lower alkylaminothiocarbonyl group; or a lower alkyl group which may be substituted with a halogen atom, a carbamoyl group, an amino group, a lower alkoxy group, a lower alkoxycarbonyl group, a mono- or di-lower alkylamino group or a phenyl group, and R$^3$ is a hydrogen atom, a halogen atom, a carboxyl group, a lower alkoxy group, a lower alkyl group, or a lower alkoxycarbonyl group.

4. The amidinonaphthyl derivative or a pharmaceutically acceptable salt thereof according to claim 3, wherein the group represented by the formula —A—W—R$^4$ is a group selected from the group consisting of a lower alkanoyl group which may be substituted with a lower alkoxy group, a lower alkoxycarbonyl group or a mono- or di-lower alkylamino group; an aminocarbonyl group which may be substituted with a lower alkoxycarbonyl group; a lower alkylsulfonyl group which may be substituted with a halogen atom, a carboxyl group, a carbamoyl group, a lower alkoxycarbonyl group or a phenyl group; a mono- or di-lower alkylaminocarbonyl group which may be substituted with a carboxyl group or a lower alkoxycarbonyl group; an aminosulfonyl group which may be substituted with a lower alkoxycarbonyl group; a mono- or di-lower alkylaminosulfonyl group which may be substituted with a carbamoyl group, a carboxyl group or a lower alkoxycarbonyl group; an N-lower alkyl-N-lower alkoxycarbonylaminosulfonyl group which may be substituted with a carboxyl group or a lower alkoxycarbonyl group; a benzoyl group which may be substituted with a carboxyl group, a lower alkoxycarbonyl group, a halogen atom or a lower alkoxy group; a benzenesulfonyl group which may be substituted with an amino group, a nitro group, a carboxyl group or a lower alkoxycarbonyl group; a naphthoyl group; a mono-lower alkylaminothiocarbonyl group; a pyridylcarbonyl group; a thienylcarbonyl group; an aminooxalyl group; or a cycloalkylcarbonyl group, and R$^3$ is a hydrogen atom or a lower alkoxycarbonyl group.

5. The amidinonaphthyl derivative or a pharmaceutically acceptable salt thereof according to any one of claims 1 to 3, wherein A is a group represented by the formula

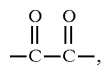

6. The amidinonaphthyl derivative or a pharmaceutically acceptable salt thereof according to any one of claims 1 to 3, wherein A is a group represented by the formula —SO$_2$—.

7. An amidinonaphthyl derivative which is selected from the group consisting of N-[4-[(1-acetoimidoyl-4-piperidyl)oxy]phenyl]-N-[(7-amidino-2-naphthyl)methyl-N'-methylsulfamide, ethyl N-[N-4-[(1acetoimidoyl-4-piperidyl)oxy]phenyl]-N-[(7-amidino-2-naphthyl)methyl]sulfamoyl]carbamate, 4-[N-4-[(1-acetoimidoyl-4-piperidyl)oxy]phenyl]-N-[(7-amidino-2-naphthyl)methyl]sulfamoyl]benzoic acid, [N[4-[(1-acetoimidoyl-4-piperidyl)oxy]phenyl]-N-[(7-amidino-2-naphthyl)methyl]sulfamoyl]acetic acid, ethyl N-[N-[4-[(1-acetoimidoyl-4-piperidyl)oxy]phenyl]-N-[(7-amidino-2-naphthyl)methyl]sulfamoyl]glycinate, N-[N-4-[(1-acetoimidoyl-4-piperidyl)oxy]phenyl]-N-[(7-amidino-2-naphthyl)methyl]sulfamoyl]-N-ethoxycarbonylglycine and N-[N-4-[(1-acetoimidoyl-4-piperidyl)oxy]phenyl]-N-[(7-amidino-2-naphthyl)methyl]sulfamoyl]glycine, or a pharmaceutically acceptable salt thereof.

8. An amidinonaphthyl derivative represented by the following formula (I')

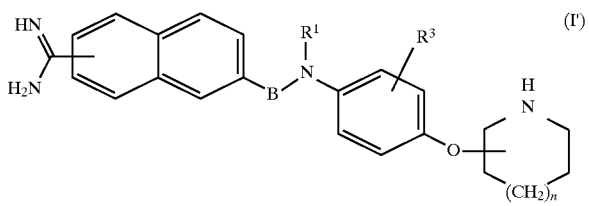

(symbols in the formula have the following meanings;
$R^1$: a group represented by the formula —A—W—$R^4$,
A: a group represented by the formula

a group represented by the formula

or a group represented by the formula —$SO_2$—,
X: an oxygen atom or a sulfur atom,
W: a single bond or a group represented by the formula —$NR^5$—,
$R^4$: a hydroxyl group, a lower alkoxy group, a lower alkyl group which may be substituted, a cycloalkyl group which may be substituted, an aryl group which may be substituted, or a heteroaryl group which may be substituted,
with the proviso that, when W is a group represented by the formula —$NR^5$—, $R^4$ may further be a hydrogen atom but is not a hydroxyl group or a lower alkoxy group,
$R^5$: a hydrogen atom, a carbamoyl group, a lower alkoxycarbonyl group, a mono- or di-lower alkylaminocarbonyl group, a lower alkylsulfonyl group, a mono- or di-lower alkylaminothiocarbonyl group, a lower alkyl group which may be substituted, or a lower alkanoyl group which may be substituted,
$R^3$: a hydrogen atom, a halogen atom, a carboxyl group, an amino group, a cyano group, a nitro group, a hydroxyl group, a lower alkoxy group, a lower alkyl group, or a lower alkoxycarbonyl group,
B: a lower alkylene group or a carbonyl group, and
n: 0 or 1),
or a pharmaceutically acceptable salt thereof.

9. A pharmaceutical composition which comprises the amidinonaphthyl derivative or a pharmaceutically acceptable salt thereof according to claim 1.

10. The pharmaceutical composition according to claim 9, useful for inhibiting activated blood coagulation factor X.

11. The pharmaceutical composition according to claim 10, useful for inhibiting blood coagulation.

12. The pharmaceutical composition according to claim 10, useful for the prevention and/or treatment of a diseases caused by thrombus or embolus.

13. A pharmaceutical composition which comprises the amidinonaphthyl derivative or a pharmaceutically acceptable salt thereof according to claim 2.

14. A pharmaceutical composition which comprises the amidinonaphthyl derivative or a pharmaceutically acceptable salt thereof according to claim 3.

15. A pharmaceutical composition which comprises the amidinonaphthyl derivative or a pharmaceutically acceptable salt thereof according to claim 4.

16. A pharmaceutical composition which comprises the amidinonaphthyl derivative or a pharmaceutically acceptable salt thereof according to claim 5.

17. A pharmaceutical composition which comprises the amidinonaphthyl derivative or a pharmaceutically acceptable salt thereof according to claim 6.

18. A pharmaceutical composition which comprises the amidinonaphthyl derivative or a pharmaceutically acceptable salt thereof according to claim 7.

19. A method for the treatment of a thromboembolic disease which comprises administering to a person in need of such treatment a therapeutically effective amount of the pharmaceutical composition of claim 9.

20. The method of treatment of claim 19 wherein the amidinonaphthyl derivative in the pharmaceutical composition is an activated blood coagulation factor X inhibitor.

* * * * *